United States Patent
Petersen et al.

(10) Patent No.: US 12,262,872 B2
(45) Date of Patent: Apr. 1, 2025

(54) IMAGING SYSTEM WITH OPTICAL PATHWAY

(71) Applicant: Gentuity, LLC, Sudbury, MA (US)

(72) Inventors: Christopher L. Petersen, Carlisle, MA (US); Christopher C. Petroff, Groton, MA (US); Giovanni J. Ughi, Arlington (IT); Nareak Douk, Lowell, MA (US); R. Maxwell Flaherty, Topsfield, MA (US); J. Christopher Flaherty, Auburndale, FL (US)

(73) Assignee: GENTUITY, LLC, Sudbury, MA (US)

( * ) Notice: Subject to any disclaimer, the term of this patent is extended or adjusted under 35 U.S.C. 154(b) by 784 days.

(21) Appl. No.: 17/276,500

(22) PCT Filed: Sep. 17, 2019

(86) PCT No.: PCT/US2019/051447
§ 371 (c)(1),
(2) Date: Mar. 16, 2021

(87) PCT Pub. No.: WO2020/061001
PCT Pub. Date: Mar. 26, 2020

(65) Prior Publication Data
US 2021/0267442 A1 Sep. 2, 2021

Related U.S. Application Data

(60) Provisional application No. 62/850,945, filed on May 21, 2019, provisional application No. 62/840,450, (Continued)

(51) Int. Cl.
*A61B 1/04* (2006.01)
*A61B 1/00* (2006.01)
(Continued)

(52) U.S. Cl.
CPC .......... *A61B 1/042* (2013.01); *A61B 1/00025* (2013.01); *A61B 1/00057* (2013.01);
(Continued)

(58) Field of Classification Search
CPC . A61B 1/042; A61B 1/00025; A61B 1/00057; A61B 1/00082;
(Continued)

(56) References Cited

U.S. PATENT DOCUMENTS 4,460,989 A * 7/1984 Russell ................ G11B 7/0908
369/44.25
4,554,929 A 11/1985 Samson et al.
(Continued)

FOREIGN PATENT DOCUMENTS

AU 2014200116 1/2014
CN 1684624 10/2005
(Continued)

OTHER PUBLICATIONS

Japanese Office Action dated Aug. 2, 2022 issued in corresponding Japanese Application No. 2021-117103, with English translation.
(Continued)

*Primary Examiner* — Yi-Shan Yang
*Assistant Examiner* — Nicholas A Robinson
(74) *Attorney, Agent, or Firm* — Onello & Mello, LLP

(57) ABSTRACT

An imaging system for a patient is provided. The system includes an imaging probe having an elongate shaft with a proximal end, a distal portion, and a lumen extending between the proximal end and the distal portion. A rotatable optical core is positioned within the lumen of the elongate shaft. An optical assembly is positioned proximate the distal end of the rotatable optical core and is configured to direct light to tissue and collect reflected light from the tissue. An imaging assembly is constructed and arranged to optically
(Continued)

couple to the imaging probe and the imaging assembly is configured to emit light into the imaging probe and receive the reflected light collected by the optical assembly.

11 Claims, 15 Drawing Sheets

Related U.S. Application Data filed on Apr. 30, 2019, provisional application No. 62/732,114, filed on Sep. 17, 2018.

(51) Int. Cl.
*H04N 23/50* (2023.01)
*H04N 23/51* (2023.01)

(52) U.S. Cl.
CPC ......... *A61B 1/00082* (2013.01); *H04N 23/51* (2023.01); *H04N 23/555* (2023.01)

(58) Field of Classification Search
CPC .... A61B 2560/0233; A61B 2562/0242; A61B 1/00105; A61B 1/0017; A61B 1/00177; A61B 1/00179; A61B 1/00188; A61B 5/0066; A61B 5/0084; A61B 1/00172; A61B 2034/2055; H04N 23/51; H04N 23/555

See application file for complete search history.

(56) References Cited

U.S. PATENT DOCUMENTS

| | | |
|---|---|---|
| 4,566,330 A | 1/1986 | Fujii et al. |
| 4,583,184 A | 4/1986 | Murase |
| 4,588,982 A * | 5/1986 | Goodwin ............... H03M 1/24 340/688 |
| 4,594,895 A | 6/1986 | Fujii |
| 4,597,292 A | 7/1986 | Fujii et al. |
| 4,646,748 A | 3/1987 | Fujii et al. |
| 4,753,248 A | 6/1988 | Engler et al. |
| 4,951,677 A | 8/1990 | Crowley et al. |
| 4,957,482 A | 9/1990 | Shiber |
| 4,961,427 A | 10/1990 | Namekawa et al. |
| 4,983,169 A | 1/1991 | Furukawa |
| 5,002,059 A | 3/1991 | Crowley et al. |
| 5,039,193 A | 8/1991 | Snow et al. |
| 5,058,587 A | 10/1991 | Kohno et al. |
| 5,118,405 A | 6/1992 | Kaneko et al. |
| 5,127,405 A | 7/1992 | Alcala et al. |
| 5,143,075 A | 9/1992 | Ishizuka |
| 5,151,603 A | 9/1992 | Nakamura |
| 5,152,277 A | 10/1992 | Honda et al. |
| 5,158,086 A | 10/1992 | Brown et al. |
| 5,212,671 A | 5/1993 | Fujii et al. |
| 5,219,335 A | 6/1993 | Willard et al. |
| 5,321,501 A | 6/1994 | Swanson et al. |
| 5,331,309 A | 7/1994 | Sakai |
| 5,383,467 A | 1/1995 | Auer et al. |
| 5,443,781 A | 8/1995 | Saab |
| 5,456,245 A | 10/1995 | Bornhop et al. |
| 5,459,570 A | 10/1995 | Swanson et al. |
| 5,502,567 A * | 3/1996 | Pokrowsky ............... G01J 4/04 356/369 |
| 5,554,139 A | 9/1996 | Okajima |
| 5,568,314 A | 10/1996 | Omori et al. |
| 5,568,503 A | 10/1996 | Omori |
| 5,588,081 A * | 12/1996 | Takahashi ............. G02B 6/4233 385/93 |
| 5,644,427 A | 7/1997 | Omori et al. |
| 5,647,359 A | 7/1997 | Kohno et al. |
| 5,649,897 A | 7/1997 | Nakamura et al. |
| 5,689,316 A | 11/1997 | Hattori et al. |
| 5,738,100 A | 4/1998 | Yagami et al. |
| 5,745,163 A | 4/1998 | Nakamura et al. |
| 5,774,175 A | 6/1998 | Hattori |
| 5,774,261 A | 6/1998 | Omori et al. |
| 5,793,341 A | 8/1998 | Omori et al. |
| 5,818,399 A | 10/1998 | Omori et al. |
| 5,827,242 A | 10/1998 | Follmer et al. |
| 5,860,923 A | 1/1999 | Lenker et al. |
| 5,976,017 A | 11/1999 | Omori et al. |
| 5,999,591 A | 12/1999 | Kobayashi et al. |
| 6,011,580 A | 1/2000 | Hattori et al. |
| 6,011,809 A | 1/2000 | Tosaka |
| 6,019,507 A | 2/2000 | Takaki |
| 6,019,737 A | 2/2000 | Murata |
| 6,033,383 A | 3/2000 | Ginsburg |
| 6,036,682 A | 3/2000 | Lange et al. |
| 6,052,613 A | 4/2000 | Takaki |
| 6,064,684 A | 5/2000 | Yoon et al. |
| 6,069,698 A | 5/2000 | Ozawa et al. |
| 6,115,058 A | 9/2000 | Omori et al. |
| 6,134,003 A | 10/2000 | Tearney et al. |
| 6,160,826 A | 12/2000 | Swanson et al. |
| 6,165,127 A | 12/2000 | Crowley |
| 6,191,862 B1 | 2/2001 | Swanson et al. |
| 6,208,887 B1 | 3/2001 | Clarke |
| 6,217,828 B1 | 4/2001 | Bretscher et al. |
| 6,283,632 B1 | 9/2001 | Takaki |
| 6,296,608 B1 | 10/2001 | Daniels et al. |
| 6,309,358 B1 | 10/2001 | Okubo |
| 6,341,036 B1 | 1/2002 | Tearney et al. |
| 6,364,841 B1 | 4/2002 | White et al. |
| 6,383,209 B1 | 5/2002 | Crowley |
| 6,445,939 B1 | 9/2002 | Swanson et al. |
| 6,449,500 B1 | 9/2002 | Asai et al. |
| 6,471,656 B1 | 10/2002 | Shalman et al. |
| 6,485,413 B1 | 11/2002 | Boppart et al. |
| 6,485,482 B1 | 11/2002 | Belef |
| 6,520,959 B1 | 2/2003 | Wahashi et al. |
| 6,530,921 B1 | 3/2003 | Maki |
| 6,547,757 B1 | 4/2003 | Kranz et al. |
| 6,549,687 B1 | 4/2003 | Kochergin et al. |
| 6,552,796 B2 | 4/2003 | Magnin et al. |
| 6,564,087 B1 | 5/2003 | Pitris et al. |
| 6,565,514 B2 | 5/2003 | Svanerudh et al. |
| 6,570,659 B2 | 5/2003 | Schmitt |
| 6,570,893 B1 | 5/2003 | Libatique et al. |
| 6,572,553 B2 | 6/2003 | Crowley |
| 6,577,391 B1 | 6/2003 | Faupel et al. |
| 6,579,286 B1 | 6/2003 | Maki et al. |
| 6,589,233 B1 | 7/2003 | Maki |
| 6,601,459 B1 | 8/2003 | Jenni |
| 6,607,526 B1 | 8/2003 | Maki |
| 6,615,072 B1 | 9/2003 | Izatt et al. |
| 6,654,630 B2 | 11/2003 | Zuluaga et al. |
| 6,658,278 B2 | 12/2003 | Gruhl |
| 6,758,818 B2 | 7/2004 | Pantages et al. |
| 6,879,851 B2 | 4/2005 | McNamara et al. |
| 6,881,194 B2 | 4/2005 | Miyata et al. |
| 6,891,984 B2 | 5/2005 | Petersen et al. |
| 6,904,197 B2 | 6/2005 | Bhagavatula et al. |
| 6,904,199 B2 | 6/2005 | Zuluaga |
| 6,916,286 B2 | 7/2005 | Kazakevich |
| 6,925,320 B2 | 8/2005 | Gruhl |
| 6,940,885 B1 | 9/2005 | Cheng et al. |
| 7,003,184 B2 | 2/2006 | Ronnekleiv et al. |
| 7,016,024 B2 | 3/2006 | Bridge et al. |
| 7,022,118 B2 | 4/2006 | Ariura et al. |
| 7,024,025 B2 | 4/2006 | Sathyanarayana |
| 7,029,436 B2 | 4/2006 | Iizuka et al. |
| 7,099,358 B1 | 8/2006 | Chong |
| 7,134,994 B2 | 11/2006 | Alpert et al. |
| 7,155,272 B2 | 12/2006 | Yamaguchi et al. |
| 7,180,600 B2 | 2/2007 | Horii et al. |
| 7,231,243 B2 | 6/2007 | Tearney et al. |
| 7,241,286 B2 | 7/2007 | Atlas |
| 7,365,859 B2 | 4/2008 | Yun et al. |
| 7,366,376 B2 | 4/2008 | Shishkov et al. |
| 7,382,949 B2 | 6/2008 | Bouma et al. |
| 7,450,980 B2 | 11/2008 | Kawanishi |
| 7,551,293 B2 | 6/2009 | Yelin et al. |

(56) References Cited

U.S. PATENT DOCUMENTS

| | | |
|---|---|---|
| 7,567,349 B2 | 7/2009 | Tearney et al. |
| 7,625,366 B2 | 12/2009 | Atlas |
| 7,682,089 B2 | 3/2010 | Rohlen |
| 7,691,061 B2 | 4/2010 | Hirota |
| 7,711,413 B2 | 5/2010 | Feldman et al. |
| 7,724,786 B2 | 5/2010 | Bouma et al. |
| 7,733,497 B2 | 6/2010 | Yun et al. |
| 7,738,941 B2 | 6/2010 | Hirota |
| 7,740,408 B2 | 6/2010 | Yuichiro |
| 7,742,173 B2 | 6/2010 | Yun et al. |
| 7,761,139 B2 | 7/2010 | Tearney et al. |
| 7,783,337 B2 | 8/2010 | Feldman et al. |
| 7,794,230 B2 | 9/2010 | Lakin et al. |
| 7,803,141 B2 | 9/2010 | Epstein et al. |
| 7,812,961 B2 | 10/2010 | Yamaguchi |
| 7,813,609 B2 | 10/2010 | Petersen et al. |
| 7,815,632 B2 | 10/2010 | Hayakawa et al. |
| 7,843,572 B2 | 11/2010 | Tearney et al. |
| 7,847,949 B2 | 12/2010 | Tearney et al. |
| 7,848,791 B2 | 12/2010 | Schmitt et al. |
| 7,872,759 B2 | 1/2011 | Tearney et al. |
| 7,905,838 B2 | 3/2011 | Hirota |
| 7,911,621 B2 | 3/2011 | Motaghiannezam et al. |
| 7,916,387 B2 | 3/2011 | Schmitt |
| 7,920,271 B2 | 4/2011 | Vakoc et al. |
| 7,922,650 B2 | 4/2011 | McWeeney et al. |
| 7,926,562 B2 | 4/2011 | Poitzsch et al. |
| 7,935,060 B2 | 5/2011 | Schmitt et al. |
| 7,940,397 B2 | 5/2011 | Masuda |
| 7,952,718 B2 | 5/2011 | Li et al. |
| 7,969,578 B2 | 6/2011 | Yun et al. |
| 7,982,879 B2 | 7/2011 | Desjardins et al. |
| 8,018,598 B2 | 9/2011 | Cense et al. |
| 8,029,446 B2 | 10/2011 | Horiike et al. |
| 8,029,447 B2 | 10/2011 | Kanz et al. |
| 8,032,200 B2 | 10/2011 | Tearney et al. |
| 8,040,524 B2 | 10/2011 | Ozawa |
| 8,047,996 B2 | 11/2011 | Goodnow et al. |
| 8,049,900 B2 | 11/2011 | Kemp et al. |
| 8,052,605 B2 | 11/2011 | Muller et al. |
| 8,055,107 B2 | 11/2011 | Masuda |
| 8,081,316 B2 | 12/2011 | De Boer et al. |
| 8,094,319 B2 | 1/2012 | Onimura |
| 8,100,833 B2 | 1/2012 | Hirota |
| 8,108,032 B2 | 1/2012 | Onimura et al. |
| 8,116,605 B2 | 2/2012 | Petersen et al. |
| 8,125,648 B2 | 2/2012 | Milner et al. |
| 8,149,418 B2 | 4/2012 | Tearney et al. |
| 8,157,741 B2 | 4/2012 | Hirota |
| 8,157,742 B2 | 4/2012 | Taylor |
| 8,174,702 B2 | 5/2012 | Tearney et al. |
| 8,206,372 B2 | 6/2012 | Larson et al. |
| 8,206,377 B2 | 6/2012 | Petroff |
| 8,208,995 B2 | 6/2012 | Tearney et al. |
| 8,231,516 B2 | 7/2012 | Maschke |
| 8,241,196 B2 | 8/2012 | Scibona |
| 8,289,522 B2 | 10/2012 | Tearney et al. |
| RE43,875 E | 12/2012 | Shishkov et al. |
| 8,322,932 B2 | 12/2012 | Irisawa |
| 8,325,419 B2 | 12/2012 | Schmitt |
| 8,337,379 B2 | 12/2012 | Fletcher et al. |
| 8,339,592 B2 | 12/2012 | Hlavinka et al. |
| 8,346,348 B2 | 1/2013 | Onimura |
| 8,351,665 B2 | 1/2013 | Tearney et al. |
| 8,355,138 B2 | 1/2013 | Yun et al. |
| 8,384,907 B2 | 2/2013 | Tearney et al. |
| 8,384,909 B2 | 2/2013 | Yun et al. |
| 8,412,312 B2 | 4/2013 | Judell et al. |
| 8,414,496 B2 | 4/2013 | Goodnow et al. |
| 8,449,439 B2 | 5/2013 | Fletcher et al. |
| 8,449,468 B2 | 5/2013 | Petersen et al. |
| 8,452,371 B2 | 5/2013 | Feldman et al. |
| 8,473,037 B2 | 6/2013 | Irisawa |
| 8,473,073 B2 | 6/2013 | Vardiman |
| 8,478,384 B2 | 7/2013 | Schmitt et al. |
| 8,478,387 B2 | 7/2013 | Xu |
| 8,493,567 B2 | 7/2013 | Inoue |
| 8,501,015 B2 | 8/2013 | Fletcher et al. |
| 8,503,844 B2 | 8/2013 | Petersen et al. |
| 8,531,676 B2 | 9/2013 | Condit et al. |
| 8,535,210 B2 | 9/2013 | Kolenbrander et al. |
| 8,556,820 B2 | 10/2013 | Alpert et al. |
| 8,559,012 B2 | 10/2013 | Tearney et al. |
| 8,581,643 B1 | 11/2013 | Schmitt |
| 8,582,109 B1 | 11/2013 | Schmitt |
| 8,582,619 B2 | 11/2013 | Adler |
| 8,582,934 B2 | 11/2013 | Adler et al. |
| 8,585,592 B2 | 11/2013 | Luevano et al. |
| 8,593,619 B2 | 11/2013 | Colice et al. |
| 8,593,641 B2 | 11/2013 | Kemp et al. |
| 8,618,032 B2 | 12/2013 | Kurita |
| 8,626,453 B2 | 1/2014 | Myoujou et al. |
| 8,636,659 B2 | 1/2014 | Alpert et al. |
| 8,676,013 B2 | 3/2014 | Bouma et al. |
| 8,676,299 B2 | 3/2014 | Schmitt et al. |
| 8,687,201 B2 | 4/2014 | Adler |
| 8,705,046 B2 | 4/2014 | Yun et al. |
| 8,712,506 B2 | 4/2014 | Courtney et al. |
| 8,753,281 B2 | 6/2014 | Schmitt et al. |
| 8,760,663 B2 | 6/2014 | Tearney et al. |
| 8,761,469 B2 | 6/2014 | Kemp et al. |
| 8,786,336 B1 | 7/2014 | Schmitt |
| 8,804,126 B2 | 8/2014 | Tearney et al. |
| 8,808,186 B2 | 8/2014 | Fruland et al. |
| 8,810,901 B2 | 8/2014 | Huber et al. |
| 8,825,142 B2 | 9/2014 | Suehara |
| 8,827,926 B2 | 9/2014 | Kinoshita et al. |
| 8,831,321 B1 | 9/2014 | Elbasiony |
| 8,868,159 B2 | 10/2014 | Onimura |
| 8,885,171 B2 | 11/2014 | Watanabe et al. |
| 8,896,838 B2 | 11/2014 | Tearney et al. |
| 8,902,941 B2 | 12/2014 | Schmitt |
| 8,909,324 B2 | 12/2014 | Furuichi |
| 8,911,357 B2 | 12/2014 | Omori |
| 8,926,590 B2 | 1/2015 | Petroff |
| 8,928,889 B2 | 1/2015 | Tearney et al. |
| 8,945,526 B2 | 2/2015 | Akitsu et al. |
| 8,948,228 B2 | 2/2015 | Adler |
| 8,948,613 B2 | 2/2015 | Schmitt et al. |
| 8,953,911 B1 | 2/2015 | Xu et al. |
| 8,983,582 B2 | 3/2015 | Webler |
| 8,989,849 B2 | 3/2015 | Milner et al. |
| 8,994,803 B2 | 3/2015 | Kaneko |
| 8,996,099 B2 | 3/2015 | Feldman et al. |
| 8,998,797 B2 | 4/2015 | Omori |
| 9,007,696 B2 | 4/2015 | Petersen et al. |
| 9,033,890 B2 | 5/2015 | Furuichi |
| 9,036,966 B2 | 5/2015 | Bhagavatula et al. |
| 9,039,626 B2 | 5/2015 | Courtney |
| 9,060,689 B2 | 6/2015 | Tearney et al. |
| 9,069,396 B2 | 6/2015 | Adler et al. |
| 9,076,202 B2 | 7/2015 | Courtney et al. |
| 9,081,148 B2 | 7/2015 | Tearney et al. |
| 9,084,532 B2 | 7/2015 | Horiike |
| 9,087,368 B2 | 7/2015 | Tearney et al. |
| 9,091,524 B2 | 7/2015 | Adler et al. |
| 9,101,298 B2 | 8/2015 | Hossack et al. |
| 9,107,682 B2 | 8/2015 | Scheller et al. |
| 9,107,687 B2 | 8/2015 | Kinoshita et al. |
| 9,121,926 B2 | 9/2015 | Nair et al. |
| 9,131,850 B2 | 9/2015 | Liu et al. |
| 9,138,147 B2 | 9/2015 | Schmitt et al. |
| 9,164,240 B2 | 10/2015 | Schmitt et al. |
| 9,168,003 B2 | 10/2015 | Suzuki et al. |
| 9,173,572 B2 | 11/2015 | Colice et al. |
| 9,173,591 B2 | 11/2015 | Elbasiony et al. |
| 9,194,690 B2 | 11/2015 | Bhagavatula et al. |
| 9,207,064 B2 | 12/2015 | Inoue |
| 9,226,660 B2 | 1/2016 | De Boer et al. |
| 9,226,665 B2 | 1/2016 | Tearney et al. |
| 9,254,102 B2 | 2/2016 | Tearney et al. |
| 9,289,127 B2 | 3/2016 | Mitsuhashi et al. |
| 9,289,582 B2 | 3/2016 | Suehara |
| 9,295,450 B2 | 3/2016 | Furuichi et al. |

(56) References Cited

U.S. PATENT DOCUMENTS

| | | |
|---|---|---|
| 9,295,455 B2 | 3/2016 | Karino et al. |
| 9,301,687 B2 | 4/2016 | Kemp |
| 9,304,121 B2 | 4/2016 | Tearney et al. |
| 9,322,639 B2 | 4/2016 | Watanabe et al. |
| 9,326,789 B2 | 5/2016 | Fruland et al. |
| 9,330,092 B2 | 5/2016 | Vakoc et al. |
| 9,339,173 B2 | 5/2016 | McWeeney et al. |
| 9,339,348 B2 | 5/2016 | Davies et al. |
| 9,345,864 B2 | 5/2016 | Suehara |
| 9,347,765 B2 | 5/2016 | Kemp et al. |
| 9,351,698 B2 | 5/2016 | Dascal et al. |
| 9,357,923 B2 | 6/2016 | Courtney et al. |
| 9,375,148 B2 | 6/2016 | Senoo |
| 9,375,158 B2 | 6/2016 | Vakoc et al. |
| 9,375,164 B2 | 6/2016 | Tolkowsky et al. |
| 9,377,290 B2 | 6/2016 | Yun et al. |
| 9,404,731 B2 | 8/2016 | Adler et al. |
| 9,408,539 B2 | 8/2016 | Tearney et al. |
| 9,417,052 B2 | 8/2016 | Adler |
| 9,435,736 B2 | 9/2016 | Kolenbrander et al. |
| 9,435,956 B1 | 9/2016 | Xu et al. |
| 9,439,570 B2 | 9/2016 | Vertikov |
| 9,441,948 B2 | 9/2016 | Vakoc et al. |
| 9,462,950 B2 | 10/2016 | Xu |
| 9,464,883 B2 | 10/2016 | Swanson et al. |
| 9,488,464 B1 | 11/2016 | Schmitt |
| 9,507,074 B2 | 11/2016 | Zhu et al. |
| 9,513,276 B2 | 12/2016 | Tearney et al. |
| 9,526,424 B2 | 12/2016 | Judell et al. |
| 9,566,752 B2 | 2/2017 | Hartkorn |
| 9,572,495 B2 | 2/2017 | Schmitt et al. |
| 9,572,496 B2 | 2/2017 | Furuichi et al. |
| 9,574,870 B2 | 2/2017 | Yamazaki et al. |
| 9,591,967 B2 | 3/2017 | Nishiyama et al. |
| 9,605,942 B2 | 3/2017 | Staloff |
| 9,610,064 B2 | 4/2017 | Adler et al. |
| 9,615,771 B2 | 4/2017 | Furuichi et al. |
| 9,622,706 B2 | 4/2017 | Dick et al. |
| 9,638,862 B2 | 5/2017 | Bhagavatula et al. |
| 9,642,531 B2 | 5/2017 | Tearney et al. |
| 9,645,322 B2 | 5/2017 | Murashima et al. |
| 9,646,377 B2 | 5/2017 | Tearney et al. |
| 9,659,375 B2 | 5/2017 | Zagrodsky et al. |
| 9,702,687 B2 | 7/2017 | Schmitt |
| 9,702,762 B2 | 7/2017 | Friedman et al. |
| 9,704,240 B2 | 7/2017 | Lam et al. |
| 9,710,891 B2 | 7/2017 | Sakamoto |
| 9,730,613 B2 | 8/2017 | Stigall et al. |
| 9,763,623 B2 | 9/2017 | Tearney et al. |
| 9,778,020 B2 | 10/2017 | Tumlinson et al. |
| 9,788,790 B2 | 10/2017 | Black et al. |
| 9,808,303 B2 | 11/2017 | Ryba et al. |
| 9,812,846 B2 | 11/2017 | Yun et al. |
| 9,833,221 B2 | 12/2017 | Hutchins et al. |
| 9,836,835 B2 | 12/2017 | Furuichi et al. |
| 9,843,159 B2 | 12/2017 | Cable et al. |
| 9,855,020 B2 | 1/2018 | Nair et al. |
| 9,858,387 B2 | 1/2018 | Lavi et al. |
| 9,864,140 B2 | 1/2018 | Adler et al. |
| 9,872,665 B2 | 1/2018 | Okubo et al. |
| 9,891,044 B2 | 2/2018 | Tu et al. |
| 9,897,538 B2 | 2/2018 | Tearney et al. |
| 9,907,527 B2 | 3/2018 | Dascal et al. |
| 9,933,244 B2 | 4/2018 | Krol et al. |
| 9,940,723 B2 | 4/2018 | Gopinath et al. |
| 9,943,233 B2 | 4/2018 | Lavi et al. |
| 9,962,127 B2 | 5/2018 | Wang et al. |
| 9,980,648 B2 | 5/2018 | Itoh et al. |
| 9,983,356 B2 | 5/2018 | Schmitt et al. |
| 9,986,938 B2 | 6/2018 | Tu et al. |
| 9,989,945 B2 | 6/2018 | Adler et al. |
| 9,996,921 B2 | 6/2018 | Ambwani et al. |
| 10,004,400 B2 | 6/2018 | Nakamoto et al. |
| 10,004,863 B2 | 6/2018 | Vazales et al. |
| 10,006,753 B2 | 6/2018 | Schmitt et al. |
| 10,028,725 B2 | 7/2018 | Petroff |
| 10,089,755 B2 | 10/2018 | Griffin et al. |
| 10,092,188 B2 | 10/2018 | Jaffer et al. |
| 10,109,058 B2 | 10/2018 | Ambwani et al. |
| 10,124,153 B2 | 11/2018 | Feig et al. |
| 10,140,712 B2 | 11/2018 | Ambwani |
| 10,162,114 B2 | 12/2018 | Bhagavatula et al. |
| 10,172,582 B2 | 1/2019 | Dascal et al. |
| 10,186,056 B2 | 1/2019 | Senzig et al. |
| 10,207,124 B2 | 2/2019 | Shimizu et al. |
| 10,213,109 B2 | 2/2019 | Itoh et al. |
| 10,213,186 B2 | 2/2019 | Inoue et al. |
| 10,219,780 B2 | 3/2019 | Castella et al. |
| 10,222,956 B2 | 3/2019 | Gopinath et al. |
| 10,238,349 B2 | 3/2019 | Furuichi et al. |
| 10,238,816 B2 | 3/2019 | Matsubara et al. |
| 10,261,223 B2 | 4/2019 | Tearney et al. |
| 10,271,818 B2 | 4/2019 | Kobayashi |
| 10,285,568 B2 | 5/2019 | Tearney et al. |
| 10,327,726 B2 | 6/2019 | Dascal et al. |
| 10,331,099 B2 | 6/2019 | Adler et al. |
| 10,335,039 B2 | 7/2019 | Xu |
| 10,338,795 B2 | 7/2019 | Gopinath et al. |
| 10,342,502 B2 | 7/2019 | Dascal et al. |
| 10,387,013 B2 | 8/2019 | Jamello |
| 10,453,190 B2 | 10/2019 | Griffin |
| 10,453,191 B2 | 10/2019 | Shalev et al. |
| 10,453,196 B2 | 10/2019 | Ambwani |
| 10,463,254 B2 | 11/2019 | Tearney et al. |
| 10,499,813 B2 | 12/2019 | Adler |
| 10,529,093 B2 | 1/2020 | Griffin et al. |
| 10,551,251 B2 | 2/2020 | Friedman et al. |
| 10,593,037 B2 | 3/2020 | Gopinath |
| 10,631,718 B2 | 4/2020 | Petroff et al. |
| 10,631,754 B2 | 4/2020 | Gopinath |
| 10,646,198 B2 | 5/2020 | Peterson et al. |
| 10,648,918 B2 | 5/2020 | Schmitt |
| 10,687,777 B2 | 6/2020 | Dascal et al. |
| 10,713,786 B2 | 7/2020 | Ambwani et al. |
| 10,729,376 B2 | 8/2020 | Courtney |
| 10,792,012 B2 | 10/2020 | Hutchins et al. |
| 10,806,421 B2 | 10/2020 | Keller |
| 10,878,572 B2 | 12/2020 | Gopinath et al. |
| 10,902,599 B2 | 1/2021 | Ambwani et al. |
| 11,051,761 B2 | 7/2021 | Courtney et al. |
| 11,058,385 B2 | 7/2021 | Kunio |
| 11,064,873 B2 | 7/2021 | Petroff et al. |
| 11,278,206 B2 | 3/2022 | Petroff et al. |
| 11,583,172 B2 | 2/2023 | Petroff et al. |
| 11,684,242 B2 | 6/2023 | Petroff et al. |
| 2002/0041724 A1 | 4/2002 | Ronnekleiv et al. |
| 2002/0045811 A1 | 4/2002 | Kittrell et al. |
| 2002/0072880 A1 | 6/2002 | Svanerudh et al. |
| 2002/0099289 A1 | 7/2002 | Crowley |
| 2002/0131049 A1 | 9/2002 | Schmitt |
| 2002/0151799 A1 | 10/2002 | Pantages et al. |
| 2002/0151823 A1 | 10/2002 | Miyata et al. |
| 2002/0163622 A1 | 11/2002 | Magnin et al. |
| 2002/0183601 A1 | 12/2002 | Tearney et al. |
| 2002/0183622 A1 | 12/2002 | Zuluaga et al. |
| 2002/0188204 A1 | 12/2002 | McNamara et al. |
| 2002/0198457 A1 | 12/2002 | Tearney et al. |
| 2003/0004417 A1 | 1/2003 | Ariura et al. |
| 2003/0013952 A1 | 1/2003 | Iizuka et al. |
| 2003/0032863 A1 | 2/2003 | Kazakevich |
| 2003/0073909 A1 | 4/2003 | Gruhl |
| 2003/0081875 A1 | 5/2003 | Kochergin et al. |
| 2003/0147551 A1 | 8/2003 | Sathyanarayana |
| 2003/0165291 A1 | 9/2003 | Bhagavatula et al. |
| 2003/0216621 A1 | 11/2003 | Alpert et al. |
| 2004/0017961 A1 | 1/2004 | Petersen et al. |
| 2004/0034290 A1 | 2/2004 | Zuluaga |
| 2004/0082861 A1 | 4/2004 | Gruhl |
| 2004/0092913 A1 | 5/2004 | Hennings et al. |
| 2004/0215166 A1 | 10/2004 | Atlas |
| 2005/0004453 A1 | 1/2005 | Tearney et al. |
| 2005/0038406 A1 | 2/2005 | Epstein et al. |
| 2005/0101870 A1 | 5/2005 | Yamaguchi et al. |
| 2005/0128488 A1 | 6/2005 | Yelin et al. |

(56) References Cited

U.S. PATENT DOCUMENTS

| | | | |
|---|---|---|---|
| 2005/0163426 A1* | 7/2005 | Fermann | H01S 3/1115 385/37 |
| 2005/0168751 A1 | 8/2005 | Horii et al. | |
| 2005/0187422 A1 | 8/2005 | Maschke | |
| 2005/0201662 A1 | 9/2005 | Petersen et al. | |
| 2005/0221277 A1 | 10/2005 | Kawanishi | |
| 2005/0259242 A1 | 11/2005 | Bridge et al. | |
| 2005/0272975 A1 | 12/2005 | McWeeney et al. | |
| 2005/0288583 A1 | 12/2005 | Hirota | |
| 2006/0039004 A1 | 2/2006 | De Boer et al. | |
| 2006/0055936 A1 | 3/2006 | Yun et al. | |
| 2006/0058622 A1 | 3/2006 | Tearney et al. | |
| 2006/0067620 A1 | 3/2006 | Shishkov et al. | |
| 2006/0091566 A1 | 5/2006 | Yang et al. | |
| 2006/0093276 A1 | 5/2006 | Bouma et al. | |
| 2006/0095065 A1 | 5/2006 | Tanimura et al. | |
| 2006/0135870 A1 | 6/2006 | Webler | |
| 2006/0166176 A1 | 7/2006 | Lakin et al. | |
| 2006/0227333 A1 | 10/2006 | Tearney et al. | |
| 2006/0241484 A1 | 10/2006 | Horiike et al. | |
| 2006/0241493 A1 | 10/2006 | Feldman et al. | |
| 2006/0241503 A1 | 10/2006 | Schmitt et al. | |
| 2006/0244973 A1 | 11/2006 | Yun et al. | |
| 2006/0247743 A1 | 11/2006 | Hayakawa et al. | |
| 2006/0279742 A1 | 12/2006 | Tearney et al. | |
| 2007/0012886 A1 | 1/2007 | Tearney et al. | |
| 2007/0015969 A1 | 1/2007 | Feldman et al. | |
| 2007/0035743 A1 | 2/2007 | Vakoc et al. | |
| 2007/0038040 A1 | 2/2007 | Cense et al. | |
| 2007/0038274 A1 | 2/2007 | Ishii et al. | |
| 2007/0060822 A1 | 3/2007 | Alpert et al. | |
| 2007/0073162 A1 | 3/2007 | Tearney et al. | |
| 2007/0081236 A1 | 4/2007 | Tearney et al. | |
| 2007/0106155 A1 | 5/2007 | Goodnow et al. | |
| 2007/0121196 A1 | 5/2007 | Tearney et al. | |
| 2007/0201033 A1 | 8/2007 | Desjardins et al. | |
| 2007/0229801 A1 | 10/2007 | Tearney et al. | |
| 2007/0232890 A1 | 10/2007 | Hirota | |
| 2007/0232891 A1 | 10/2007 | Hirota | |
| 2007/0232892 A1 | 10/2007 | Hirota | |
| 2007/0232893 A1 | 10/2007 | Tanioka | |
| 2007/0233396 A1 | 10/2007 | Tearney et al. | |
| 2007/0236700 A1 | 10/2007 | Yun et al. | |
| 2007/0244391 A1 | 10/2007 | Hirota | |
| 2007/0260198 A1 | 11/2007 | Atlas | |
| 2007/0268456 A1 | 11/2007 | Ohbayshi et al. | |
| 2008/0002211 A1 | 1/2008 | Park et al. | |
| 2008/0004530 A1 | 1/2008 | Feldman et al. | |
| 2008/0007734 A1 | 1/2008 | Park et al. | |
| 2008/0019908 A1 | 1/2008 | Akitsu et al. | |
| 2008/0021275 A1 | 1/2008 | Tearney et al. | |
| 2008/0045394 A1 | 2/2008 | Fletcher et al. | |
| 2008/0049232 A1 | 2/2008 | Vakoc et al. | |
| 2008/0161696 A1 | 7/2008 | Schmitt et al. | |
| 2008/0165366 A1 | 7/2008 | Schmitt | |
| 2008/0177139 A1 | 7/2008 | Courtney et al. | |
| 2008/0181263 A1 | 7/2008 | Bouma et al. | |
| 2008/0208227 A1 | 8/2008 | Kadykowski et al. | |
| 2008/0225301 A1 | 9/2008 | Yamaguchi | |
| 2008/0262346 A1 | 10/2008 | Assis et al. | |
| 2008/0269572 A1 | 10/2008 | Kanz et al. | |
| 2008/0291463 A1 | 11/2008 | Milner et al. | |
| 2008/0297806 A1 | 12/2008 | Motaghiannezam et al. | |
| 2009/0018393 A1 | 1/2009 | Dick et al. | |
| 2009/0027689 A1 | 1/2009 | Yun et al. | |
| 2009/0036782 A1 | 2/2009 | Vakoc et al. | |
| 2009/0043191 A1 | 2/2009 | Castella et al. | |
| 2009/0046295 A1 | 2/2009 | Kemp et al. | |
| 2009/0046980 A1 | 2/2009 | Rohlen | |
| 2009/0073454 A1 | 3/2009 | Ozawa | |
| 2009/0073455 A1 | 3/2009 | Onimura | |
| 2009/0093980 A1 | 4/2009 | Kemp et al. | |
| 2009/0122320 A1 | 5/2009 | Petersen et al. | |
| 2009/0131801 A1 | 5/2009 | Suter et al. | |
| 2009/0135429 A1 | 5/2009 | Masuda | |
| 2009/0143686 A1 | 6/2009 | Onimura et al. | |
| 2009/0182246 A1 | 7/2009 | Kinoshita et al. | |
| 2009/0192519 A1 | 7/2009 | Omori | |
| 2009/0196477 A1 | 8/2009 | Cense et al. | |
| 2009/0196554 A1 | 8/2009 | Irisawa | |
| 2009/0251704 A1 | 10/2009 | Masuda | |
| 2009/0261240 A1 | 10/2009 | Watanabe et al. | |
| 2009/0262361 A1 | 10/2009 | Tanioka et al. | |
| 2009/0283258 A1 | 11/2009 | Poitzsch et al. | |
| 2009/0299195 A1 | 12/2009 | Muller et al. | |
| 2009/0306520 A1 | 12/2009 | Schmitt et al. | |
| 2009/0323076 A1 | 12/2009 | Li et al. | |
| 2010/0019189 A1 | 1/2010 | Kurita | |
| 2010/0042084 A1 | 2/2010 | Nariyuki et al. | |
| 2010/0073682 A1 | 3/2010 | Inoue | |
| 2010/0076320 A1 | 3/2010 | Petersen et al. | |
| 2010/0094127 A1 | 4/2010 | Xu | |
| 2010/0110414 A1 | 5/2010 | Colice et al. | |
| 2010/0130872 A1 | 5/2010 | Irisawa | |
| 2010/0157309 A1 | 6/2010 | Tearney et al. | |
| 2010/0158339 A1 | 6/2010 | Omori | |
| 2010/0160134 A1 | 6/2010 | Scibona | |
| 2010/0160780 A1 | 6/2010 | Swan et al. | |
| 2010/0168587 A1 | 7/2010 | Feldman et al. | |
| 2010/0220334 A1 | 9/2010 | Condit et al. | |
| 2010/0241154 A1 | 9/2010 | Larson et al. | |
| 2010/0249588 A1 | 9/2010 | Knight | |
| 2010/0249601 A1 | 9/2010 | Courtney | |
| 2010/0253949 A1 | 10/2010 | Adler et al. | |
| 2010/0298908 A1 | 11/2010 | Vardiman | |
| 2010/0305452 A1 | 12/2010 | Black et al. | |
| 2010/0309477 A1 | 12/2010 | Yun et al. | |
| 2011/0007315 A1 | 1/2011 | Petersen et al. | |
| 2011/0009741 A1 | 1/2011 | Matthews et al. | |
| 2011/0019182 A1 | 1/2011 | Hlavinka et al. | |
| 2011/0058178 A1 | 3/2011 | Tearney et al. | |
| 2011/0071404 A1 | 3/2011 | Schmitt et al. | |
| 2011/0071405 A1 | 3/2011 | Judell et al. | |
| 2011/0092823 A1 | 4/2011 | Tearney et al. | |
| 2011/0101207 A1 | 5/2011 | Schmitt | |
| 2011/0143905 A1 | 6/2011 | Kolenbrander et al. | |
| 2011/0144504 A1 | 6/2011 | Tearney et al. | |
| 2011/0149296 A1 | 6/2011 | Tearney et al. | |
| 2011/0151980 A1 | 6/2011 | Petroff | |
| 2011/0152771 A1 | 6/2011 | Milner et al. | |
| 2011/0157686 A1 | 6/2011 | Huber et al. | |
| 2011/0172511 A1 | 7/2011 | Petersen et al. | |
| 2011/0178398 A1 | 7/2011 | Tearney et al. | |
| 2011/0178413 A1 | 7/2011 | Schmitt et al. | |
| 2011/0190586 A1 | 8/2011 | Kemp | |
| 2011/0196217 A1 | 8/2011 | Myoujou et al. | |
| 2011/0201924 A1 | 8/2011 | Tearney et al. | |
| 2011/0216325 A1 | 9/2011 | Schmitt | |
| 2011/0218403 A1 | 9/2011 | Tearney et al. | |
| 2011/0224541 A1 | 9/2011 | Yun et al. | |
| 2011/0228280 A1 | 9/2011 | Schmitt et al. | |
| 2011/0237958 A1 | 9/2011 | Onimura | |
| 2011/0245683 A1 | 10/2011 | Onimura | |
| 2011/0245684 A1 | 10/2011 | Onimura | |
| 2011/0261366 A1 | 10/2011 | Tearney et al. | |
| 2011/0267340 A1 | 11/2011 | Kraus et al. | |
| 2011/0270091 A1 | 11/2011 | Hossack et al. | |
| 2011/0292400 A1 | 12/2011 | Fleming et al. | |
| 2011/0299091 A1 | 12/2011 | Yun et al. | |
| 2012/0002928 A1 | 1/2012 | Irisawa | |
| 2012/0004506 A1 | 1/2012 | Tearney et al. | |
| 2012/0007974 A1 | 1/2012 | Kaneko | |
| 2012/0008146 A1 | 1/2012 | Tearney et al. | |
| 2012/0013914 A1 | 1/2012 | Kemp et al. | |
| 2012/0022360 A1 | 1/2012 | Kemp | |
| 2012/0035454 A1 | 2/2012 | Tearney et al. | |
| 2012/0053918 A1 | 3/2012 | Taylor | |
| 2012/0057157 A1 | 3/2012 | Petersen et al. | |
| 2012/0063570 A1 | 3/2012 | Furuichi et al. | |
| 2012/0065517 A1 | 3/2012 | Goodnow et al. | |
| 2012/0071736 A1 | 3/2012 | Luevano et al. | |
| 2012/0123352 A1 | 5/2012 | Fruland et al. | |
| 2012/0127476 A1 | 5/2012 | De Boer et al. | |
| 2012/0135384 A1 | 5/2012 | Nakao | |

(56) References Cited

U.S. PATENT DOCUMENTS

| | | |
|---|---|---|
| 2012/0170848 A1 | 7/2012 | Kemp et al. |
| 2012/0190974 A1 | 7/2012 | Suehara |
| 2012/0215091 A1 | 8/2012 | Suzuki et al. |
| 2012/0220836 A1 | 8/2012 | Alpert et al. |
| 2012/0226151 A1 | 9/2012 | Irisawa |
| 2012/0236883 A1 | 9/2012 | Adler |
| 2012/0238869 A1 | 9/2012 | Schmitt et al. |
| 2012/0243761 A1 | 9/2012 | Senzig et al. |
| 2012/0245459 A1 | 9/2012 | Senoo |
| 2012/0250028 A1 | 10/2012 | Schmitt et al. |
| 2012/0253114 A1 | 10/2012 | Kinoshita et al. |
| 2012/0253123 A1 | 10/2012 | Shimizu et al. |
| 2012/0253184 A1 | 10/2012 | Furuichi et al. |
| 2012/0253185 A1 | 10/2012 | Furuichi |
| 2012/0281237 A1 | 11/2012 | Tearney et al. |
| 2012/0310081 A1 | 12/2012 | Adler et al. |
| 2012/0330101 A1 | 12/2012 | Brennan et al. |
| 2013/0002843 A1 | 1/2013 | Horiike |
| 2013/0006104 A1 | 1/2013 | Mitsuhashi et al. |
| 2013/0006105 A1 | 1/2013 | Furuichi |
| 2013/0010303 A1 | 1/2013 | Petersen et al. |
| 2013/0012810 A1 | 1/2013 | Nakamoto et al. |
| 2013/0012811 A1 | 1/2013 | Schmitt et al. |
| 2013/0023760 A1 | 1/2013 | Liu et al. |
| 2013/0023761 A1 | 1/2013 | Petroff |
| 2013/0046190 A1 | 2/2013 | Davies et al. |
| 2013/0051728 A1 | 2/2013 | Petroff et al. |
| 2013/0072367 A1 | 3/2013 | Fletcher et al. |
| 2013/0072805 A1 | 3/2013 | Schmitt et al. |
| 2013/0079630 A1 | 3/2013 | Horiike |
| 2013/0079631 A1 | 3/2013 | Horiike et al. |
| 2013/0100455 A1 | 4/2013 | Tearney et al. |
| 2013/0107043 A1 | 5/2013 | Fletcher et al. |
| 2013/0116671 A1 | 5/2013 | Scheller et al. |
| 2013/0128274 A1 | 5/2013 | Yun et al. |
| 2013/0148106 A1 | 6/2013 | Tearney et al. |
| 2013/0176571 A1 | 7/2013 | Tearney et al. |
| 2013/0185023 A1 | 7/2013 | Vakoc et al. |
| 2013/0188850 A1 | 7/2013 | Tearney et al. |
| 2013/0215427 A1 | 8/2013 | Bouma et al. |
| 2013/0216114 A1 | 8/2013 | Courtney et al. |
| 2013/0217964 A1 | 8/2013 | Kumoyama et al. |
| 2013/0222813 A1 | 8/2013 | Watanabe et al. |
| 2013/0246034 A1 | 9/2013 | Sharma et al. |
| 2013/0266259 A1 | 10/2013 | Bhagavatula et al. |
| 2013/0278936 A1 | 10/2013 | Inoue |
| 2013/0281844 A1 | 10/2013 | Karino et al. |
| 2013/0303907 A1 | 11/2013 | Corl |
| 2013/0310698 A1 | 11/2013 | Judell et al. |
| 2013/0314716 A1 | 11/2013 | Tearney et al. |
| 2013/0331689 A1 | 12/2013 | Le et al. |
| 2014/0005023 A1 | 1/2014 | Kolenbrander et al. |
| 2014/0018669 A1 | 1/2014 | Xu |
| 2014/0024930 A1 | 1/2014 | Furuichi et al. |
| 2014/0024931 A1 | 1/2014 | Winston et al. |
| 2014/0031677 A1 | 1/2014 | Iftimia et al. |
| 2014/0031679 A1* | 1/2014 | Tashiro ............... A61B 5/0077 600/425 |
| 2014/0036941 A1 | 2/2014 | Adler |
| 2014/0063488 A1 | 3/2014 | Adler |
| 2014/0066706 A1 | 3/2014 | McWeeney et al. |
| 2014/0066756 A1 | 3/2014 | Sinclair et al. |
| 2014/0083970 A1 | 3/2014 | Kumar et al. |
| 2014/0088411 A1 | 3/2014 | Suehara et al. |
| 2014/0094697 A1 | 4/2014 | Petroff et al. |
| 2014/0100451 A1 | 4/2014 | Tolkowsky et al. |
| 2014/0114182 A1 | 4/2014 | Petersen et al. |
| 2014/0142427 A1 | 5/2014 | Petroff |
| 2014/0142432 A1 | 5/2014 | Hutchins et al. |
| 2014/0142436 A1 | 5/2014 | Hutchins et al. |
| 2014/0150782 A1 | 6/2014 | Vazales et al. |
| 2014/0177935 A1 | 6/2014 | Nair et al. |
| 2014/0180071 A1 | 6/2014 | Stigall et al. |
| 2014/0180083 A1 | 6/2014 | Hoseit |
| 2014/0180121 A1 | 6/2014 | Fong |
| 2014/0187929 A1 | 7/2014 | Schmitt et al. |
| 2014/0200867 A1 | 7/2014 | Lavi et al. |
| 2014/0206989 A1 | 7/2014 | Colice et al. |
| 2014/0207168 A1 | 7/2014 | Kawaura et al. |
| 2014/0218742 A1 | 8/2014 | Adler |
| 2014/0243876 A1 | 8/2014 | Suehara |
| 2014/0247454 A1 | 9/2014 | Bhagavatula et al. |
| 2014/0249407 A1 | 9/2014 | Adler et al. |
| 2014/0257087 A1 | 9/2014 | Elbasiony et al. |
| 2014/0267038 A1 | 9/2014 | Adler et al. |
| 2014/0268167 A1 | 9/2014 | Friedman et al. |
| 2014/0270436 A1 | 9/2014 | Dascal et al. |
| 2014/0270445 A1 | 9/2014 | Kemp |
| 2014/0275995 A1 | 9/2014 | Sheehan |
| 2014/0276020 A1 | 9/2014 | Hutchins et al. |
| 2014/0276108 A1 | 9/2014 | Vertikov |
| 2014/0277072 A1 | 9/2014 | Suehara |
| 2014/0301620 A1 | 10/2014 | Tearney et al. |
| 2014/0323877 A1 | 10/2014 | Courtney et al. |
| 2014/0346693 A1 | 11/2014 | Hartkorn |
| 2014/0371598 A1 | 12/2014 | Okubo et al. |
| 2014/0376000 A1 | 12/2014 | Swanson et al. |
| 2014/0378845 A1 | 12/2014 | Nadkarni |
| 2014/0379269 A1 | 12/2014 | Schmitt |
| 2015/0005615 A1 | 1/2015 | Inoue et al. |
| 2015/0005626 A1 | 1/2015 | Kaneko |
| 2015/0005627 A1 | 1/2015 | Itoh et al. |
| 2015/0005628 A1 | 1/2015 | Itoh et al. |
| 2015/0025369 A1 | 1/2015 | Bhagavatula et al. |
| 2015/0029513 A1 | 1/2015 | Tearney et al. |
| 2015/0036146 A1 | 2/2015 | Staloff |
| 2015/0049339 A1 | 2/2015 | Tearney et al. |
| 2015/0051485 A1 | 2/2015 | Itoh et al. |
| 2015/0057958 A1 | 2/2015 | Watanabe et al. |
| 2015/0077755 A1 | 3/2015 | Yun et al. |
| 2015/0080700 A1 | 3/2015 | Fruland et al. |
| 2015/0099968 A1 | 4/2015 | Jamello |
| 2015/0099975 A1 | 4/2015 | Lam et al. |
| 2015/0119707 A1 | 4/2015 | Petroff |
| 2015/0133773 A1 | 5/2015 | Jaffer et al. |
| 2015/0133776 A1 | 5/2015 | Hoffman |
| 2015/0133789 A1 | 5/2015 | Ariura et al. |
| 2015/0153157 A1 | 6/2015 | Schmitt et al. |
| 2015/0164331 A1 | 6/2015 | Burgess et al. |
| 2015/0164423 A1 | 6/2015 | Webler |
| 2015/0182192 A1 | 7/2015 | Kaneko |
| 2015/0190054 A1 | 7/2015 | Kaneko |
| 2015/0192405 A1 | 7/2015 | Schmitt |
| 2015/0196285 A1 | 7/2015 | Mori |
| 2015/0209526 A1 | 7/2015 | Matsubara et al. |
| 2015/0216415 A1 | 8/2015 | Uribe-Patarroyo et al. |
| 2015/0219854 A1 | 8/2015 | Bhagavatula et al. |
| 2015/0230775 A1 | 8/2015 | Kobayashi |
| 2015/0238084 A1 | 8/2015 | Tearney et al. |
| 2015/0238121 A1 | 8/2015 | Tu et al. |
| 2015/0245768 A1 | 9/2015 | Hasegawa et al. |
| 2015/0257704 A1 | 9/2015 | Courtney |
| 2015/0257850 A1 | 9/2015 | Sakamoto |
| 2015/0265152 A1 | 9/2015 | Feldman et al. |
| 2015/0265162 A1 | 9/2015 | Lavi et al. |
| 2015/0268039 A1 | 9/2015 | Tu et al. |
| 2015/0282737 A1 | 10/2015 | Tolkowsky et al. |
| 2015/0297373 A1 | 10/2015 | Schmitt et al. |
| 2015/0306361 A1 | 10/2015 | Feig et al. |
| 2015/0320317 A1 | 11/2015 | Furuichi et al. |
| 2015/0366534 A1 | 12/2015 | Nair et al. |
| 2015/0370229 A1 | 12/2015 | Adler et al. |
| 2015/0371382 A1 | 12/2015 | Furuichi et al. |
| 2016/0000406 A1 | 1/2016 | Petroff |
| 2016/0007838 A1 | 1/2016 | Ariura et al. |
| 2016/0008090 A1 | 1/2016 | Yokoi et al. |
| 2016/0015337 A1 | 1/2016 | Inoue et al. |
| 2016/0018211 A1 | 1/2016 | Adler et al. |
| 2016/0022208 A1 | 1/2016 | Gopinath |
| 2016/0022248 A1 | 1/2016 | Mori et al. |
| 2016/0070066 A1 | 3/2016 | Schmitt et al. |
| 2016/0073885 A1 | 3/2016 | Adler |
| 2016/0089203 A1 | 3/2016 | Shimizu et al. |
| 2016/0089547 A1 | 3/2016 | Shimizu et al. |

(56) References Cited

U.S. PATENT DOCUMENTS

| | | |
|---|---|---|
| 2016/0092749 A1 | 3/2016 | Sakamoto |
| 2016/0093049 A1 | 3/2016 | Kobayashi |
| 2016/0095577 A1 | 4/2016 | Itoh et al. |
| 2016/0113485 A1 | 4/2016 | Nishiyama et al. |
| 2016/0120408 A1 | 5/2016 | Bhagavatula et al. |
| 2016/0120492 A1 | 5/2016 | Honma et al. |
| 2016/0124134 A1 | 5/2016 | Zhu et al. |
| 2016/0153765 A1 | 6/2016 | Yamazaki et al. |
| 2016/0157803 A1 | 6/2016 | Keller |
| 2016/0166815 A1 | 6/2016 | Suehara |
| 2016/0171701 A1 | 6/2016 | Zagrodsky et al. |
| 2016/0171711 A1 | 6/2016 | Gopinath et al. |
| 2016/0174925 A1 | 6/2016 | Dascal et al. |
| 2016/0199017 A1 | 7/2016 | Shimizu et al. |
| 2016/0202417 A1 | 7/2016 | Bhagavatula et al. |
| 2016/0206208 A1 | 7/2016 | Yamamoto et al. |
| 2016/0206267 A1 | 7/2016 | Shimizu et al. |
| 2016/0206290 A1 | 7/2016 | Itoh et al. |
| 2016/0228071 A1 | 8/2016 | Wang et al. |
| 2016/0270766 A1 | 9/2016 | Kobayashi |
| 2016/0301189 A1 | 10/2016 | Cable et al. |
| 2016/0313507 A1 | 10/2016 | Adler et al. |
| 2016/0320170 A1 | 11/2016 | Yun et al. |
| 2016/0320564 A1 | 11/2016 | Murashima et al. |
| 2016/0335763 A1 | 11/2016 | Ambwani et al. |
| 2016/0335766 A1 | 11/2016 | Ambwani et al. |
| 2016/0338753 A1 | 11/2016 | Ryba et al. |
| 2016/0341538 A1 | 11/2016 | Tumlinson et al. |
| 2016/0349417 A1 | 12/2016 | Tearney et al. |
| 2016/0361018 A1 | 12/2016 | Courtney et al. |
| 2016/0370168 A1 | 12/2016 | Krol et al. |
| 2017/0014100 A1 | 1/2017 | Mori |
| 2017/0020392 A1 | 1/2017 | Xu |
| 2017/0024532 A1 | 1/2017 | Gopinath et al. |
| 2017/0024910 A1 | 1/2017 | Griffin et al. |
| 2017/0103520 A1 | 4/2017 | Gopinath et al. |
| 2017/0135663 A1 | 5/2017 | Dascal et al. |
| 2017/0140243 A1 | 5/2017 | Ambwani |
| 2017/0140531 A1 | 5/2017 | Dascal et al. |
| 2017/0140532 A1 | 5/2017 | Dascal et al. |
| 2017/0140560 A1 | 5/2017 | Kraus et al. |
| 2017/0143296 A1 | 5/2017 | Peterson et al. |
| 2017/0148161 A1 | 5/2017 | Griffin |
| 2017/0153439 A1 | 6/2017 | Horiike |
| 2017/0188831 A1 | 7/2017 | Adler et al. |
| 2017/0238809 A1 | 8/2017 | Tearney et al. |
| 2017/0261378 A1 | 9/2017 | Friedman et al. |
| 2017/0301084 A1 | 10/2017 | Gopinath |
| 2017/0309018 A1 | 10/2017 | Shalev et al. |
| 2017/0311806 A1 | 11/2017 | Comstock, II et al. |
| 2017/0325712 A1 | 11/2017 | Gopinath |
| 2017/0367581 A1 | 12/2017 | Tearney et al. |
| 2018/0003482 A1 | 1/2018 | Schmitt |
| 2018/0085095 A1 | 3/2018 | Hutchins et al. |
| 2018/0085170 A1 | 3/2018 | Gopinath |
| 2018/0125372 A1 | 5/2018 | Petroff et al. |
| 2018/0172424 A1 | 6/2018 | Comstock, II et al. |
| 2018/0177404 A1 | 6/2018 | Liu |
| 2018/0192957 A1 | 7/2018 | Schmitt et al. |
| 2018/0192983 A1 | 7/2018 | Dascal et al. |
| 2018/0225830 A1 | 8/2018 | Gopinath et al. |
| 2018/0226773 A1 | 8/2018 | Yun et al. |
| 2018/0275622 A1 | 9/2018 | Adler et al. |
| 2018/0293730 A1 | 10/2018 | Ambwani et al. |
| 2018/0306569 A1 | 10/2018 | Schmitt et al. |
| 2018/0344173 A1 | 12/2018 | Tu et al. |
| 2018/0344174 A9 | 12/2018 | Schmitt et al. |
| 2018/0353241 A1 | 12/2018 | Tu et al. |
| 2019/0029623 A1 | 1/2019 | Kunio |
| 2019/0035114 A1 | 1/2019 | Griffin et al. |
| 2019/0096063 A1 | 3/2019 | Ambwani |
| 2019/0099237 A1 | 4/2019 | Booker et al. |
| 2019/0220980 A1 | 7/2019 | Ambwani et al. |
| 2019/0274528 A1 | 9/2019 | Petroff et al. |
| 2019/0307412 A1 | 10/2019 | Dascal et al. |
| 2019/0365480 A1 | 12/2019 | Gopinath et al. |
| 2019/0380594 A1 | 12/2019 | Schmitt et al. |
| 2020/0129067 A1 | 4/2020 | Krug et al. |
| 2020/0142575 A1 | 5/2020 | Gopinath et al. |
| 2020/0167923 A1 | 5/2020 | Gopinath |
| 2020/0288950 A1 | 9/2020 | Petroff et al. |
| 2020/0355557 A1 | 11/2020 | Friedman et al. |
| 2020/0397405 A1 | 12/2020 | Hutchins et al. |
| 2021/0004955 A1 | 1/2021 | Ambwani et al. |
| 2021/0045622 A1 | 2/2021 | Petroff et al. |
| 2021/0177282 A1 | 6/2021 | Ahmed et al. |
| 2021/0267442 A1 | 9/2021 | Petersen et al. |
| 2021/0318111 A1 | 10/2021 | Vakoc et al. |
| 2022/0061670 A1 | 3/2022 | Petroff et al. |
| 2022/0142462 A1 | 5/2022 | Douk et al. |
| 2022/0142464 A1 | 5/2022 | Petroff et al. |
| 2022/0218206 A1 | 7/2022 | Petroff et al. |
| 2023/0000321 A1 | 1/2023 | Ughi et al. |
| 2023/0181016 A1 | 6/2023 | Ughi et al. |
| 2024/0000302 A1 | 1/2024 | Petroff et al. |
| 2024/0099564 A1 | 3/2024 | Petroff et al. |

FOREIGN PATENT DOCUMENTS

| | | |
|---|---|---|
| CN | 1780584 | 5/2006 |
| CN | 203801215 | 9/2014 |
| CN | 203801216 | 9/2014 |
| CN | 203805643 | 9/2014 |
| CN | 203805646 | 9/2014 |
| CN | 104126111 | 10/2014 |
| CN | 105019592 | 11/2015 |
| CN | 204826364 | 12/2015 |
| CN | 105662387 | 6/2016 |
| CN | 106570313 | 4/2017 |
| CN | 106650029 | 5/2017 |
| CN | 106805989 | 6/2017 |
| CN | 106974622 | 7/2017 |
| CN | 107115108 | 9/2017 |
| CN | 107133959 | 9/2017 |
| CN | 107233106 | 10/2017 |
| CN | 107745346 | 3/2018 |
| CN | 107978371 | 5/2018 |
| CN | 108022650 | 5/2018 |
| CN | 108038848 | 5/2018 |
| CN | 207464715 | 6/2018 |
| DE | 69738291 | 9/2008 |
| DE | 112016005442 | 8/2018 |
| DE | 112016005603 | 10/2018 |
| EP | 0883793 | 12/1998 |
| EP | 1685366 | 8/2006 |
| EP | 2505129 | 10/2012 |
| EP | 2803973 | 11/2014 |
| GB | 2512077 | 9/2014 |
| JP | 09168539 | 6/1997 |
| JP | 2000503237 | 3/2000 |
| JP | 2000097845 | 4/2000 |
| JP | 2000097846 | 4/2000 |
| JP | 2002214127 | 7/2002 |
| JP | 2005224399 | 8/2005 |
| JP | 2005230552 | 9/2005 |
| JP | 2005533610 | 11/2005 |
| JP | 2006271869 | 10/2006 |
| JP | 2007268131 | 10/2007 |
| JP | 20077267866 | 10/2007 |
| JP | 2008510586 | 4/2008 |
| JP | 2008523954 | 7/2008 |
| JP | 2009072291 | 4/2009 |
| JP | 4494203 | 6/2010 |
| JP | 2010167029 | 8/2010 |
| JP | 2010188138 | 9/2010 |
| JP | 2010533052 | 10/2010 |
| JP | 2011078550 | 4/2011 |
| JP | 2012147860 | 8/2012 |
| JP | 2012521852 | 9/2012 |
| JP | 2012205661 | 10/2012 |
| JP | 5093787 | 12/2012 |
| JP | 2012254211 | 12/2012 |
| JP | 2013500142 | 1/2013 |
| JP | 2013506136 | 2/2013 |

(56) References Cited

FOREIGN PATENT DOCUMENTS

| | | |
|---|---|---|
| JP | 2013521070 | 6/2013 |
| JP | 5269809 | 8/2013 |
| JP | 2014505496 | 3/2014 |
| JP | 5474190 | 4/2014 |
| JP | 2014180575 | 9/2014 |
| JP | 2014526283 | 10/2014 |
| JP | 5622796 | 11/2014 |
| JP | 5635149 | 12/2014 |
| JP | 5643315 | 12/2014 |
| JP | 2015013217 | 1/2015 |
| JP | 5689728 | 3/2015 |
| JP | 2015062638 | 4/2015 |
| JP | 5721721 | 5/2015 |
| JP | 2015518393 | 7/2015 |
| JP | 5778579 | 9/2015 |
| JP | 2015164660 | 9/2015 |
| JP | 5814860 | 11/2015 |
| JP | 2015532717 | 11/2015 |
| JP | 5856605 | 2/2016 |
| JP | 2016038329 | 3/2016 |
| JP | 2016508750 | 3/2016 |
| JP | 2016514996 | 5/2016 |
| JP | 5987025 | 9/2016 |
| JP | 5997232 | 9/2016 |
| JP | 2017524422 | 8/2017 |
| JP | 2018020158 | 2/2018 |
| JP | 2018507400 | 3/2018 |
| JP | 2018516147 | 6/2018 |
| JP | 2018527961 | 9/2018 |
| JP | 2018527995 | 9/2018 |
| JP | 2018192287 | 12/2018 |
| WO | 9732182 | 2/1997 |
| WO | 2004010856 | 2/2004 |
| WO | 2004096049 | 11/2004 |
| WO | 2005047813 | 5/2005 |
| WO | 2006022342 | 3/2006 |
| WO | 2006024015 | 3/2006 |
| WO | 2006068927 | 6/2006 |
| WO | 2008134449 | 11/2008 |
| WO | 2009009799 | 1/2009 |
| WO | 2009009802 | 1/2009 |
| WO | 2009010963 | 1/2009 |
| WO | 2010095370 | 8/2010 |
| WO | 2010113374 | 10/2010 |
| WO | 2011038010 | 3/2011 |
| WO | 2011059829 | 5/2011 |
| WO | 2012002302 | 1/2012 |
| WO | 2012064966 | 5/2012 |
| WO | 2013033415 | 3/2013 |
| WO | 2013126390 | 8/2013 |
| WO | 2014055908 | 4/2014 |
| WO | 2014142789 | 9/2014 |
| WO | 2014142815 | 9/2014 |
| WO | 2014149127 | 9/2014 |
| WO | 2014163601 | 10/2014 |
| WO | 2014175853 | 10/2014 |
| WO | 2015022760 | 2/2015 |
| WO | 2015044978 | 4/2015 |
| WO | 2015044982 | 4/2015 |
| WO | 2015044983 | 4/2015 |
| WO | 2015044984 | 4/2015 |
| WO | 2015074018 | 5/2015 |
| WO | 2015103277 | 7/2015 |
| WO | 2015136853 | 9/2015 |
| WO | 2015141136 | 9/2015 |
| WO | 2016168605 | 10/2016 |
| WO | WO-2016168605 A1 * | 10/2016 ............... A61B 1/07 |
| WO | 2016187218 | 11/2016 |
| WO | 2016187231 | 11/2016 |
| WO | 2016210132 | 12/2016 |
| WO | 2017011587 | 1/2017 |
| WO | 2017019626 | 2/2017 |
| WO | 2017019634 | 2/2017 |
| WO | 2015044987 | 3/2017 |
| WO | 2015045368 | 3/2017 |
| WO | 2017040484 | 3/2017 |
| WO | 2017097074 | 6/2017 |
| WO | 2017189942 | 11/2017 |
| WO | 2017200381 | 11/2017 |
| WO | 2019108598 | 6/2019 |
| WO | 2020223433 | 11/2020 |
| WO | 2020237024 | 11/2020 |
| WO | 2021222530 | 11/2021 |
| WO | 2023133355 | 7/2023 |
| WO | 2024081414 | 4/2024 |

OTHER PUBLICATIONS

Japanese Office Action dated Nov. 15, 2022 issued in related Japanese Application No. 2021-068226, with English translation.
International Preliminary Report on Patentability electronically transmitted to Applicant on Nov. 10, 2022, issued in related International Application No. PCT/US2021/029836.
Ghannam, M.T., et al. "Rheological Properties of Poly(dimethylsiloxane)". Industrial & Engineering Chemistry Research vol. 37, No. 4 (1998) pp. 1335-1340.
Berger, J.D. et al. "Widely tunable external cavity diode laser based on a MEMS electrostatic rotary actuator", OSA/OFC 2001, pp. TuJ2-1-TuJ2-3.
BlazePhotonics. "NL-2.4-800 Highly nonlinear PCF" technical specification sheet.
Buus, J. et al. "Tunable Lasers in Optical Networks", Journal Of Lightwave Technology, vol. 24, No. 1 (Jan. 2006), pp. 5-11.
Chang-Hasnain, C.J. "Tunable VCSEL", IEEE Journal On Selected Topics In Quantum Electronics, vol. 6, No. 6 (Nov./Dec. 2000), pp. 978-987.
Chang-Hasnain, C.J., "Progress And Prospects Of Long-Wavelength VCSELs", IEEE Optical Communications (Feb. 2003), pp. S30-S34.
Chinn, S.R. et al. "Optical coherence tomography using a frequency-tunable optical source", Optics Letters, vol. 22, No. 5 (Mar. 1, 1997), pp. 340-342.
Chinese Notice of Allowance and Supplementary Search Report dated Jan. 13, 2021 issued in corresponding Chinese Application No. 201680034490.4.
Chinese Office Action dated Aug. 28, 2019 issued in corresponding Chinese Application No. 201680034490.4, with English translation.
Chinese Office Action dated Feb. 27, 2019 issued in corresponding Chinese Application No. 201680034490.4, with English translation.
Chinese Office Action dated May 25, 2020 issued in corresponding Chinese Application No. 201680034490.4, with English summary.
European Office Action dated Feb. 4, 2020 issued in corresponding European Application No. 16780839.3.
NKT Photonics. "ESM-12 Single0mode 12 um core fiber" technical specification sheet.
NKT Photonics. "HC-1550-02 Hollow Core Photonic Bandgap Fiber" technical specification sheet.
NKT Photonics. "HC-800-02 Hollow Core Photonic Bandgap Fiber" technical specification sheet.
Ofili, E.O. et al. "Differential characterization of blood flow, velocity, and vascular resistance between proximal and distal normal epicardial human coronary arteries: Analysis by intracoronary Doppler spectral flow velocity", American Heart Journal (Jul. 1995), pp. 37-46.
Reed, W.A. et al. "Gradient-index fiber-optic microprobes for minimally invasive in vivo low-coherence interferometry", Optics Letters, vol. 27, No. 20 (Oct. 15, 2002), pp. 1794-1796.
Tearney, G.J. et al. "High-speed phase- and group-delay scanning with a grating-based phase control delay line", Optics Letters, vol. 22, No. 23 (Dec. 1, 1997), pp. 1811-1813.
Thorlabs, "Single Wavelength Graded-Index (GRIN) Lenses" Product Catalogue (online). Apr. 9, 2016 (retrieved Jan. 8, 2020). Retrieved from the Internet: URL: https://www.thorlabs.com/NewGroupPage9.cfm?ObjectGroup_ID=1209.
Von der Weid, J.P. et al. "On the Characterization of Optical Fiber Network Components with Optical Frequency Domain Reflectometry", Journal of Lightwave Technology, vol. 15, No. 7 (Jul. 1997), pp. 1131-1141.

(56) References Cited

OTHER PUBLICATIONS

Xi et al. "Diffractive catheter for ultrahigh-resolution spectral-domain volumetric OCT imaging", Optics Letters, vol. 39, No. 7 (Mar. 26, 2014), pp. 2016-2019.
Youngquist, R.C. et al."Optical coherence-domain reflectometry: a new optical evaluation technique", Optics Letters, vol. 12, No. 3 (Mar. 1987), pp. 158-160.
Yun, S.H. et al. "High-speed optical frequency-domain imaging", Optics Express, vol. 11, No. 22 (Nov. 3, 2003), pp. 2953-2963.
International Search Report and Written Opinion dated Apr. 14, 2023 issued in related International Application No. PCT/US2023/010508.
Atif et al. "Catheters for optical coherence tomography", Laser Physics Letters, vol. 8, No. 9, (Jul. 1, 2011), pp. 629-646.
Extended European Search Report dated Apr. 21, 2023 issued in related European Application No. 20810126.1.
Japanese Office Action dated Apr. 25, 2023 issued in corresponding Japanese Application No. 2021-514598, with English summary.
Summons To Attend Oral Proceedings dated Mar. 17, 2023 issued in related European Application No. 16842796.1.
Brezinski et al. "Optical Coherence Tomography: High-Resolution Imaging in Nontransparent Tissue", IEEE Journal of Selected Topics in Quantum Electronics, vol. 5, No. 4, Jul./Aug. 1999, pp. 1185-1192.
Extended European Search Report dated Mar. 21, 2023 issued in related European Application No. 20798343.8.
Extended European Search Report dated Jun. 8, 2022 issued in related European Application No. 21217738.0.
Extended European Search Report dated Apr. 21, 2022 issued in corresponding European Application No. 19862071.8.
Tran et al. "In vivo endoscopic optical coherence tomography by use of a rotational microelectromechanical system probe", Optics Letters, vol. 29 No. 11 (Jun. 1, 2004), p. 1236-1238.
Japanese Office Action dated Apr. 26, 2022 issued in corresponding Japanese Application No. 2021-068226, with English translation.
Japanese Office Action dated Sep. 26, 2023 issued in Japanese Application No. 2022164724, with English summary.
Japanese Office Action dated Mar. 16, 2021 issued in corresponding Japanese Application No. 2018-510969, with English language summary.
Japanese Office Action dated Feb. 21, 2023 issued in corresponding Japanese Application No. 2021-117103, with English summary.
Chinese Office Action dated Oct. 13, 2023 issued in Chinese Application No. 202110324448.9, with English summary.
European Office Action dated Apr. 21, 2021 issued in corresponding European Application No. 16842796.1.
International Search Report and Written Opinion dated Aug. 2, 2021 issued in corresponding International Application No. PCT/US2021/029836.
Extended European Search Report dated Nov. 26, 2021 issued in corresponding European Application No. 18883166.3.
International Preliminary Report on Patentability dated Nov. 11, 2021 issued in corresponding International Application No. PCT/US20/30616.
International Preliminary Report on Patentability dated Dec. 2, 2021 issued in related International Application No. PCT/US2020/033953.
Japanese Office Action dated Jan. 30, 2024 issued in corresponding Japanese Application No. 2021-514598, with English translation. (Re-submission of NPL submitted Feb. 8, 2024 with English summary only).
Japanese Office Action dated Jan. 30, 2024 issued in corresponding Japanese Application No. 2021-514598, with English summary.
Jung et al. "Handheld Optical Coherence Tomography Scanner for Primary Care Diagnostics", IEEE Transactions on Biomedical Engineering, Mar. 2011, vol. 58, No. 3, p. 741-744.
International Preliminary Report on Patentability dated Jul. 25, 2024 issued in International Application No. PCT/US2023/010508.
"Imaging System Includes Imaging Probe and Delivery Devices" Specification, Drawings, and Prosecution History of U.S. Appl. No. 15/751,570, filed Feb. 9, 2018, now U.S. Pat. No. 10,631,718, issued Apr. 28, 2020, by Christopher Petroff, et al.
Abozenadah, H., et al. Consumer Chemistry: How Organic Chemistry Impacts Our Lives. CC BY-NC-SA. Available at: https://wou.edu/chemistry/courses/online-chemistry-textbooks/ch105-consumer-chemistry/ (2017).
Athanasiou, L.S. et al. "Fully automated lumen segmentation of intracoronary optical coherence tomography images", Medical Imaging 2017, vol. 10133, pp. 1013321-1-1013321-7. Downloaded from the internet on Mar. 6, 2017: http://proceedings.spiedigitallibrary.org/.
Extended European Search Report dated Apr. 9, 2019 issued in corresponding European Application No. 16842796.1.
Extended European Search Report dated Jan. 2, 2019 issued in corresponding European Application No. 16780839.3.
International Preliminary Report on Patentability dated Jun. 11, 2020 issued in corresponding International Application No. PCT/US2018/062766.
International Preliminary Report on Patentability dated Mar. 15, 2018 issued in corresponding International Application No. PCT/us2016/049415.
International Preliminary Report on Patentability dated Oct. 17, 2017 issued in corresponding International Application No. PCT/US2016/027764.
International Search Report & Written Opinion dated Feb. 11, 2019, issued in related International Application No. PCT/US2018/062766.
International Search Report and Written Opinion dated Jan. 31, 2020 issued in corresponding International Application No. PCT/US2019/051447.
International Search Report and Written Opinion dated Jul. 30, 2020 issued in corresponding International Application No. PCT/US20/33953.
International Search Report and Written Opinion dated Sep. 14, 2020 issued in corresponding International Application No. PCT/US20/30616.
International Search Report dated Jul. 14, 2016 issued in corresponding International Application No. PCT/US2016/027764.
International Search Report dated Nov. 7, 2016, issued in corresponding International Application No. PCT/US2016/049415.
Japanese Office Action dated Mar. 31, 2020 issued in corresponding Japanese Application No. 2018-505582, with English translation.
Japanese Office Action dated Nov. 17, 2020 issued in corresponding Japanese Application No. 2018-505582, with English translation.
Japanese Office Action dated Sep. 15, 2020 issued in corresponding Japanese Application No. 2018-510969, with English language summary.
Fermann, M.E. et al. "Ultrawide tunable Er solition fiber laser amplified in Yb-doped fiber", Optics Letters, vol. 24, No. 20 (Oct. 15, 1999), pp. 1428-1430.
Focabex, "Core Structure of Optical Cables" Article (online). Feb. 1, 2002 (retrieved Jan. 8, 2020). Retrieved from the Internet: URL: http://www.focabex.com/library-n/CORE-STRUCTURE-OF-OPTICAL-FIBER-CABLES.pdf.
Golubovic, B. et al. "Optical frequency-domain reflectometry using rapid wavelength tuning of a Cr4+:forsterite laser", Optics Letters, vol. 22, No. 22 (Nov. 15, 1997), pp. 1704-1706.
Harris Jr., J.S. "Tunable Long-Wavelength Vertical-Cavity Lasers: The Engine of Next Generation Optical Networks?", IEEE Journal On Selected Topics In Quantum Electronics, vol. 6, No. 6 (Nov./Dec. 2000), pp. 1145-1160.
Introduction to silicone fluids (https://www.clearcoproducts.com/introduction-to-silicone-fluids.html), retrieved Sep. 24, 2020.
Kakuta, T. et al. "Behavior of optical fibers under heavy irradiation", Fusion Engineering And Design, vol. 41 (1998), pp. 201-205.
Madigan, Jeremy. "Vascular access: guide catheter selection, usage, and compatibility." Interventional Neuroradiology, Springer, London (2014), pp. 27-38.
Meuwissen, M. et al. "Role of Variability in Microvascular Resistance onFractional Flow Reserve and Coronary Blood Flow Velocity Reserve in Intermediate Coronary Lesions", Circulation, 103

(56) References Cited

OTHER PUBLICATIONS (2001), pp. 184-187 [online—retrieved on Mar. 7, 2018]. Retrieved from the Internet URL: http://circ.ahajournals.org/content/103/2/184.
Zheng, W. "Optic Lenses Manufactured on Fiber Ends", IEEE, 978-1-4673-7732-4/15, 2015, pp. 1-10.
Office Action dated Jun. 4, 2024 issued in European Application No. 19862071.8.

* cited by examiner

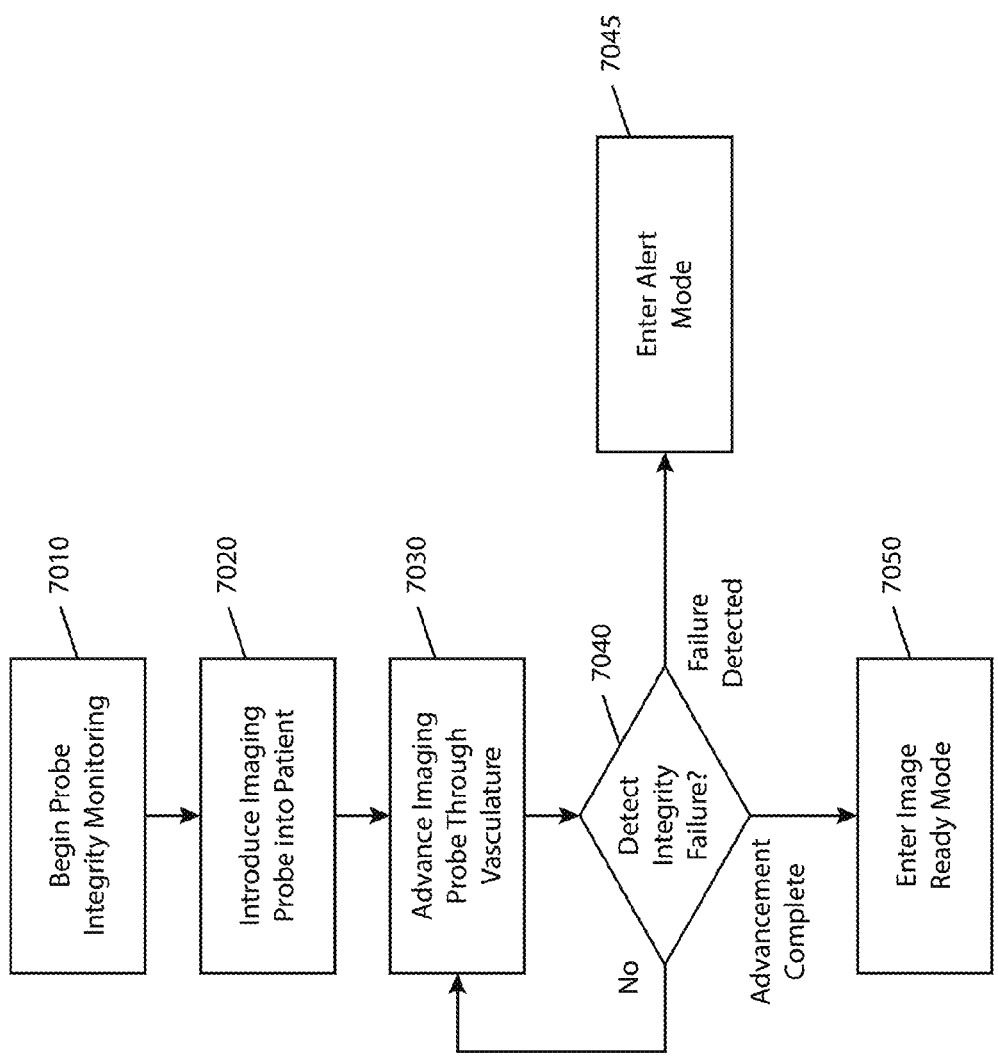

IMAGING SYSTEM WITH OPTICAL PATHWAY

RELATED APPLICATIONS

This application claims priority to U.S. Provisional Application Ser. No. 62/732,114 titled "Imaging System with Optical Pathway", filed Sep. 17, 2018, the content of which is incorporated by reference in its entirety.

This application claims priority to U.S. Provisional Application Ser. No. 62/840,450, titled "Imaging Probe with Fluid Pressurization Element", filed Apr. 30, 2019, the content of which is incorporated by reference in its entirety.

This application claims priority to U.S. Provisional Application Ser. No. 62/850,945, titled "OCT-Guided Treatment of a Patient", filed May 21, 2019, the content of which is incorporated by reference in its entirety.

This application is related to U.S. Provisional Application Ser. No. 62/148,355, titled "Micro-Optic Probes for Neurology", filed Apr. 16, 2015, the content of which is incorporated by reference in its entirety.

This application is related to U.S. Provisional Application Ser. No. 62/322,182, titled "Micro-Optic Probes for Neurology", filed Apr. 13, 2016, the content of which is incorporated by reference in its entirety.

This application is related to International PCT Patent Application Serial Number PCT/US2016/027764, titled "Micro-Optic Probes for Neurology" filed Apr. 15, 2016, Publication Number WO 2016/168605, published Oct. 20, 2016, the content of which is incorporated by reference in its entirety.

This application is related to U.S. patent application Ser. No. 15/566,041, titled "Micro-Optic Probes for Neurology", filed Apr. 15, 2016, United States Publication Number 2018-0125372, published May 10, 2018, the content of which is incorporated by reference in its entirety.

This application is related to U.S. Provisional Application Ser. No. 62/212,173, titled "Imaging System Includes Imaging Probe and Delivery Devices", filed Aug. 31, 2015, the content of which is incorporated by reference in its entirety.

This application is related to U.S. Provisional Application Ser. No. 62/368,387, titled "Imaging System Includes Imaging Probe and Delivery Devices", filed Jul. 29, 2016, the content of which is incorporated by reference in its entirety.

This application is related to International PCT Patent Application Serial Number PCT/US2016/049415, titled "Imaging System Includes Imaging Probe and Delivery Devices", filed Aug. 30, 2016, Publication Number WO 2017/040484, published Mar. 9, 2017, the content of which is incorporated by reference in its entirety.

This application is related to U.S. patent application Ser. No. 15/751,570, titled "Imaging System Includes Imaging Probe and Delivery Devices", filed Feb. 9, 2018, United States Publication Number 2019-0274528, published Sep. 12, 2019, the content of which is incorporated by reference in its entirety.

This application is related to U.S. Provisional Application Ser. No. 62/591,403, titled "Imaging System", filed Nov. 28, 2017; the content of which is incorporated by reference in its entirety.

This application is related to U.S. Provisional Application Ser. No. 62/671,142, titled "Imaging System", filed May 14, 2018; the content of which is incorporated by reference in its entirety.

This application is related to International PCT Patent Application Serial Number PCT/US2018/062766, titled "Imaging System", filed Nov. 28, 2018; Publication Number WO 2019/108598, published Jun. 6, 2019, the content of which is incorporated by reference in its entirety.

FIELD OF THE INVENTION

The present invention relates generally to imaging systems, and in particular, intravascular imaging systems including imaging probes and delivery devices.

BACKGROUND

Imaging probes have been commercialized for imaging various internal locations of a patient, such as an intravascular probe for imaging a patient's heart. Current imaging probes are limited in their ability to reach certain anatomical locations due to their size and rigidity. Current imaging probes are inserted over a guidewire, which can compromise their placement and limit use of one or more delivery catheters through which the imaging probe is inserted. There is a need for imaging systems that include probes with reduced diameter, high flexibility and ability to be advanced to a patient site to be imaged without a guidewire, as well as systems with one or more delivery devices compatible with these improved imaging probes.

SUMMARY

According to an aspect of the present inventive concepts, an imaging system for a patient comprising: an imaging probe, comprising: an elongate shaft comprising a proximal end, a distal portion, and a lumen extending between the proximal end and the distal portion; a rotatable optical core comprising a proximal end and a distal end, and at least a portion of the rotatable optical core is positioned within the lumen of the elongate shaft; and an optical assembly positioned proximate the distal end of the rotatable optical core, the optical assembly configured to direct light to tissue and collect reflected light from the tissue; an imaging assembly constructed and arranged to optically couple to the imaging probe, the imaging assembly configured to emit light into the imaging probe and receive the reflected light collected by the optical assembly.

In some embodiments, the system further comprises a second shaft surrounding the imaging probe, and the imaging probe is slidingly received within the second shaft. The elongate shaft can comprise a distal end, and the distal end of the rotatable optical core can extend beyond the distal end of the elongate shaft. The rotatable optical core can further comprise a distal portion, and the system can further comprise a strain relief surrounding the distal portion of the rotatable optical core. The optical assembly can be positioned within the second shaft and outside of the elongate shaft. The optical assembly can comprise an outer diameter that can be greater than the diameter of the lumen of the elongate shaft. The optical assembly can comprise a GRIN lens. The space between the optical assembly and the second shaft can be filled with one or more gases. The optical assembly can comprise a GRIN lens, a reflector, and a tube, and a chamber can be positioned within the tube between the GRIN lens and the reflector. The chamber can be filled with one or more gases.

In some embodiments, the optical assembly comprises a GRIN lens. The GRIN lens can comprise a center portion with a first refractive index, and the rotatable optical core can comprise a center portion with a second refractive index, and the first refractive index can be greater than the second refractive index. The first refractive index and the second refractive index can be configured to provide a known back-reflection. The GRIN lens can comprise an angled distal end configured as a reflector. The reflector can be configured to provide total internal reflection. The reflector can comprise a metallicized reflector. The GRIN lens can further comprise a second angled surface. The second angled surface can comprise a surface at an angle of approximately 5°. The reflector can comprise a convex surface. The convex surface can comprise a cylindrical surface. The convex surface can comprise a single radius of curvature. The angled distal end can comprise an angle less than or equal to 47°. The angled distal end can comprise an angle less than 45°. The angled distal end can comprise an angle of approximately 40°. The angled distal end can comprise an angle not equal to 45°.

In some embodiments, the optical assembly comprises a first component comprising a GRIN lens and a second component comprising a reflector. The GRIN lens can comprise an angled distal end. The angled distal end can comprise a surface at an angle of greater than 5°. The angled distal end can be configured to minimize back reflection. The reflector can comprise a concave proximal surface. The concave proximal surface can comprise a cylindrical surface. The concave proximal surface can comprise a single radius of curvature. The optical assembly can comprise a tube connecting the GRIN lens to the reflector.

In some embodiments, the optical assembly is configured to produce an identifiable back reflection. The identifiable back reflection can comprise a set of back-reflections. The imaging assembly can be configured to detect the identifiable back reflection. The system can be configured such that a change in the identifiable back reflection correlates to an undesired state of the rotatable optical core. The change in the identifiable back reflection can comprise a loss of the identifiable back reflection. The undesired state can comprise a break in the rotatable optical core. The system can be configured to enter an alert mode if an undesired state of the rotatable optical core is detected. The imaging assembly can be configured to detect the identifiable back reflection when the rotatable optical core is not spinning. The imaging assembly can be configured to detect the identifiable back reflection when the imaging probe is being advanced within the patient.

In some embodiments, the imaging assembly comprises a balanced interferometer that is optically attached to a reference path and a sample path, and the reference path includes at least one reference segment; and the sample path includes the rotatable optical core and the optical assembly. The reference path can include an optical switch. The system can comprise at least two reference segments, and the optical switch can optically switch between a first reference segment and a second reference segment. The first reference segment can comprise a length that is greater than the length of the second reference segment. The imaging probe can comprise a first imaging probe including a rotatable optical core with a first length, and the system can comprise a second imaging probe comprising a rotatable optical core with a second length, and the first length and the second length can comprise different lengths. The difference between the first length and the second length can be equal to the difference in length between the first reference segment and the second reference segment. The at least one reference segment can comprise a first reference segment configured to approximate optical properties of the rotatable optical core. The first reference segment can be configured to approximate the numerical aperture (NA) of the rotatable optical core. The first reference segment can be configured to approximate the dispersion of the rotatable optical core. The first reference segment can be configured to approximate the dispersion wavelength and/or the dispersion slope of the rotatable optical core. The reference path can comprise a transmissive reference path. The transmissive reference path can comprise a length twice the length of the sample path. The balanced interferometer can comprise a reference output and a reference input. The reference path can comprise a switching assembly configured to switch between two or more unique reference segments. The switching assembly can comprise an input switch and an output switch. The switching assembly can comprise an input switch and a passive coupler. The rotatable optical core can comprise a first rotatable optical core, and the system can comprise a second probe with a second rotatable optical core, and the two or more unique reference segments can comprise a first reference segment with one or more optical properties that match optical properties of the first rotational optical core, and a second reference segment with one or more optical properties that match optical properties of the second rotational optical core.

In some embodiments, the system further comprises a rotation assembly constructed and arranged to optically and mechanically connect to the imaging probe, and to rotate the optical assembly; and a retraction assembly constructed and arranged to mechanically connect to the imaging probe, and to retract the optical assembly and the elongate shaft in unison. The imaging probe can comprise a proximal connector; and the retraction assembly can comprise a pullback module and a linkage assembly; and the pullback module can be configured to attach to the elongate shaft of the imaging probe and to retract the imaging probe, and the system can further comprise a patient interface module configured to: attach to the proximal connector; attach to the linkage assembly; provide a retraction force to the pullback module via the linkage assembly; and rotate the rotatable optical core. The pullback module can comprise a first discrete component that can be positioned at a first location, and the patient interface module can further comprise a second discrete component that can be positioned at a second location that can be remote from the first location. The imaging probe enters the patient at a vascular access site, and the first location can comprise a location proximate the vascular access site. The second location can be at least 15 cm remote from the first location. The first location can be within 30 cm of the vascular access site. The retraction assembly can comprise a linkage assembly including a sheath with a distal end, a puller, and a motive element, and the motive element can apply a pullback force to the puller via the linkage assembly thereby causing the puller to move proximally relative to the distal end of the sheath. The imaging probe can comprise a proximal portion and a proximal connector within the proximal portion; and the system can further comprise a connector module including a housing, a first connector, and a linkage, and the housing can surround the proximal portion of the imaging probe, and the proximal connector can be attached to the housing, and the linkage can be attached to the elongate shaft of the imaging probe, and the first connector can slidingly receive the linkage, and the system can further comprise a patient interface module, including a second connector that attaches to the first connector and a third connector that attaches to the proximal connector, and the patient interface module can retract the linkage of the connector module, and the housing of the connector module can surround the retracted portion of the imaging probe, and the patient interface module can rotate the rotatable optical core. The rotation assembly can rotate the optical assembly and the rotatable optical core in unison. The imaging probe can comprise a proximal end including a connector, and the rotation assembly can comprise a rotary joint that operably engages the connector, and the rotary joint can rotate the rotatable optical core via the connector. The retraction assembly can comprise a connector assembly configured to attach to a reference point. The reference point can comprise a patient introduction device and/or a surgical table.

In some embodiments, the rotatable optical core comprises a non-tapered fiber.

According to another aspect of the present inventive concepts, a method of calibrating an imaging system comprising: emitting light from an imaging assembly to an attached imaging probe, the imaging probe comprising: a rotatable optical core comprising a proximal end and a distal end, and an optical assembly positioned proximate the distal end of the rotatable optical core, the optical assembly configured to direct light to tissue and collect reflected light from the tissue; receiving light from the imaging probe with the imaging assembly, including light from a back-reflection at the interface of the rotatable optical core and the optical assembly, determining the distance from the imaging assembly to the interface based on the received light from the back-reflection, and calibrating the imaging system based on the measured distance.

In some embodiments, the rotatable optical core is not rotated during the calibration.

In some embodiments, the calibrating comprises adjusting the length of a reference path. The imaging assembly can comprise a delay line. The delay line can comprise a step size of no more than 15 pm.

In some embodiments, the system further comprises a rotation assembly constructed and arranged to optically and mechanically connect to the imaging probe, and to rotate the optical assembly. The imaging probe can further comprise a connector configured to optically connect the proximal end of the rotatable optical core to the rotation assembly. The optical connection can comprise a physical connection. The connector can be configured to minimize vibrational energy as the physical connection. The connector can comprise a shaft surrounding at least a portion of the rotatable optical core. The shaft can comprise a flexible shaft. The shaft can be configured to dissipate vibration energy. The shaft can comprise a wall thickness of no more than 0.006". The shaft can comprise one, two, or more materials selected from the group consisting of: a plastic material; a rubber material; a polymer material; polyimide; and combinations thereof. The shaft can comprise a diameter of no more than 0.025". The shaft can comprise a length of no more than 25 mm.

The technology described herein, along with the attributes and attendant advantages thereof, will best be appreciated and understood in view of the following detailed description taken in conjunction with the accompanying drawings in which representative embodiments are described by way of example.

BRIEF DESCRIPTION OF THE DRAWINGS

FIG. 7 illustrates a flow chart of a diagnostic method using a control surface, consistent with the present inventive concepts.

DETAILED DESCRIPTION OF THE DRAWINGS

Figure 1:
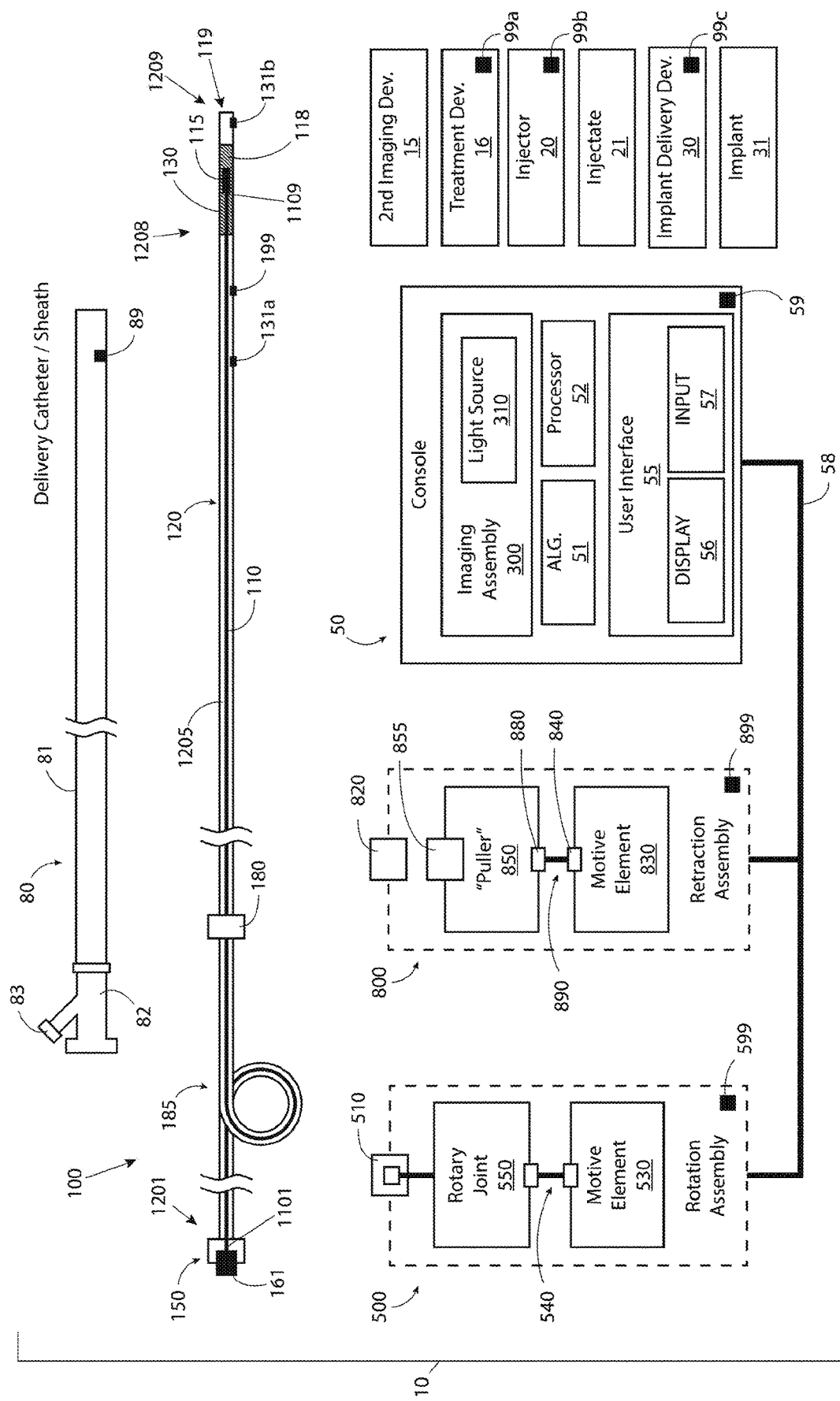
FIG. 1 illustrates a schematic view of an imaging system comprising an imaging probe and independent retraction and rotation assemblies, consistent with the present inventive concepts.

Reference will now be made in detail to the present embodiments of the technology, examples of which are illustrated in the accompanying drawings. Similar reference numbers may be used to refer to similar components. However, the description is not intended to limit the present disclosure to particular embodiments, and it should be construed as including various modifications, equivalents, and/or alternatives of the embodiments described herein.

It will be understood that the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") when used herein, specify the presence of stated features, integers, steps, operations, elements, and/or components, but do not preclude the presence or addition of one or more other features, integers, steps, operations, elements, components, and/or groups thereof.

It will be further understood that, although the terms first, second, third etc. may be used herein to describe various limitations, elements, components, regions, layers and/or sections, these limitations, elements, components, regions, layers and/or sections should not be limited by these terms.

These terms are only used to distinguish one limitation, element, component, region, layer or section from another limitation, element, component, region, layer or section. Thus, a first limitation, element, component, region, layer or section discussed below could be termed a second limitation, element, component, region, layer or section without departing from the teachings of the present application.

It will be further understood that when an element is referred to as being "on", "attached", "connected" or "coupled" to another element, it can be directly on or above, or connected or coupled to, the other element, or one or more intervening elements can be present. In contrast, when an element is referred to as being "directly on", "directly attached", "directly connected" or "directly coupled" to another element, there are no intervening elements present. Other words used to describe the relationship between elements should be interpreted in a like fashion (e.g. "between" versus "directly between," "adjacent" versus "directly adjacent," etc.).

It will be further understood that when a first element is referred to as being "in", "on" and/or "within" a second element, the first element can be positioned: within an internal space of the second element, within a portion of the second element (e.g. within a wall of the second element); positioned on an external and/or internal surface of the second element; and combinations of one or more of these.

As used herein, the term "proximate" shall include locations relatively close to, on, in and/or within a referenced component or other location.

Spatially relative terms, such as "beneath," "below," "lower," "above," "upper" and the like may be used to describe an element and/or feature's relationship to another element(s) and/or feature(s) as, for example, illustrated in the figures. It will be further understood that the spatially relative terms are intended to encompass different orientations of the device in use and/or operation in addition to the orientation depicted in the figures. For example, if the device in a figure is turned over, elements described as "below" and/or "beneath" other elements or features would then be oriented "above" the other elements or features. The device can be otherwise oriented (e.g. rotated 90 degrees or at other orientations) and the spatially relative descriptors used herein interpreted accordingly.

The terms "reduce", "reducing", "reduction" and the like, where used herein, are to include a reduction in a quantity, including a reduction to zero. Reducing the likelihood of an occurrence shall include prevention of the occurrence.

The term "and/or" where used herein is to be taken as specific disclosure of each of the two specified features or components with or without the other. For example, "A and/or B" is to be taken as specific disclosure of each of (i) A, (ii) B and (iii) A and B, just as if each is set out individually herein.

In this specification, unless explicitly stated otherwise, "and" can mean "or," and "or" can mean "and." For example, if a feature is described as having A, B, or C, the feature can have A, B, and C, or any combination of A, B, and C. Similarly, if a feature is described as having A, B, and C, the feature can have only one or two of A, B, or C.

As used herein, when a quantifiable parameter is described as having a value "between" a first value X and a second value Y, it shall include the parameter having a value of: at least X, no more than Y, and/or at least X and no more than Y. For example, a length of between 1 and 10 shall include a length of at least 1 (including values greater than 10), a length of less than 10 (including values less than 1), and/or values greater than 1 and less than 10.

The expression "configured (or set) to" used in the present disclosure may be used interchangeably with, for example, the expressions "suitable for", "having the capacity to", "designed to", "adapted to", "made to" and "capable of" according to a situation. The expression "configured (or set) to" does not mean only "specifically designed to" in hardware. Alternatively, in some situations, the expression "a device configured to" may mean that the device "can" operate together with another device or component.

As described herein, "room pressure" shall mean pressure of the environment surrounding the systems and devices of the present inventive concepts. Positive pressure includes pressure above room pressure or simply a pressure that is greater than another pressure, such as a positive differential pressure across a fluid pathway component such as a valve. Negative pressure includes pressure below room pressure or a pressure that is less than another pressure, such as a negative differential pressure across a fluid component pathway such as a valve. Negative pressure can include a vacuum but does not imply a pressure below a vacuum. As used herein, the term "vacuum" can be used to refer to a full or partial vacuum, or any negative pressure as described hereabove.

The term "diameter" where used herein to describe a non-circular geometry is to be taken as the diameter of a hypothetical circle approximating the geometry being described. For example, when describing a cross section, such as the cross section of a component, the term "diameter" shall be taken to represent the diameter of a hypothetical circle with the same cross sectional area as the cross section of the component being described.

The terms "major axis" and "minor axis" of a component where used herein are the length and diameter, respectively, of the smallest volume hypothetical cylinder which can completely surround the component.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination. For example, it will be appreciated that all features set out in any of the claims (whether independent or dependent) can be combined in any given way.

It is to be understood that at least some of the figures and descriptions of the invention have been simplified to focus on elements that are relevant for a clear understanding of the invention, while eliminating, for purposes of clarity, other elements that those of ordinary skill in the art will appreciate may also comprise a portion of the invention. However, because such elements are well known in the art, and because they do not necessarily facilitate a better understanding of the invention, a description of such elements is not provided herein.

Terms defined in the present disclosure are only used for describing specific embodiments of the present disclosure and are not intended to limit the scope of the present disclosure. Terms provided in singular forms are intended to include plural forms as well, unless the context clearly indicates otherwise. All of the terms used herein, including technical or scientific terms, have the same meanings as those generally understood by an ordinary person skilled in the related art, unless otherwise defined herein. Terms defined in a generally used dictionary should be interpreted as having meanings that are the same as or similar to the contextual meanings of the relevant technology and should not be interpreted as having ideal or exaggerated meanings, unless expressly so defined herein. In some cases, terms defined in the present disclosure should not be interpreted to exclude the embodiments of the present disclosure.

Provided herein are systems for use in a patient to create an image of the patient's anatomy. The image can comprise a two-dimensional and/or three-dimensional image of the patient's anatomy, and it can further include an image of one or more devices positioned proximate the patient's anatomy being imaged. The systems include an imaging probe, a rotation assembly, and a retraction assembly. The imaging probe collects image data from a patient site and includes an elongate shaft with a proximal end and a distal portion, with a lumen extending therebetween. A rotatable optical core is positioned within the elongate shaft lumen and an optical assembly is positioned in the elongate shaft distal portion. The optical assembly directs light to tissue at the patient site and collects reflected light from the tissue. The rotation assembly connects to the imaging probe and rotates the optical assembly. The retraction assembly connects to the imaging probe and retracts the optical assembly and the elongate shaft in unison.

Referring now to FIG. 1, a schematic view of an imaging system comprising an imaging probe and independent retraction and rotation assemblies is illustrated, consistent with the present inventive concepts. Imaging system 10 is constructed and arranged to collect image data and produce one or more images based on the recorded data, such as when imaging system 10 comprises an Optical Coherence Tomography (OCT) imaging system constructed and arranged to collect image data of an imaging location (e.g. a segment of a blood vessel, such as during a pullback procedure). Imaging system 10 comprises a catheter-based probe, imaging probe 100, as well as a rotation assembly 500 and a retraction assembly 800, each of which can operably attach to imaging probe 100. Imaging system 10 can further comprise console 50 which is configured to operably connect to imaging probe 100, such as via rotation assembly 500 and/or retraction assembly 800. Imaging probe 100 can be introduced into a conduit of the patient, such as a blood vessel or other conduit of the patient, using one or more delivery catheters, for example delivery catheter 80 shown. Additionally or alternatively, imaging probe 100 can be introduced through an introducer device, such as an endoscope, arthroscope, balloon dilator, or the like. In some embodiments, imaging probe 100 is configured to be introduced into a conduit selected from the group consisting of: an artery; a vein; an artery within or proximate the heart; a vein within or proximate the heart; an artery within or proximate the brain; a vein within or proximate the brain; a peripheral artery; a peripheral vein; through a natural body orifice into a conduit, such as the esophagus; through a surgically created orifice into a body cavity, such as the abdomen; and combinations of one or more of these. Imaging system 10 can further comprise multiple imaging devices, second imaging device 15 shown. Imaging system 10 can further comprise a device configured to treat the patient, treatment device 16. Imaging system 10 can further comprise a fluid injector, such as injector 20, which can be configured to inject one or more fluids, such as a flushing fluid, an imaging contrast agent (e.g. a radiopaque contrast agent, hereinafter "contrast") and/or other fluid, such as injectate 21 shown. Imaging system 10 can further comprise an implant, such as implant 31, which can be implanted in the patient via a delivery device, such as an implant delivery device 30 and/or delivery catheter 80.

In some embodiments, imaging probe 100 and/or another component of imaging system 10 can be of similar construction and arrangement to the similar components described in applicant's co-pending U.S. patent application Ser. No. 15/566,041, titled "Micro-Optic Probes for Neurology", filed Oct. 12, 2017; the content of which is incorporated herein by reference in its entirety for all purposes. Imaging probe 100 can be constructed and arranged to collect image data from a patient site, such as an intravascular cardiac site, an intracranial site, or other site accessible via the vasculature of the patient. In some embodiments, imaging system 10 can be of similar construction and arrangement to the similar systems and their methods of use described in applicant's co-pending U.S. patent application Ser. No. 15/751,570, titled "Imaging System includes Imaging Probe and Delivery Devices", filed Feb. 9, 2018; the content of which is incorporated herein by reference in its entirety for all purposes.

Delivery catheter 80 comprises an elongate shaft, shaft 81, with a lumen therethrough, and a connector 82 positioned on its proximal end. Connector 82 can comprise a Touhy or valved connector, such as a valved connector configured to prevent fluid egress from the associated delivery catheter 80 (with and/or without a separate shaft positioned within the connector 82). Connector 82 can comprise a port 83, such as a port constructed and arranged to allow introduction of fluid into delivery catheter 80 and/or for removing fluids from delivery catheter 80. In some embodiments, a flushing fluid, as described herebelow, is introduced via one or more ports 83, such as to remove blood or other undesired material from locations proximate optical assembly 115 (e.g. from a location proximal to optical assembly 115 to a location distal to optical assembly 115). Port 83 can be positioned on a side of connector 82 and can include a luer fitting and a cap and/or valve. Shafts 81, connectors 82, and ports 83 can each comprise standard materials and be of similar construction to commercially available introducers, guide catheters, diagnostic catheters, intermediate catheters and microcatheters used in interventional procedures. Delivery catheter 80 can comprise a catheter configured to deliver imaging probe 100 to an intracerebral location, an intracardiac location; and/or another location within a patient.

Imaging system 10 can comprise two or more delivery catheters 80, such as three or more delivery catheters 80. Multiple delivery catheters 80 can comprise at least a vascular introducer, and other delivery catheters 80 that can be inserted into the patient therethrough, after the vascular introducer is positioned through the skin of the patient. Two or more delivery catheters 80 can collectively comprise sets of inner diameters (IDs) and outer diameters (ODs) such that a first delivery catheter 80 slidingly receives a second delivery catheter 80 (e.g. the second delivery catheter OD is less than or equal to the first delivery catheter ID), and the second delivery catheter 80 slidingly receives a third delivery catheter 80 (e.g. the third delivery catheter OD is less than or equal to the second delivery catheter ID), and so on. In these configurations, the first delivery catheter 80 can be advanced to a first anatomical location, the second delivery catheter 80 can be advanced through the first delivery catheter to a second anatomical location distal or otherwise remote (hereinafter "distal") to the first anatomical location, and so on as appropriate, using sequentially smaller diameter delivery catheters 80. In some embodiments, delivery catheters 80 can be of similar construction and arrangement to the similar components described in applicant's co-pending U.S. patent application Ser. No. 15/751,570, titled "Imaging System includes Imaging Probe and Delivery Devices", filed Feb. 9, 2018; the content of which is incorporated herein by reference in its entirety for all purposes.

Imaging probe 100 comprises an elongate body, comprising one or more elongate shafts and/or tubes, elongate shaft 120 herein. Shaft 120 comprises a proximal end 1201, distal end 1209, and a lumen 1205 extending therebetween. In some embodiments, lumen 1205 can include multiple coaxial lumens within the one or more elongate shafts 120, such as one or more lumens abutting each other to define a single lumen 1205. In some embodiments, at least a portion of shaft 120 comprises a torque shaft. In some embodiments, a portion of shaft 120 comprises a braided construction. Shaft 120 operably surrounds a rotatable optical fiber, optical core 110 (e.g. optical core 110 is positioned within lumen 1205), comprising a proximal end 1101 and a distal end 1109. Optical core 110 can comprise a dispersion shifted optical fiber, such as a depressed cladding dispersion shifted fiber. Shaft 120 further comprises a distal portion 1208, including a transparent window, window 130 (e.g. a window that is relatively transparent to the one or more frequencies of light transmitted through optical core 110). An optical assembly, optical assembly 115, is operably attached to the distal end 1109 of optical core 110. Optical assembly 115 is positioned within window 130 of shaft 120. A connector assembly, connector assembly 150, is positioned on the proximal end of shaft 120. Connector assembly 150 operably attaches imaging probe 100 to rotation assembly 500, as described herein. Connector assembly 150 surrounds and operably attaches to an optical connector 161, fixedly attached to the proximal end of optical core 110. A second connector, pullback connector 180, is positioned on shaft 120. Connector 180 can be removably attached and/or adjustably positioned along the length of shaft 120. Connector 180 can be positioned along shaft 120, such as by an operator, proximate the proximal end of delivery catheter 80 after imaging probe 100 has been inserted into a patient via delivery catheter 80. Shaft 120 can comprise a portion between connector assembly 150 and the placement location of connector 180 that accommodates slack in shaft 120, a proximal portion of shaft 120 (e.g. a proximal portion of imaging probe 100), service loop 185.

Imaging probe 100 can comprise one or more visualizable markers along its length (e.g. along shaft 120), markers 131*a-b* shown (marker 131 herein). Marker 131 can comprise markers selected from the group consisting of: radiopaque markers; ultrasonically reflective markers; magnetic markers; ferrous material; and combinations of one or more of these. In some embodiments, marker 131 comprises a marker positioned at a location (e.g. a location within and/or at least proximate distal portion 1208) to assist an operator of imaging system 10 in performing a pullback procedure, such as to cause tip 119 to be positioned at a location distal to the proximal end of an implant after the pullback is completed (e.g. so that imaging probe 100 can be safely advanced through the implant after the pullback).

In some embodiments, imaging probe 100 includes a viscous dampening material, gel 118, positioned within shaft 120 and surrounding optical assembly 115 and a distal portion of optical core 110 (e.g. a gel injected or otherwise installed in a manufacturing process). Gel 118 can comprise anon-Newtonian fluid, for example a shear-thinning fluid. In some embodiments, gel 118 comprises a static viscosity of greater than 500 centipoise, and a shear viscosity that is less than the static viscosity. In these embodiments, the ratio of static viscosity to shear viscosity of gel 118 can be between 1.2:1 and 100:1. Gel 118 can comprise a gel as described in reference to applicant's co-pending U.S. patent application Ser. No. 15/566,041, titled "Micro-Optic Probes for Neurology", filed Oct. 12, 2017, and applicant's co-pending International PCT Patent Application Serial Number PCT/US2018/062766, titled "Imaging System", filed Nov. 28, 2018, the content of each of which is incorporated herein by reference in its entirety for all purposes.

Imaging probe 100 can include a distal tip portion, distal tip 119. In some embodiments, distal tip 119 can comprise a spring tip, such as a spring tip configured to improve the "navigability" of imaging probe 100 (e.g. to improve "trackability" and/or "steerability" of imaging probe 100), for example within a tortuous pathway (e.g. within a blood vessel of the brain or heart with a tortuous pathway). In some embodiments, tip 119 comprises a length of between 5 mm and 100 mm (e.g. a spring with a length between 5 mm and 100 mm). Alternatively or additionally, tip 119 can comprise a cap, plug, or other element configured to seal the distal opening of window 130. In some embodiments, tip 119 can comprise a radiopaque marker configured to increase the visibility of imaging probe 100 under an X-ray or fluoroscope. In some embodiments, tip 119 can comprise a relatively short luminal guidewire pathway to allow "rapid exchange" translation of imaging probe 100.

In some embodiments, at least the distal portion of imaging probe 100 (e.g. the distal portion of shaft 120 surrounding optical assembly 115) comprises an outer diameter of no more than 0.020", or no more than 0.014".

In some embodiments, imaging probe 100 can be constructed and arranged for use in an intravascular neural procedure (e.g. a procedure in which the blood, vasculature, and other tissue proximate the brain are visualized, and/or devices positioned temporarily or permanently proximate the brain are visualized). An imaging probe 100 configured for use in a neural procedure can comprise an overall length of at least 150 cm, such as a length of approximately 300 cm.

Alternatively or additionally, imaging probe 100 can be constructed and arranged for use in an intravascular cardiac procedure (e.g. a procedure in which the blood, vasculature, and other tissue proximate the heart are visualized, and/or devices positioned temporarily or permanently proximate the heart are visualized). An imaging probe 100 configured for use in a cardiovascular procedure can comprise an overall length of at least 120 cm, such as an overall length of approximately 265 cm, such as an overall length of approximately 280 cm. In some embodiments, imaging probe 100 can comprise a length greater than 230 cm, such as greater than 260 cm, and/or less than 320 cm.

Rotation assembly 500 comprises a connector assembly 510, operably attached to a rotary joint 550. Rotation assembly 500 further comprises a motor or other rotational energy source, motive element 530. Motive element 530 is operably attached to rotary joint 550 via a linkage assembly 540. In some embodiments, linkage assembly 540 comprises one or more gears, belts, pulleys, or other force transfer mechanisms. Motive element 530 can drive (e.g. rotate via linkage assembly 540) rotary joint 550 (and in turn core 110) at speeds of at least 100 rotations per second, such as at least 200 rotations per second or 250 rotations per second, or between 20 rotations per second and 1000 rotations per second. Motive element 530 can comprise a mechanism selected from the group consisting of: a motor; a servo; a stepper motor (e.g. a stepper motor including a gear box); a linear actuator; a hollow core motor; and combinations thereof. In some embodiments, rotation assembly 500 is configured to rotate optical assembly 115 and rotatable core 110 in unison.

Connector assembly 510 operably attaches to connector assembly 150 of imaging probe 100, allowing optical connector 161 to operably engage rotary joint 550. In some embodiments, connector assembly 510 operably engages connector assembly 150. In some embodiments, connector assembly 510 operably engages connector assembly 150 such that rotary joint 550 and optical connector 161 are free to rotate within the engaged assemblies.

Retraction assembly 800 comprises a connector assembly 820, that operably attaches to a reference point, for example connector 82 of delivery catheter 80, such as to establish a reference for retraction assembly 800 relative to the patient. Connector assembly 820 can attach to a reference point such as a patient introduction device, surgical table, and/or another fixed or semi fixed point of reference. A retraction element, puller 850, releasably attaches to connector 180 of imaging probe 100, such as via a carrier 855. Retraction assembly 800 retracts at least a portion of imaging probe 100 (e.g. the portion of imaging probe 100 distal to the attached connector 180), relative to the established reference. In some embodiments, retraction assembly 800 is configured to retract at least a portion of imaging probe 100 (e.g. at least optical assembly 115 and a portion of shaft 120) at a rate of between 5 mm/sec and 200 mm/sec, such as 100 mm/sec, and/or a rate between 5 mm/sec and 100 mm/sec, such as 60 mm/sec. Additionally or alternatively, the pullback procedure can be performed during a time period of between 0.5 sec and 25 sec, for example approximately 20 sec (e.g. over a distance of 100 mm at 5 mm/sec). Service loop 185 of imaging probe 100 can be positioned between retraction assembly 800 and/or at least connector assembly 820, and rotation assembly 500, such that imaging probe 100 can be retracted relative to the patient while rotation assembly 500 remains stationary (e.g. attached to the surgical table and/or to a portion of console 50).

Retraction assembly 800 further comprises a linear drive, motive element 830. In some embodiments, motive element 830 can comprise a linear actuator, a worm drive operably attached to a motor, a pulley system, and/or other linear force transfer mechanisms. Puller 850 can be operably attached to motive element 830 via a linkage assembly 890. In some embodiments, linkage assembly 890 can comprise one or more components of a "pullback assembly", as described herebelow in reference to FIGS. 1A and 2A. Alternatively or additionally, linkage assembly 890 can comprise one or more components of an enclosed pullback connector, as described herebelow in reference to FIG. 1B. One or more components of linkage assembly 890 can establish a frame of reference (e.g. an internal pullback reference) between puller 850 and the motive element 830, such that motive element 830 applies a pullback force to puller 850 via linkage assembly 890, and puller 850 retracts relative to the distal portion of linkage assembly 890 (e.g. relative to the distal end of sheath 895 as described herebelow in reference to FIG. 1A). In some embodiments, the distal end of linkage assembly 890 and connector assembly 820 are fixed relative to each other, and puller 850 translates linearly between the two in reaction to a force applied from motive element 830.

Console 50 comprises an imaging assembly 300, a user interface 55, processor 52, and one or more algorithms 51. Imaging assembly 300 can be configured to provide light to optical assembly 115 (e.g. via optical core 110) and collect light from optical assembly 115 (e.g. via optical core 110). Imaging assembly 300 can include a light source 310. Light source 310 can comprise one or more light sources, such as one or more light sources configured to provide one or more wavelengths of light to optical assembly 115 via optical core 110. Light source 310 is configured to provide light to optical assembly 115 (via optical core 110) such that image data can be collected comprising cross-sectional, longitudinal and/or volumetric information related to a patient site or implanted device being imaged. Light source 310 can be configured to provide light such that the image data collected includes characteristics of tissue within the patient site being imaged, such as to quantify, qualify or otherwise provide information related to a patient disease or disorder present within the patient site being imaged. Light source 310 can be configured to deliver broadband light and have a center wavelength in the range from 350 nm to 2500 nm, from 800 nm to 1700 nm, from 1280 nm to 1310 nm, or approximately 1300 nm (e.g. light delivered with a sweep range from 1250 nm to 1350 nm). Light source 310 bandwidth can be selected to achieve a desired resolution, which can vary according to the needs of the intended use of imaging system 10. In some embodiments, bandwidths are about 5% to 15% of the center wavelength, which allows resolutions of between 20 µm and 5 µm. Light source 310 can be configured to deliver light at a power level meeting ANSI Class 1 ("eye safe") limits, though higher power levels can be employed. In some embodiments, light source 310 delivers light in the 1.3 µm band at a power level of approximately 20 mW. Tissue light scattering is reduced as the center wavelength of delivered light increases, however water absorption increases. Light source 310 can deliver light at a wavelength approximating 1300 nm to balance these two effects. Light source 310 can be configured to deliver shorter wavelength light (e.g. approximately 800 nm light) to traverse patient sites to be imaged including large amounts of fluid. Alternatively, or additionally, light source 310 can be configured to deliver longer wavelengths of light (e.g. approximately 1700 nm light), such as to reduce a high level of scattering within a patient site to be imaged. In some embodiments, light source 310 comprises a tunable light source (e.g. light source 310 emits a single wavelength that changes repetitively over time), and/or a broad-band light source. Light source 310 can comprise a single spatial mode light source or a multimode light source (e.g. a multimode light source with spatial filtering). The user interface includes a display 56 and an input 57.

Console 50 can comprise one or more algorithms, such as algorithm 51 shown, which can be configured to adjust (e.g. automatically and/or semi-automatically adjust) one or more operational parameters of imaging system 10, such as an operational parameter of console 50, imaging probe 100 and/or a delivery catheter 80. Console 50 can further comprise a processing assembly, processor 52, configured to execute algorithm 51, and/or perform any type of data processing, such as digital signal processing, described herebelow in reference to FIG. 4. Additionally or alternatively, algorithm 51 can be configured to adjust an operational parameter of a separate device, such as injector 20 or implant delivery device 30 described herebelow. In some embodiments, algorithm 51 is configured to adjust an operational parameter based on one or more sensor signals, such as a sensor signal provided by a sensor-based functional element of the present inventive concepts as described herein. Algorithm 51 can be configured to adjust an operational parameter selected from the group consisting of: a rotational parameter such as rotational velocity of optical core 110 and/or optical assembly 115; a retraction parameter of shaft 120 and/or optical assembly 115 such as retraction velocity, distance, start position, end position and/or retraction initiation timing (e.g. when retraction is initiated); a position parameter such as position of optical assembly 115; a line spacing parameter such as lines per frame; an image display parameter such as a scaling of display size to vessel diameter; an imaging probe 100 configuration parameter; an injectate 21 parameter such as a saline to contrast ratio configured to determine an appropriate index of refraction; a light source 310 parameter such as power delivered and/or frequency of light delivered; and combinations of one or more of these. In some embodiments, algorithm 51 is configured to adjust a retraction parameter such as a parameter triggering the initiation of the pullback, such as a pullback that is initiated based on a parameter selected from the group consisting of: lumen flushing (the lumen proximate optical assembly 115 has been sufficiently cleared of blood or other matter that would interfere with image creation); an indicator signal is received from injector 20 (e.g. a signal indicating sufficient flushing fluid has been delivered); a change in image data collected (e.g. a change in an image is detected, based on the image data collected, that correlates to proper evacuation of blood from around optical assembly 115); and combinations of one or more of these. In some embodiments, algorithm 51 is configured to adjust an imaging system 10 configuration parameter related to imaging probe 100, such as when algorithm 51 identifies (e.g. automatically identifies via an RF or other embedded ID) the attached imaging probe 100 and adjusts an imaging system 10 parameter, such as an arm path length parameter, a dispersion parameter, and/or other parameter as listed above.

Imaging system 10 can comprise one or more interconnect cables, bus 58 shown. Bus 58 can operably connect rotation assembly 500 to console 50, retraction assembly 800 to console 50, and or rotation assembly 500 to retraction assembly 800. Bus 58 can comprise one or more optical transmission fibers, electrical transmission cables, fluid conduits, and combinations of one or more of these. In some embodiments, bus 58 comprises at least an optical transmission fiber that optically couples rotary joint 550 to imaging assembly 300 of console 50. Additionally or alternatively, bus 58 comprises at least power and/or data transmission cables that transfer power and/or motive information to one or more of motive elements 530 and 830.

Second imaging device 15 can comprise an imaging device such as one or more imaging devices selected from the group consisting of: an X-ray; a fluoroscope such as a single plane or biplane fluoroscope; a CT Scanner; an MRI; a PET Scanner; an ultrasound imager; and combinations of one or more of these. In some embodiments, second imaging device 15 comprises a device configured to perform rotational angiography.

Treatment device 16 can comprise an occlusion treatment or other treatment device selected from the group consisting of: a balloon catheter constructed and arranged to dilate a stenosis or other narrowing of a blood vessel; a drug eluting balloon; an aspiration catheter; a sonolysis device; an atherectomy device; a thrombus removal device such as a stent retriever device; a Trevo™ stentriever; a Solitaire™ stentriever; a Revive™ stentriever; an Eric™ stentriever; a Lazarus™ stentriever; a stent delivery catheter; a microbraid implant; an embolization system; a WEB™ embolization system; a Luna™ embolization system; a Medina™ embolization system; and combinations of one or more of these. In some embodiments, imaging probe 100 is configured to collect data related to treatment device 16 (e.g. treatment device 16 location, orientation and/or other configuration data), after treatment device 16 has been inserted into the patient.

Injector 20 can comprise a power injector, syringe pump, peristaltic pump or other fluid delivery device configured to inject a contrast agent, such as radiopaque contrast, and/or other fluids. In some embodiments, injector 20 is configured to deliver contrast and/or other fluid (e.g. contrast, saline and/or Dextran). In some embodiments, injector 20 delivers fluid in a flushing procedure as described herebelow. In some embodiments, injector 20 delivers contrast or other fluid through a delivery catheter 80 with an ID of between 5 Fr and 9 Fr, a delivery catheter 80 with an ID of between 0.53" to 0.70", or a delivery catheter 80 with an ID between 0.0165" and 0.027". In some embodiments, contrast or other fluid is delivered through a delivery catheter as small as 4 Fr (e.g. for distal injections). In some embodiments, injector 20 delivers contrast and/or other fluid through the lumen of one or more delivery catheters 80, while one or more smaller delivery catheters 80 also reside within the lumen. In some embodiments, injector 20 is configured to deliver two dissimilar fluids simultaneously and/or sequentially, such as a first fluid delivered from a first reservoir and comprising a first concentration of contrast, and a second fluid from a second reservoir and comprising less or no contrast.

Injectate 21 can comprise fluid selected from the group consisting of: optically transparent material; saline; visualizable material; contrast; Dextran; an ultrasonically reflective material; a magnetic material; and combinations thereof. Injectate 21 can comprise contrast and saline. Injectate 21 can comprise at least 20% contrast. During collection of image data, a flushing procedure can be performed, such as by delivering one or more fluids, injectate 21 (e.g. as propelled by injector 20 or other fluid delivery device), to remove blood or other somewhat opaque material (hereinafter non-transparent material) proximate optical assembly 115 (e.g. to remove non-transparent material between optical assembly 115 and a delivery catheter and/or non-transparent material between optical assembly 115 and a vessel wall), such as to allow light distributed from optical assembly 115 to reach and reflectively return from all tissue and other objects to be imaged. In these flushing embodiments, injectate 21 can comprise an optically transparent material, such as saline. Injectate 21 can comprise one or more visualizable materials, as described herebelow.

As an alternative to or in addition to its use in a flushing procedure, injectate 21 can comprise material configured to be viewed by second imaging device 15, such as when injectate 21 comprises a contrast material configured to be viewed by a second imaging device 15 comprising a fluoroscope or other X-ray device; an ultrasonically reflective material configured to be viewed by a second imaging device 15 comprising an ultrasound imager; and/or a magnetic material configured to be viewed by a second imaging device 15 comprising an MRI.

Implant 31 can comprise an implant (e.g. a temporary or chronic implant) for treating one or more of a vascular occlusion or an aneurysm. In some embodiments, implant 31 comprises one or more implants selected from the group consisting of: a flow diverter; a Pipeline™ flow diverter; a Surpass™ flow diverter; an embolization coil; a stent; a Wingspan™ stent; a covered stent; an aneurysm treatment implant; and combinations of one or more of these.

Implant delivery device 30 can comprise a catheter or other tool used to deliver implant 31, such as when implant 31 comprises a self-expanding or balloon expandable portion. In some embodiments, imaging system 10 comprises imaging probe 100, one or more implants 31 and/or one or more implant delivery devices 30. In some embodiments, imaging probe 100 is configured to collect data related to implant 31 and/or implant delivery device 30 (e.g. implant 31 and/or implant delivery device 30 anatomical location, orientation and/or other configuration data), after implant 31 and/or implant delivery device 30 has been inserted into the patient.

In some embodiments, one or more system components, such as console 50, delivery catheter 80, imaging probe 100, rotation assembly 500, retraction assembly 800, treatment device 16, injector 20, and/or implant delivery device 30, further comprise one or more functional elements ("functional element" herein), such as functional elements 59, 89, 199, 599, 899, 99a, 99b, and/or 99c, respectively, shown. Each functional element can comprise at least two functional elements. Each functional element can comprise one or more elements selected from the group consisting of: sensor; transducer; and combinations thereof. The functional element can comprise a sensor configured to produce a signal. The functional element can comprise a sensor selected from the group consisting of: a physiologic sensor; a pressure sensor; a strain gauge; a position sensor; a GPS sensor; an accelerometer; a temperature sensor; a magnetic sensor; a chemical sensor; a biochemical sensor; a protein sensor; a flow sensor such as an ultrasonic flow sensor; a gas detecting sensor such as an ultrasonic bubble detector; a sound sensor such as an ultrasound sensor; and combinations thereof. The sensor can comprise a physiologic sensor selected from the group consisting of: a pressure sensor such as a blood pressure sensor; a blood gas sensor; a flow sensor such as a blood flow sensor; a temperature sensor such as a blood or other tissue temperature sensor; and combinations thereof. The sensor can comprise a position sensor configured to produce a signal related to a vessel path geometry (e.g. a 2D or 3D vessel path geometry). The sensor can comprise a magnetic sensor. The sensor can comprise a flow sensor. The system can further comprise an algorithm configured to process the signal produced by the sensor-based functional element. Each functional element can comprise one or more transducers. Each functional element can comprise one or more transducers selected from the group consisting of: a heating element such as a heating element configured to deliver sufficient heat to ablate tissue; a cooling element such as a cooling element configured to deliver cryogenic energy to ablate tissue; a sound transducer such as an ultrasound transducer; a vibrational transducer; and combinations thereof.

Figure 1A:
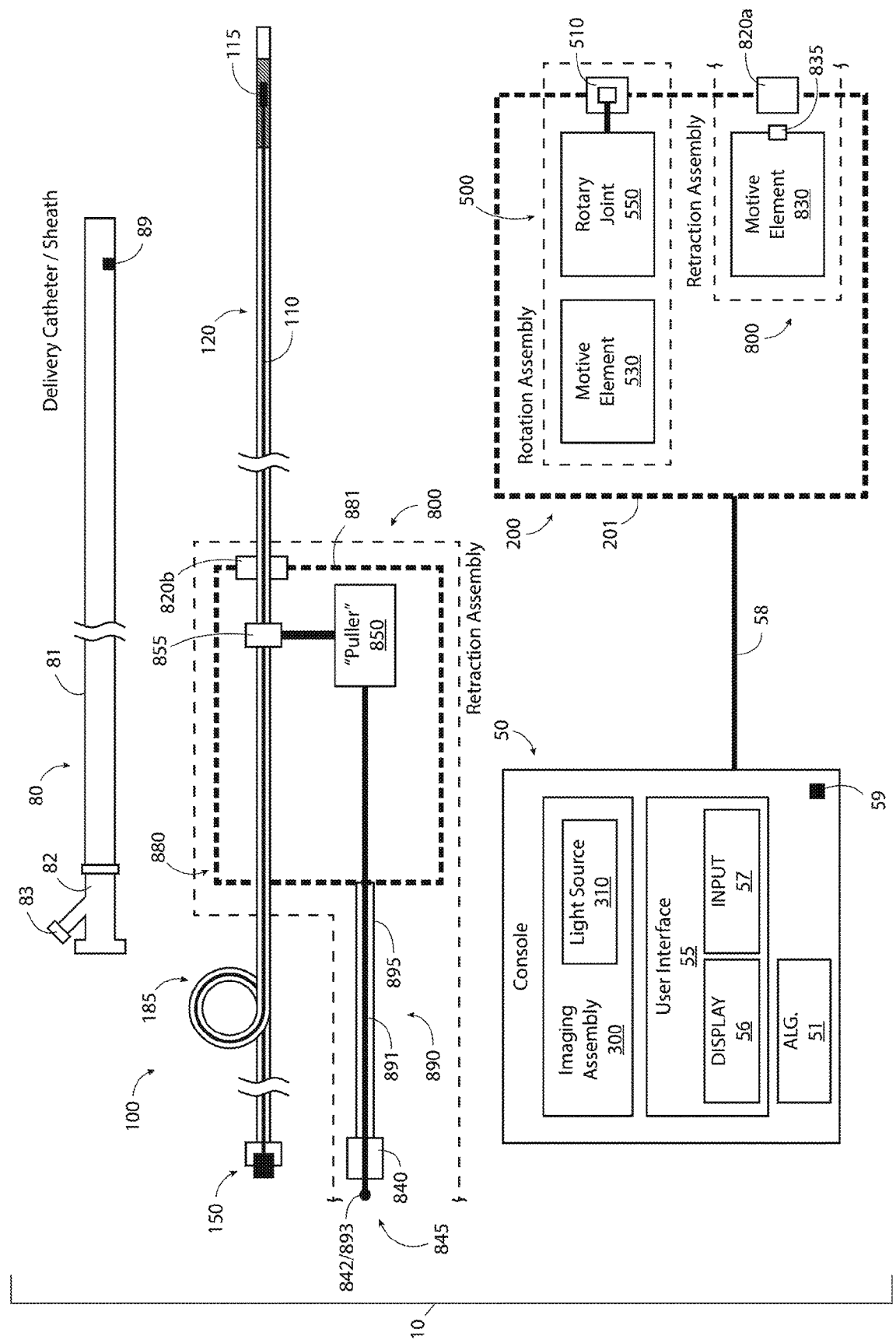
FIG. 1A illustrates a schematic view of an imaging system comprising an imaging probe operably attachable to a patient interface module, and an independent pullback module operably attachable to the patient interface module and the imaging probe, consistent with the present inventive concepts.

Referring now to FIG. 1A, a schematic view of an imaging system is illustrated, the system comprising an imaging probe operably attachable to a patient interface module, and an independent pullback module operably attachable to the patient interface module and the imaging probe, consistent with the present inventive concepts. Imaging system 10 can comprise a patient interface module 200. Patient interface module 200 comprises a housing, housing 201, surrounding at least a portion of rotation assembly 500, and at least a portion of retraction assembly 800. Imaging system 10 can further comprise a second, discrete component, pullback module 880. Pullback module 880 comprises a housing, housing 881, surrounding at least a portion of retraction assembly 800. Pullback module 880 and patient interface module 200 can be operably attached to each other via a connector assembly, linkage assembly 890 described herein. Pullback module 880 and patient interface module 200 can be constructed and arranged (via each having a separate housing) to enable positioning at different locations (e.g. linkage assembly 890 connecting modules 880 and 200 can comprise a length of at least 15 cm such that the two remote locations can be at least 15 cm apart), for example patient interface module 200 can be positioned on or near a surgical bed rail, and pullback module 880 can be positioned near a vascular access site of the patient (e.g. within 30 cm of the vascular access site thru which imaging probe 100 enters the patient). Linkage assembly 890 can comprise a linkage 891 slidingly received within sheath 895. Linkage 891 is operably attached to puller 850, and the proximal end 893 of linkage 891 can comprise a connection point, 842. Components shown in FIG. 1A can be of similar construction and arrangement to like components described in FIG. 1 hereabove, and as described elsewhere herein.

Figure 2A:
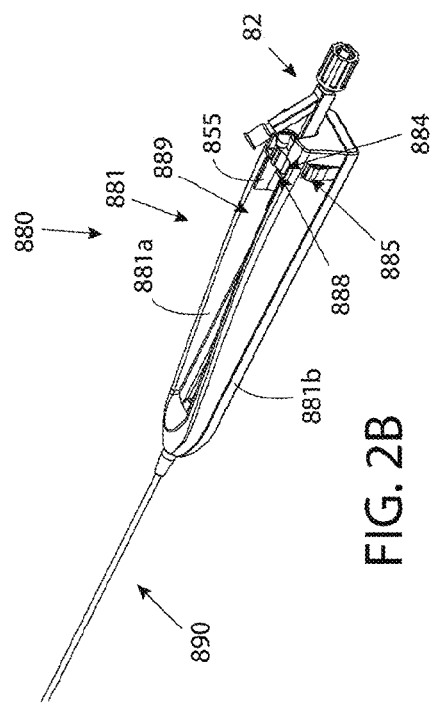
FIG. 2A illustrates a perspective view of connectors being attached to a patient interface module, consistent with the present inventive concepts.
Figure 2B:
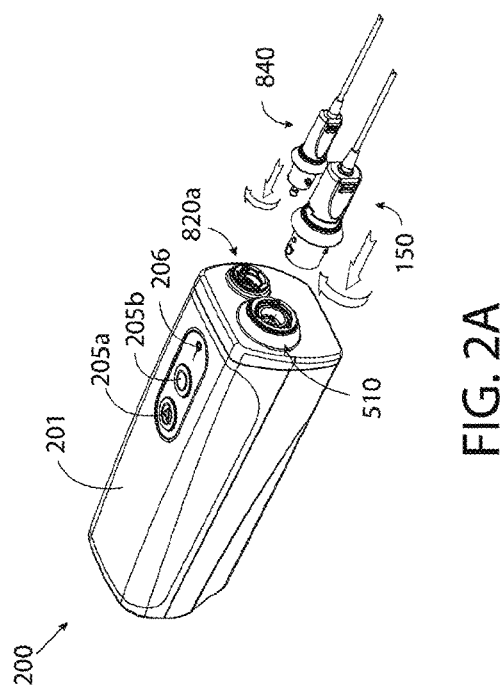
FIG. 2B illustrates a perspective view of a pullback housing, consistent with the present inventive concepts.

Pullback module 880 can comprise a connector assembly 820b that operably attaches to connector 82 of delivery catheter 80, such as described herebelow in reference to FIG. 2B. Connector assembly 845 can comprise a connector 840 that operably attaches to a connector assembly 820a of patient interface module 200, as described herebelow in reference to FIG. 2A.

Figure 1B:
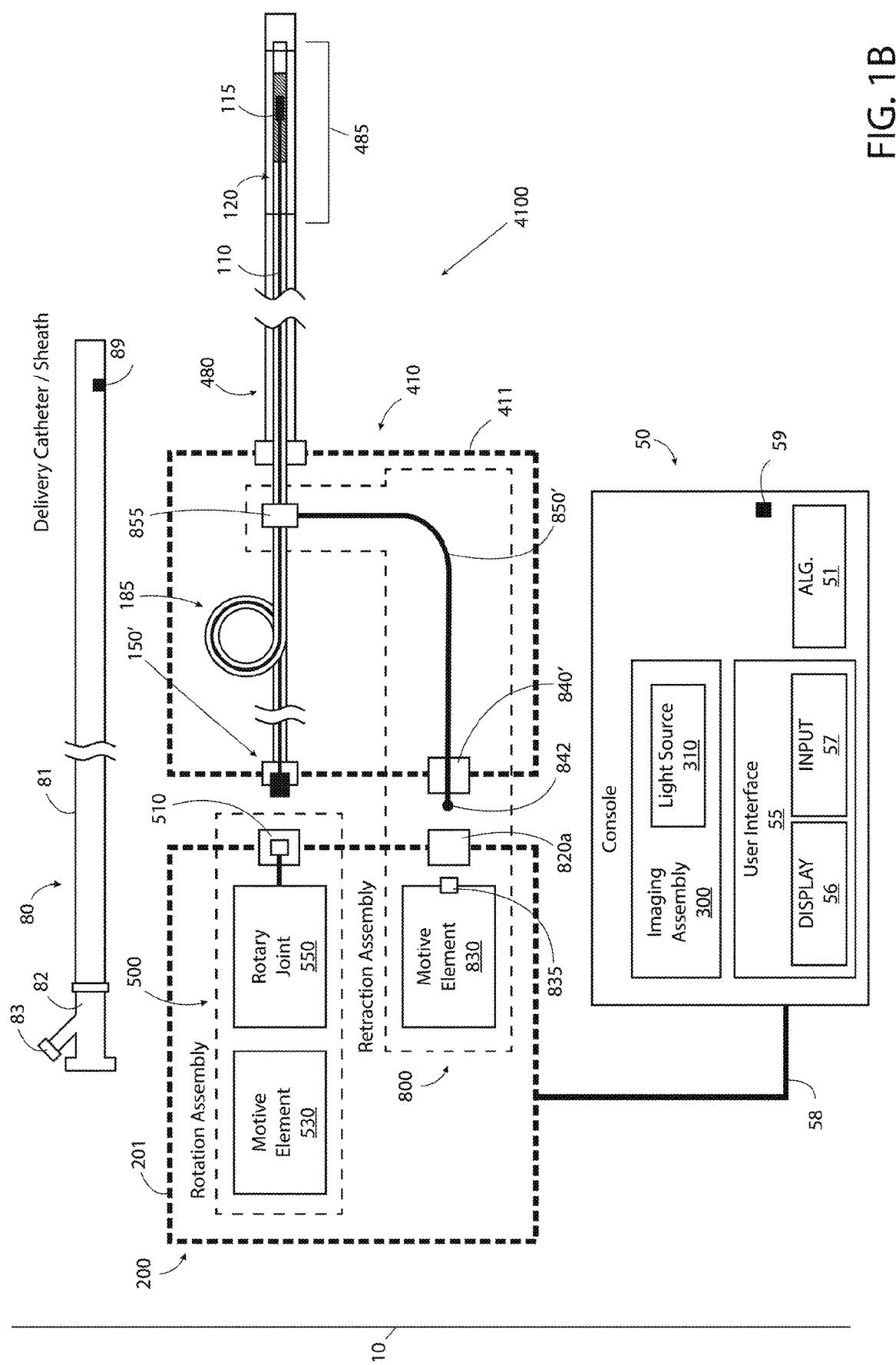
FIG. 1B illustrates a schematic view of an imaging system comprising an imaging probe operably attachable to a module comprising a first connector for attaching to a rotation motive element and a second connector for attaching to a retraction motive element, consistent with the present inventive concepts.

Referring now to FIG. 1B, a schematic view of an imaging system is illustrated, the system comprising an imaging probe operably attachable to a module comprising a first connector for attaching to a rotation motive element and a second connector for attaching to a retraction motive element, consistent with the present inventive concepts. Imaging system 10 can comprise a patient interface module 200 as described herein. Imaging system 10 can further comprise a connector module, module 410. Module 410 comprises a housing, housing 411, surrounding at least a portion of retraction assembly 800, service loop 185 of imaging probe 100, connector assembly 150', and connector 840'. Module 410 can be configured to operably attach both imaging probe 100 and a linkage, puller 850', to patient interface module 200. Components shown in FIG. 1B can be of similar construction and arrangement to like components described in FIG. 1 hereabove, and as described elsewhere herein. Module 410 can be operably attached to a delivery catheter 480. Delivery catheter 480 can be of similar construction and arrangement to delivery catheter 80 described hereabove in reference to FIG. 1. Delivery catheter 480 can comprise at least a portion that is optically transparent, window 485. Window 485 can be positioned at or near a distal portion of delivery catheter 480. Window 485 can comprise a material transparent to imaging modalities utilized by imaging probe 100, such that imaging probe 100 can image through window 485, for example when optical assembly 115 is retracted within window 485. In some embodiments, module 410, delivery catheter 480, and imaging probe 100 collectively form catheter assembly 4100.

Referring now to FIG. 2A, a perspective view of connectors being attached to a patient interface is illustrated, consistent with the present inventive concepts. Patient interface module 200 is configured to provide rotation to a rotatable optical core of an imaging probe, and to provide a motive force to translate at least a portion of the imaging probe, such as is described herebelow. Patient interface module 200 comprises rotation assembly 500, and at least a portion of retraction assembly 800. A housing 201 surrounds patient interface module 200. Patient interface module 200 can comprise one or more user interface elements, such as one or more inputs, buttons 205a,b, and one or more outputs, indicator 206 shown. Patient interface module 200 comprises a first physical connector assembly, connector assembly 510, for operably connecting to connector assembly 150 as described herein. Patient interface module 200 can further comprise a second physical connector assembly, connector assembly 820a, for operably connecting to connector 840 also as described herein. Connector assembly 150 and connector 840 can each comprise bayonet type connectors, constructed and arranged to be at least partially inserted into connector assemblies 510 and 820a, respectively. Connector assembly 150 and connector 840 can be subsequently rotated (e.g. an approximately 45° rotation) to lock their connections with connector assemblies 510 and 820a, respectively, as described herein. Connector assembly 150 and/or 840 can comprise numerous forms of connectors, such as a bayonet or other locking connectors.

Referring now to FIG. 2B, a perspective view of a pullback assembly is illustrated, consistent with the present inventive concepts. Pullback module 880 can be operably attached to a portion of an imaging probe 100 of the present inventive concepts, and provide a retraction force to the probe, pulling at least a portion of the probe proximally relative to a patient (e.g. relative to a patient introduction device), as described herebelow. Pullback module 880 can comprise a construction and arrangement similar to pullback module 880 as described in applicant's co-pending International PCT Patent Application Serial No. PCT/US2018/062766, titled "Imaging System", filed Nov. 28, 2018, the content of which is incorporated herein by reference in its entirety. Pullback module 880 can be operably attached to the distal end of a linkage 891 (not shown). Linkage assembly 890 can be slidingly received through pullback module 880. Sheath 895 can be fixedly attached to the proximal end of module 880. Linkage 891 is slidingly received along the length of module 880 and is operably attached at its distal end to puller 850.

Pullback module 880 can comprise a two-part housing 881, including a top housing 881a and bottom housing 881b. Module 880 can contain a translating cart, puller 850 (not shown, but positioned below carrier 855, and as described herebelow). Puller 850 can be designed to translate within module 880. Module 880 can comprise a biasing element, spring 852 (not shown). Spring 852 can provide a biasing force to puller 850, such as to bias puller 850 distally.

Top housing 881a can comprise a first cavity, retention port 884 and a second cavity, trench 889. Retention port 884 and trench 889 can be separated by a projection, retention wall 888. Physical connector assembly 820b (described hereabove in reference to FIG. 1A) can comprise a retention port 884 of housing 881a, including wall 888, and a retention mechanism, clip 885. Clip 885 can be configured to releasably engage the proximal end of a delivery catheter such as sheath connector 82 of delivery catheter 80, such as when connector 82 comprises a Tuohy Borst connector. Physical connector assembly 820b can further comprise a biasing element, spring 886 (not shown). Spring 886 can provide a biasing force to maintain clip 885 in an engaged position about connector 82.

Pullback module 880 can further comprise a carrier 855. Carrier 855 can operably attach to puller 850, such as through a slot 889a (not shown) in housing 881a. Carrier 855 can translate within trench 889 in response to puller 850, which translates in response to linkage 891. Carrier 855 can operably attach to a portion of imaging probe 100, such as to a pullback connector 180. Pullback connector 180 can comprise a "torquer", or other device affixed to shaft 120 of imaging probe 100. Sheath 895 of linkage assembly 890 can provide a frame of reference between connector 840 and pullback module 880, such that when the proximal end of linkage 891 is retracted relative to connector 840, the distal end of linkage 891 is retracted towards sheath 895 (i.e. towards the proximal end of pullback module 880). This relative motion transfers motive force applied at connector 840 (e.g. via motive element 830, as described herein), to puller 850. Puller 850 subsequently transfers the motive force to imaging probe 100, and imaging probe 100 is retracted relative to the patient.

In operation, imaging probe 100 can be manually (e.g. by a user) advanced through the vasculature of the patient. Pullback module 880 can be attached to the patient (e.g. to delivery catheter 80 via connector 82), and connector 180 can be operably connected to imaging probe 100, and positioned proximate delivery catheter 80 (e.g. a torquer connector 180 can be tightened to imaging probe 100 proximate delivery catheter 80). Connector 180 (not shown) can be operably positioned within carrier 855, and a motive force can be applied to the distal end of linkage 891. Carrier 855 retracts within trench 889, retracting imaging probe 100 relative to the patient. After retraction, connector 180 can be removed from carrier 855 (e.g. lifted out of), and carrier 855 and imaging probe 100 can be re-advanced independently. For example, carrier 855 can re-advance via the bias of spring 852, as the proximal end of linkage 891 is allowed to advance, and imaging probe 100 can be re-advanced manually by a user. Subsequent retractions can be performed by repositioning connector 180 in carrier 855 after both have been re-advanced. Carrier 855 can comprise a capturing portion, such as a "cup-like" geometry, a hook, or other capture-enabling portion, such that carrier 855 can only impart a retraction force on connector 180. In this configuration, if carrier 855 were to translate distally, connector 180 would automatically disengage from carrier 855 (e.g. connector 180 would fall out of the cup portion of carrier 855).

Figure 3:
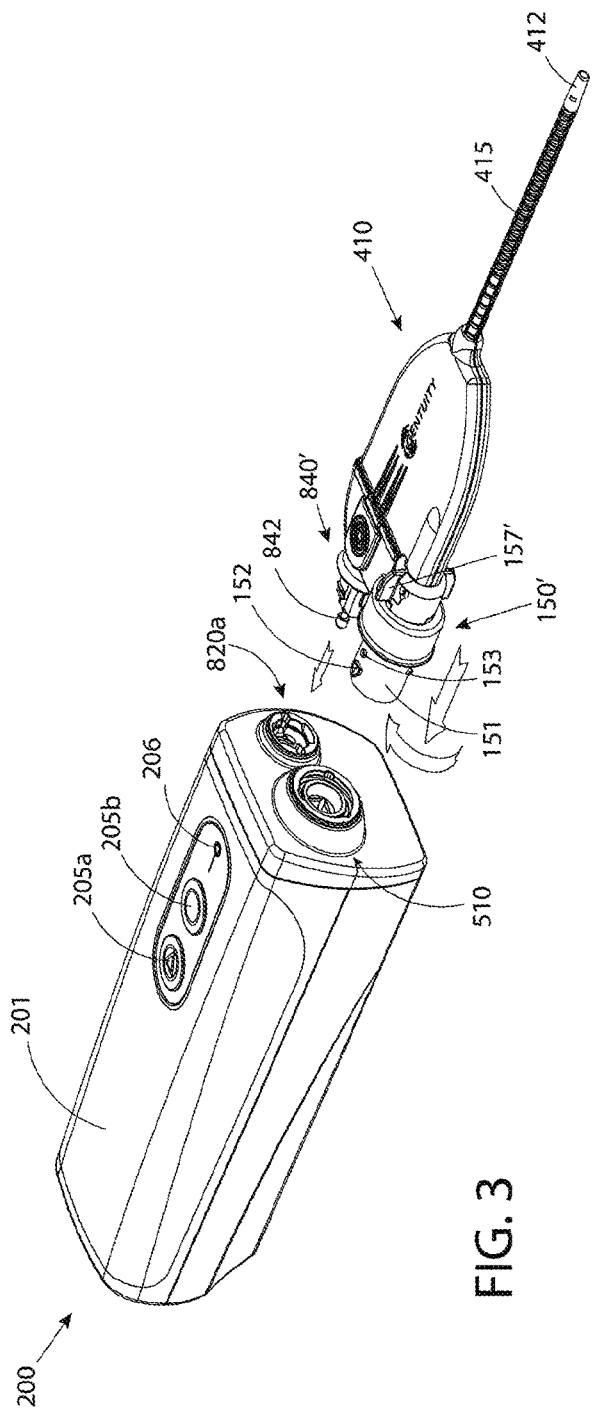
FIG. 3 illustrates a perspective view of connectors being attached to a patient interface module, consistent with the present inventive concepts.

Referring now to FIG. 3, a perspective view of connectors being attached to a patient interface module is illustrated, consistent with the present inventive concepts. Patient interface module 200 can be of similar construction and arrangement to patient interface module 200 as described hereabove in reference to FIG. 2A. Patient interface module 200 comprises a first physical connector assembly, connector assembly 510, for operably connecting to connector assembly 150'. Patient interface module 200 can further comprise a second physical connector assembly, connector assembly 820a, for operably connecting to connector 840'. Connector assembly 150' and connector 840' can each comprise bayonet type connectors, constructed and arranged to be at least partially inserted into connector assemblies 510 and 820a, respectively.

Figure 4:
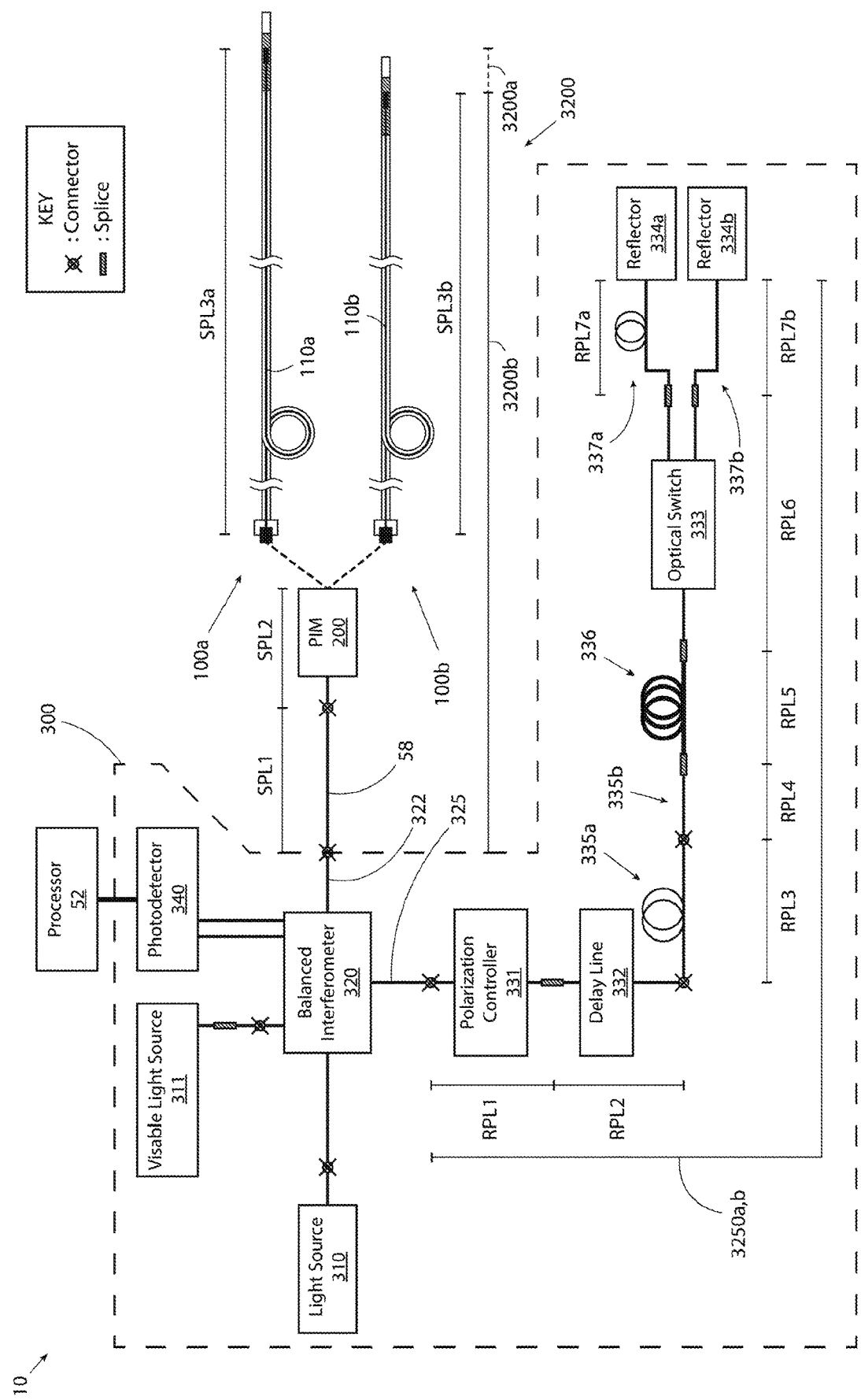
FIG. 4 illustrates a schematic view of an optical pathway of an imaging system, consistent with the present inventive concepts.

Referring now to FIG. 4, a schematic view of an optical pathway of an imaging system is illustrated, consistent with the present inventive concepts. A schematic of imaging assembly 300 is illustrated, along with two imaging probes, probes 100a and 100b, and PIM (patient interface module) 200. Imaging assembly 300 operably attaches to at least two different types of imaging probe 100 (e.g. via PIM 200), for example when imaging probe 100a comprises a different length than imaging probe 100b, as described herebelow. Imaging assembly 300 includes multiple optical splices and connectors. The optical path length of a component described herebelow comprises the optical path length between proximal and distal connectors (or splices) adjacent to the referenced component.

Imaging assembly 300 includes a balanced interferometer, interferometer 320, which is optically coupled to both a light source, light source 310, and a light measurement element, photodetector 340. Interferometer 320 includes a reference arm 325, which is optically coupled to a reference pathway 3250, and a sample arm 322, which is optically coupled to a sample pathway 3200. Sample pathway 3200 includes the optical path of an attached imaging probe (e.g. probe 100a or 100b). Interferometer 320 can be configured to receive light from light source 310, and optically split the received light to transmit the light along both reference pathway 3250 and sample pathway 3200. The light propagates away from interferometer 320 along each path, is reflected back along each pathway (e.g. as described herebelow), and the reflections are received by interferometer 320. Interferometer 320 then directs the reflected light received from each pathway 3250,3200 to photodetector 340. Photodetector 340 produces a signal related to the reflected light (e.g. a signal related to the difference in phase, amplitude, polarization, a spectral difference, or any combination thereof, in the light received from each pathway 3250,3200). The signal produced by photodetector 340 is used by system 10 to generate an OCT image, for example when processor 52 comprises a digital signal processor, which can be configured to process the signal and generate the OCT image. In some embodiments, imaging assembly 300 comprises a visible light source 311 (as shown), optically coupled to interferometer 320. Visible light source 311 can be used to introduce visible light to optical pathways 3250,3200 to provide a visible indication that proper optical connections have been achieved and/or to indicate that light source 310 is delivering light (e.g. when light source 310 delivers non-visible light, and light source 311 is activated whenever light source 310 is activated).

Sample pathway 3200 can include one or more waveguides (e.g. optical fibers, such as optical core 110), one or more optical elements (e.g. lenses and/or reflectors), one or more optical connectors, and/or one or more rotary optical joints, as described herein. In the embodiment shown, sample pathway 3200 includes bus 58, which includes one or more waveguides which optically connect imaging assembly 300 to PIM 200. Bus 58 comprises an optical path length SPL1. PIM 200 can include one or more waveguides and a rotary optical joint, as described hereabove in reference to FIGS. 1, 1A, and 1B. An imaging probe 100 (e.g. probe 100a or 100b) can be operably attached to PIM 200, such that optical cores 110a,b are optically coupled to interferometer 320 via PIM 200 and bus 58. PIM 200 comprises an optical path length of SPL2. Probes 100a and 100b comprise optical path lengths of SPL3a and SPL3b, respectively.

Sample pathway 3200 can comprise an optical path length equal to the total path length of SPL1, SPL2, and SPL3a or SPL3b. As described herebelow, sample pathway 3200a includes imaging probe 100a (e.g. when imaging probe 100a is connected to PIM 200) and sample pathway 3200b includes imaging probe 100b (e.g. when imaging probe 100b is connected to PIM 200).

Reference pathway 3250 includes one or more waveguides, one or more optical elements, one or more optical connectors, and/or one or more other functional optical components, such as polarizers or switches. Reference pathway 3250 can comprise one of two reference pathways, 3250a or 3250b as shown. Imaging assembly 300 can include numerous configurations and combinations of the one or more optical components described herebelow. In the embodiment shown, reference pathway 3250 includes a light polarizing component, polarization controller 331, optically coupled to the reference arm 325 of interferometer 320. Polarization controller 331 comprises an optical path length RPL1. Reference pathway 3250 further includes an optical delay component, delay line 332, which is optically coupled to polarization controller 331. Delay line 332 comprises an optical path length of RPL2. Reference pathway 3250 can include one or more patch cables (e.g. optical fibers), patch cables 335a and 335b, as well as a first matching cable, matching cable 336. Cables 335a, 335b, and 336 are serially connected between delay line 332 and an optical switch 333. Cables 335a, 335b, and 336 comprise optical path lengths RPL3, RPL4, and RPL5, respectively. Reference pathway 3250 includes two additional matching cables, cables 337a and 337b, each optically coupled to optical switch 333, and terminating at a reflective element, retroreflectors 334a and 334b, respectively. Cables 337a and 337b comprise optical path lengths RPL7a and RPL7b, respectively.

Reference pathway 3250 can comprise an optical path length equal to the total path length of RPL1, RPL2, RPL3, RPL4, RPL5, RPL6, and RPL7 (e.g. RPL7a or RPL7b). As described herebelow, reference pathway 3250a includes cable 337a (e.g. when optical switch 333 optically connects cable 337a to cable 336), and reference pathway 3250b includes cable 337b (e.g. when optical switch 333 optically connects cable 337b to cable 336).

Polarization controller 331 can be configured to polarize and/or filter light as it propagates through the controller. In some embodiments, photodetector 340 is configured to detect the interference of light received from sample pathway 3200 and reference pathway 3250, such as by performing a vector multiplication of the respective electric fields (of the received light). In these embodiments, an optimized signal is detected when the electric fields of the received light are parallel (with a minimal signal resulting from perpendicular fields). Polarization controller 331 can be configured to optimize the photodetector signal by aligning the polarization vector of the reference light to the sample light.

Delay line 332 can be configured to dynamically adjust its optical path length (i.e. optical path length RPL2). Delay line 332 can adjust (e.g. increase or decrease) path length RPL2 to allow calibration of reference pathway 3250, for example a calibration performed in a manufacturing process. Delay line 332 can adjust path length RPL2 up to 200 mm, such as up to 1000 mm (e.g. plus or minus 500 mm). In some embodiments, delay line 332 can comprise a step size of approximately 10 μm, such as a step size smaller than 15 μm, such as smaller than 30 μm. In some embodiments, delay line 332 is configured to fine-tune the optical path length matching of reference pathway 3250 and sample pathway 3200 while imaging probe 100 is in use, such as when either the sample pathway 3200 or reference pathway 3250 experiences a change in temperature (e.g. placing imaging probe 100 in the patient body) resulting in a change in the optical index of the fiber used in the pathway, which then causes a change of the optical path length. In some embodiments, delay line 332 can comprise a motorized delay line. In some embodiments, imaging assembly 300 and/or system 10 is configured to calibrate reference pathway 3250 to match sample pathway 3200 in a closed loop fashion, such as is described in detail herebelow in reference to FIG. 6. In some embodiments, rotatable optical core 110 is not rotated during calibration.

It can be desirable to match the optical properties of a sample pathway of an imaging system (e.g. sample pathway 3200 described herein) to the reference pathway of the imaging system (e.g. reference pathway 3250 described herein). The matched optical properties of the optical fibers of each pathway (e.g. sample pathway 3200 and reference pathway 3250) can include an optical property selected from the group consisting of: the NA of the optical fibers; the dispersion of the optical fibers, such as the second-order dispersion (e.g. group velocity dispersion (GVD)); the total optical path length of sample pathway 3200 and reference pathway 3250, such as when the optical path length of sample pathway 3200 changes significantly (e.g. when using different imaging probes 100) which can be beyond the mechanical range of delay line 332; and combinations of these. In some embodiments, sample pathway 3200 comprises multiple segments, where each segment can comprise unique parameters (e.g. parameters applicable to the length of the segment). It is desired to match the length and parameters of each of these segments of sample pathway 3200 to segments of reference pathway 3250.

In some embodiments, sample pathway 3200 comprises a first set of optical parameters, comprising the optical parameters of the components of the optical core 110 of imaging probe 100, PIM 200, bus 58, and one or more connectors within sample pathway 3200. In some embodiments, optical core 110 of imaging probe 100 comprises dissimilar properties to the optical components of PIM 200 and bus 58. For example, optical core 110 can comprise one or more optical properties selected based on a desired performance of imaging probe 100, which can differ from the optical properties of commonly available and/or more easily manufacturable optical components which may be used in imaging assembly 300. Reference pathway 3250 can comprise a second set of optical parameters, comprising the optical parameters of the components of imaging assembly 300 described herein. In some embodiments, the lengths and optical properties of the components comprising sample pathway 3200 and the lengths and optical properties of the components comprising reference pathway 3250 are selected such that the pathways 3200,3250 have similar overall optical parameters. In some embodiments, the optical cores 110 of multiple imaging probes 100 comprise optical path lengths of 3,000 mm and 2,800 mm as described herebelow. Additionally or alternatively, various imaging probes 100 can each comprise an optical core 110 with optical path lengths ranging from 1,200 mm to 4,000 mm, such as from 2,500 mm to 3,500 mm, such as 2,600 mm, 2,800 mm, 3,000 mm, 3,200 mm, and/or 3,400 mm.

In the embodiment shown in FIG. 4, matching cable 336 of reference pathway 3250 comprises a length of 2,900 mm, the length selected to relatively closely match the lengths of both optical core 110a and 110b (3,000 mm and 2,800 mm respectively). Matching cable 336 comprises optical properties similar to optical cores 110, for example each comprise a matching NA, such as an NA of 0.16. Additionally or alternatively, the matched optical properties include the zero dispersion wavelength and/or the dispersion slope. The remaining components of reference pathway 3250 can comprise dissimilar optical properties, such as an NA of 0.14. Path length SPL1 and SPL2 (e.g. the physical length of bus 58 and the overall path length of PIM 200) can be configured to match the overall path length of these remaining components of reference pathway 3250. Bus 58 and PIM 200 can comprise similar optical properties to these remaining components of reference pathway 3250, such that the overall optical properties of sample pathway 3200 match (or closely match) those of reference pathway 3250.

In some embodiments, path length RPL3 of patch cable 335a can be selected (e.g. in a manufacturing process) to accommodate variances in component lengths due to manufacturing tolerances and/or other reasons. For example, after assembly of polarization controller 331 and delay line 332 to interferometer 320, the total path length of RPL1 and RPL2 can be measured (e.g. optically measured). Similarly, after assembly of cables 335b, 336, and optical switch 333, the total path length of RPL4, RPL5, and RPL6 can be measured. Path length RPL3 of cable 335a can be chosen to ensure the overall path length RPL1-RPL6 meets a desired manufacturing tolerance. In some embodiments, the path lengths RPL7a,b of cables 337a,b comprise a relatively shorth length, for example no more than 100 mm, such as no more than 75 mm, or no more than 50 mm. Cables 337a,b can be manufactured with a smaller tolerance than other cables of imaging assembly 300, for example within a tolerance such that delay line 332 can be used to compensate for any path length error. In some embodiments, matching cable 336 is configured to match the dispersion properties of optical core 110, with a larger manufacturing tolerance than the path length matching that is achieved by cables 337a and 337b. This larger tolerance can be acceptable in an OCT system, such as system 10, because the effect per mm of dispersion differences between sample pathway 3200 and reference pathway 3250 is much less than a similar path length mismatch.

System 10 can comprise one, two, three, or more unique imaging probe types, such as imaging probes 100a,b shown. Each imaging probe type can comprise different properties, for example a different length (e.g. a different patient-insertable length). Imaging assembly 300 can be configured to detect (e.g. via a handshake protocol, user input, and/or a unique imaging probe identifier) the particular type of imaging probe 100 that is attached to PIM 200. Based on the type of imaging probe 100 detected, imaging assembly 300 can correspondingly adjust reference pathway 3250, for example by switching optical switch 333. In the embodiment shown, system 10 comprises two imaging probes 100: imaging probe 100a comprising path length SPL3a; and imaging probe 100b comprising path length SPL3b. Path length SPL3a can comprise a length of 3,000 mm, and path length SPL3b can comprise a length of 2,800 mm.

The path lengths described immediately herebelow provide an illustrative example of a variable reference arm configuration configured to match different sample arm configurations. The path lengths of each component can be varied, so long as the overall sample and reference path lengths are equal, and/or the difference is known. Path length SPL2 can comprise a length of 441 mm, and SPL1 can comprise a length of 4,090 mm, such that sample pathway 3200a comprises an overall path length of 7,531 mm, and 3200b comprises an overall path length of 7,331 mm. In this embodiment, path lengths RPL1, RPL2, RPL3, RPL4, RPL5, and RPL6 comprise path lengths of, 470 mm, 520 mm, 2,041 mm, 250 mm, 2,900 mm, and 850 mm, respectively, such that the reference path length between interferometer 320 and the distal side of optical switch 333 comprises a path length of 7,031 mm. Optical switch 333 can be configured to switch between cable 337a, comprising path length RPL7a, and cable 337b, comprising path length 337b, based on which imaging probe 100 is operably attached to PIM 200. RPL7a comprises a path length of 500 mm, and RPL7b comprises a path length of 300 mm, such that reference pathway 3250a comprises an overall path length of 7,531 mm, and reference pathway 3250b comprises an overall path length of 7,331 mm, thus matching sample pathways 3200a,b, respectively.

Using one, two, three or more optical switches and/or a multi-channel optical switch (e.g. a 64 or 128 channel optical switch) imaging assembly 300 can be configured to switch between several configurations of reference pathways, each comprising different optical properties, including length, NA, average fiber diameter, and other optical properties, such as GVD, such that imaging assembly 300 can optically match several different imaging probes 100. In some embodiments, the total number of reference pathway configurations can be less than the total number of imaging probe 100 configurations, such as when one reference pathway configuration can be configured to match more than one imaging probe configuration, for example when a delay line is included to compensate for the path length differences.

In some embodiments, optical core 110 comprises a dispersion shifted optical fiber, such as a depressed cladding dispersion shifted fiber. Optical core 110 can comprise an un-doped (e.g. a pure-silica) core, with a depressed cladding (i.e. a cladding with an index lower than the index of the core). The depressed cladding can be surrounded by a second, doped, cladding comprising a greater index than the un-doped core. Matching cable 336 can also comprise a dispersion shifted optical fiber, for example an optical fiber constructed and arranged similar to optical core 110, as described hereabove.

Figure 5A:
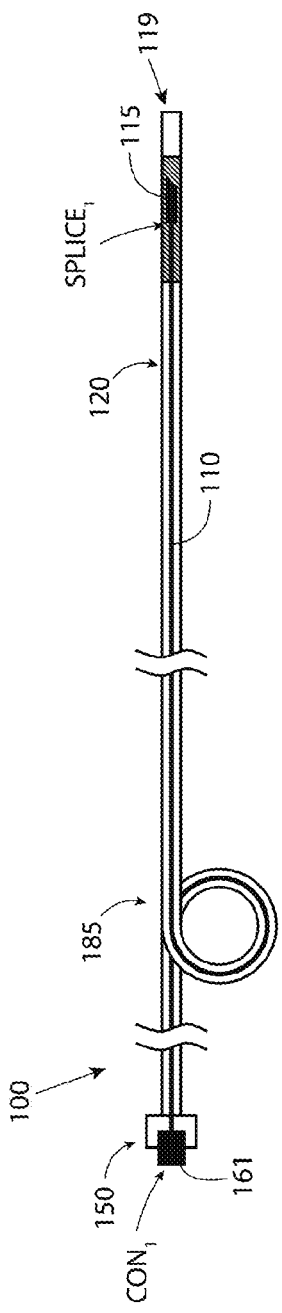
FIGS. 5A, 5B and 5C illustrate a side schematic view of an imaging probe, a side view of a lens assembly, and a representative system-produced image, respectively, consistent with the present inventive concepts.
Figure 5C:
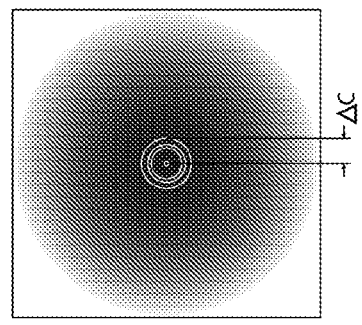
Figure 5B:
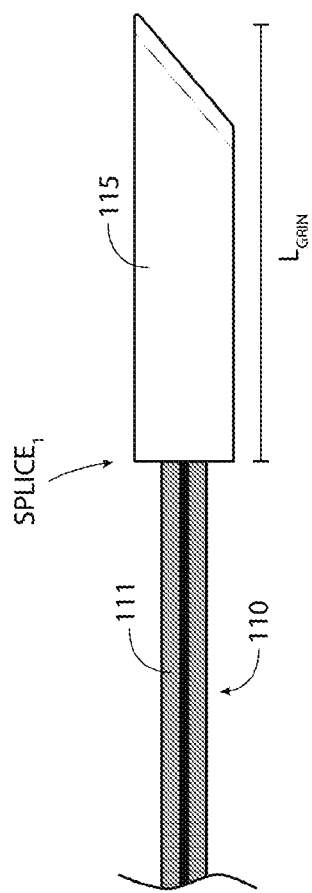

Referring now to FIGS. 5A, 5B, and 5C, a side schematic view of an imaging probe, a side view of a lens assembly, and a representative system-produced image are illustrated, respectively. Imaging probe 100 comprises a proximal connector assembly 150, operably attached to shaft 120 and optical core 110. Shaft 120 surrounds optical core 110. Imaging probe 100 can be of similar construction and arrangement to imaging probe 100 described herein. Connector assembly 150 comprises optical connector 161. Optical connector 161 is configured to form an optical connection with a mating optical connector (e.g. connector assembly 510 described hereabove), forming connection interface CONi. Optical core 110 is coupled to optical assembly 115 at connection point SPLICEi.

One or more connection interfaces and/or splices (e.g. CON" or SPLICE') within imaging probe 100 can comprise a "control surface", configured to cause a known amount of light to reflect proximally along optical sample path 3200 (e.g. a known back-reflection, as described hereabove in reference to FIG. 4). In some embodiments, the optical properties of optical assembly 115 and the optical properties of optical core 110 differ, such that SPLICE' comprises a control surface with known optical properties (e.g. based on the optical properties of the mating components). For example, optical core 110 can comprise a depressed cladding optical fiber (as described hereabove in reference to FIGS. 1 and 4), and optical assembly 115 can comprise a GRIN lens. The GRIN lens can comprise a shaped refractive index profile, wherein the refractive index at the center of the lens (the "center index" herein) is higher than at the periphery of the lens. In some embodiments, the center index comprises an index that is greater than the index of the core of optical core 110. For example, the center index of the GRIN lens can be approximately 0.01 to 0.05 higher than that of the core of optical core 110 (e.g. a depressed cladding optical core 110). Although small in absolute terms, the difference in index causes a relatively bright OCT reflection at SPLICE" as described herein. As shown in FIG. 5C, the reflections from the control surface at SPLICE' are detected by imaging assembly 300 as a consistent reflection at a distance AC from the origin. System 10 produces the cross-sectional images via rotation of optical assembly 115, and displaying line scans in a polar array, and as such, the reflection at distance ΔC is traced as a circle with radius ΔC. The reflection is displayed, for example at the display 56 of FIG. 1 as a ring AC from the origin (i.e. the center of the image) in FIG. 5C. The distance ΔC can be measured (e.g. by system 10) to assist in calibration of system 10 and/or diagnostics of system 10, as described herebelow in reference to FIG. 6 and FIG. 7, respectively.

In the embodiment of FIG. 5B, optical assembly 115 comprises a GRIN lens, which is optically attached to the distal end of optical core 110. Optical core 110 can comprise a core fiber surrounded by a cladding, cladding 111. Optical core 110 can comprise a non-zero dispersion shifted (NZDS) fiber, for example a fiber in which the dispersion of the fiber is shifted away from a natural dispersion zero of approximately 1300 nm. In these embodiments, imaging system 10 can be configured such that the system uses optically matched dispersion where the total dispersion of optical components of reference pathway 3250 matches the total dispersion of the optical components of sample pathway 3200, where sample pathway 3200 includes optical core 110 (e.g. aNZDS fiber). Alternatively or additionally, algorithm 51 can detect and numerically corrects any dispersion mismatches between console 50 and optical core 110. Dispersion matching and calibration of system 10 can be configured as described in reference to FIGS. 4 and 6 herein. Optical core 110 can comprise a fiber with a pure silica core, and a low index, or "depressed", cladding, cladding 111, as described hereabove. Optical core 110 can comprise a low bend loss fiber, such as a fiber with less than 5% transmission loss at a minimum radius of less than or equal to 6 mm, and/or less than 30% transmission loss at a minimum radius of less than or equal to 3 mm. Optical core 110 can also comprise a radiation resistant fiber, capable of maintaining its optical transmission properties after radiation exposure, such as exposure from a radiation-based sterilization process. In some embodiments, imaging probe 100 is sterilized using E-beam sterilization. In these embodiments, materials used in optical core 110 can be selected that are compatible with (e.g. not damaged by) E-beam sterilization. For example, optical core 110 can comprise an acrylate coating which is compatible with E-beam sterilization. Optical core 110 can comprise a single mode fiber similar to those used in telecommunication applications. Optical core 110 can comprise a diameter (e.g. a diameter including cladding) of less than 130 μm, such as a diameter less than 85 μm, such as a diameter of approximately 80 μm. In some embodiments, optical core 110 can comprise a single (non-tapered) diameter along at least a portion of the length of core 110 (e.g. at least the distal portion of core 110 comprises a single diameter), and/or along the entire length of core 110. Alternatively, at least a portion of core 110 can comprise a tapered diameter. In some embodiments, optical core 110 can comprise at least a first portion comprising an NZDS fiber, and at least a second portion comprising an optical fiber comprising differing optical properties (e.g. a non-shifted optical fiber). Optical core 110 can comprise an optical fiber with an outer diameter (e.g. including cladding) of less than or equal to 120 μm, such as less than or equal to 80 μm. In some embodiments, optical core 110 can comprise a silica core with a diameter of approximately 6 μm, a circumferential cladding with a thickness of approximately 37 μm, and a circumferential polyimide and/or acrylate coating, such as a coating with a thickness of approximately 10 μm. In some embodiments, optical assembly 115 comprises a material that is not radiation resistant, but comprises a length, $L_{GRIN}$, short enough that attenuation from radiation damage is negligible. For example, $L_{GRIN}$ can comprise a length of less than 5 mm, such as less than 2.5 mm, such as approximately 1 mm. In some embodiments, optical assembly 115 comprises a GRIN lens with a convex (e.g. cylindrical) distal surface as shown, and such as is further described herebelow in reference to FIGS. 8A and 8B. The internal reflection provided by the cylindrical distal surface can mitigate optical distortion caused by the lens effects of one or more sheaths surrounding optical assembly 115 during imaging, for example window 130 of shaft 120. In some embodiments, optical assembly 115 is constructed and arranged as described herebelow in reference to FIGS. 8A and 8B.

Figure 6:
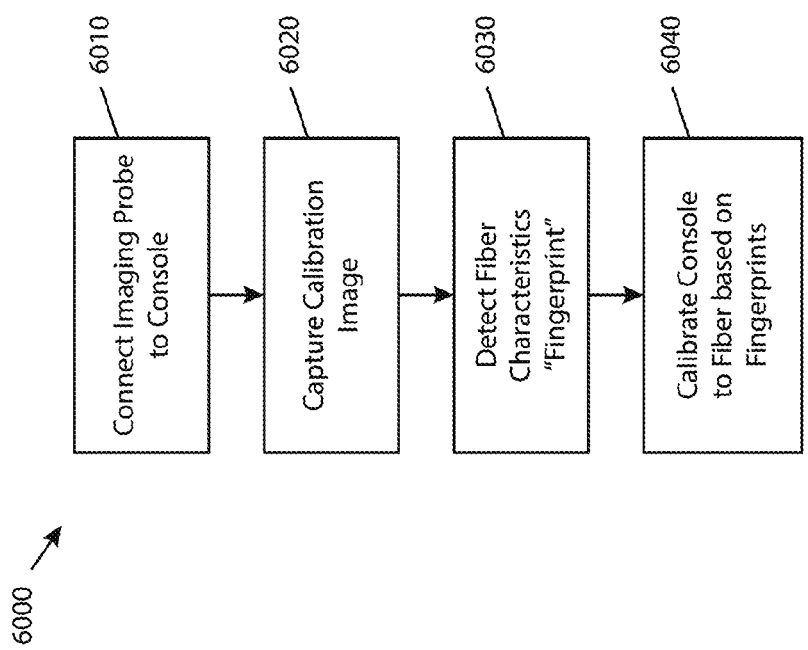
FIG. 6 illustrates a flow chart of a calibration method using a control surface, consistent with the present inventive concepts.

Referring now to FIG. 6, a flow chart of a calibration method using a control surface is illustrated, consistent with the present inventive concepts. Method 6000 of FIG. 6 is described using the devices and components of system 10 described hereabove and is configured to perform a calibration to align (i.e. match the lengths of) the optical path length of the reference and sample paths, such that accurate measurements of distances can be performed. OCT systems, such as system 10, produce high resolution images by using interferometry to accurately measure the time-of-flight difference between light travelling over a known distance (reference path 3250) and light travelling over an unknown distance (the sample path 3200 and the distance to be measured extending from optical assembly 115). Only the relative difference is measured; the absolute times are not measurable by this technique. It is essential to match the length of reference path 3250 to the length of sample path 3200 to accurately measure this relative difference.

Imaging probe 100 can comprise a length of fiber up to 3 meters long, and the fiber can be terminated with a micro-optic system at its distal end. The most practical reference path length can be matched to the length of the probe 100 optics such that distance measurements become relative to the distal tip. However, the sample arm fiber length is not fixed and varies with temperature and other influences. Thus it is desirable to accurately determine the actual, real-time, optical length of probe 100 such that the reference path length can be compensated, resulting in accurate distance determinations. To achieve this compensation, a control surface at the distal tip can be constructed to provide a known amount of return light (e.g. a known back reflection) that can be detected and measured by system 10 so that the reference path can be correspondingly adjusted. An NZDS fiber and GRIN lens interface (SPLICE) create an excellent control surface. For example, the length of the GRIN lens can be very tightly controlled, such that the distal optics tip location relative to the control surface is well-defined and constant. Also, the optical properties of the GRIN lens and the NZDS fiber can be very tightly controlled, so the reflection from the control surface interface will be consistent across different probe 100's. The index of the center of the GRIN lens can be relatively large compared to the index of the fiber (e.g. a pure silica core fiber). This configuration is in contrast to standard, doped-core fiber, where the index will be much closer to that of the GRIN lens. This index difference creates a proportionally larger reflection amplitude, enabling the reflection from the control surface to be differentiated from other reflections (e.g. reflections from the probe 100 sheath).

Alternatively, probe 100 can be constructed from standard fiber rather than an NZDS fiber, and the control surface reflection can be comparable or perhaps lower in amplitude than other reflections in the optical assembly of probe 100. In this configuration, the relationship between the various reflections can be used to determine the control surface and perform the calibration.

In Step 6010, an imaging probe, such as imaging probe 100 described herein, is operably attached to console 50, for example via patient interface module 200 and bus 58. Imaging probe 100 is operably connected to console 50 such that optical core 110 is optically coupled to imaging assembly 300 of console 50. In Step 6020, system 10 is configured to capture a calibration image, such as an image similar to the image shown in FIG. 5C. In some embodiments, light source 310 emits light energy to interferometer 320, which directs the light energy to both sample pathway 3200 and reference pathway 3250.

Photodetector 340 together with system 10 can be configured to detect differences in light reflected back along sample pathway 3200 and reference pathway 3250, such as to generate the calibration image (e.g. via processor 52). As described hereabove in reference to FIGS. 5A-C, imaging probe 100 can be constructed and arranged to produce a known, identifiable, reflection (e.g. a back-reflection) pattern, referred to herein as the "probe fingerprint".

In Step 6030, console 50 identifies a probe fingerprint associated with a particular configuration of imaging probe 100. In some embodiments, system 10 is configured to identify the probe fingerprint with or without optical core 110 being rotated (e.g. rotation of optical core 110 is not required for console 50 to identify the probe fingerprint). In some embodiments, imaging probe 100 comprises multiple control surfaces, such as two, three, four, or more control surfaces. Each control surface can reflect a known amount of light to create an identifiable pattern to be associated with a particular probe 100 fingerprint. The probe fingerprint can include data that correlates to values of one or more parameters of probe 100 (e.g. probe 100 type, probe 100 length, and the like). Values of each of these probe 100 parameters can be represented in the probe fingerprint by the reflection pattern (e.g. a single known surface reflection and/or a pattern of multiple surface reflections) and their relative spacings to each other as well as relative amplitudes.

In Step 6040, console 50 is calibrated based on the data extracted from the probe fingerprint. For example, console 50 can determine the distance from the origin to the probe fingerprint, and it can compare that distance (e.g. AC of FIG. 5C) to the expected distance for the attached imaging probe 100. If AC is determined to be different than the expected distance, delay line 332 of imaging assembly 300 can be adjusted, such as to lengthen and/or shorten reference pathway 3250, to properly calibrate console 50. In some embodiments, Steps 6020-6040 are repeated continuously and/or semi-continuously, such that the calibration of console 50 can be adjusted over time. For example, as components of system 10 change temperature (e.g. as optical core 110 heats up as imaging probe 100 is used in the body), the lengths of reference pathway 3250 and/or sample pathway 3200 can change over time, and Steps 6020-6040 can be repeated (e.g. automatically and/or manually).

Referring now to FIG. 7, a flow chart of a diagnostic method using a control surface is illustrated, consistent with the present inventive concepts. Method 7000 of FIG. 7 is described using the devices and components of system 10 described hereabove. In Step 7010, system 10 begins monitoring the integrity (e.g. acceptable operation) of an imaging probe 100 attached to PIM 200 and/or console 50 (e.g. to console 50 via PIM 200). Console 50 can confirm the integrity of imaging probe 100 (e.g. optical core 110 of imaging probe 100) by detecting the probe fingerprint as described hereabove in reference to FIGS. 5A-C and 6. In Step 7020, if the integrity of imaging probe 100 is confirmed, and the probe fingerprint and/or control surface is detected, imaging probe 100 can be introduced into the patient. In Step 7030, imaging probe 100 can be advanced through the patient vasculature (e.g. advanced to the heart or the brain of the patient). As described hereabove, the probe fingerprint of imaging probe 100 can be detected without having to rotate optical core 110, such that imaging probe 100 can be advanced through the patient vasculature while being monitored for an integrity failure without having to rotate optical core 110.

In Step 7040, a check of probe 100 integrity (e.g. proper operation) is performed. If an integrity failure is detected, Step 7045 is subsequently performed and system 10 enters an "alert mode." If an integrity failure is not detected and the advancement is complete, Step 7050 is performed and system 10 enters an "image ready mode." If not fully advanced, Steps 7030 and 7040 are repeated as imaging probe 100 is fully advanced to a target location for imaging. In Step 7040, an integrity failure (e.g. an undesired state) can be determined if the probe fingerprint detection is "lost" or otherwise deemed deficient, for example indicating a potential fracture of optical core 110. Additionally or alternatively, the probe fingerprint may change, such as a change that is beyond an expected threshold, indicating a structural or other integrity failure of imaging probe 100 is present. In some embodiments, Steps 7030 and 7040 are continuously repeated during an imaging procedure (e.g. Steps 7030 and 7040 are not limited to an advancement procedure), such that system 10 can detect an integrity failure at any point during its use. When in an alert mode, system 10 can provide a visual and/or an audible alert to a user indicating that an integrity failure has been detected. In some embodiments, an alert mode can be "cleared" by disconnecting the first imaging probe 100 and replacing a second (new) imaging probe 100. Additionally or alternatively, the first imaging probe 100 can be removed from the patient to correct and/or clear an error, for example if the failure is non-critical (e.g. a non-critical kink that does not damage imaging probe 100). Upon correction and/or clearance of the error, imaging probe 100 can be reconnected with system 10 and successfully used in an imaging procedure.

Figure 8A:
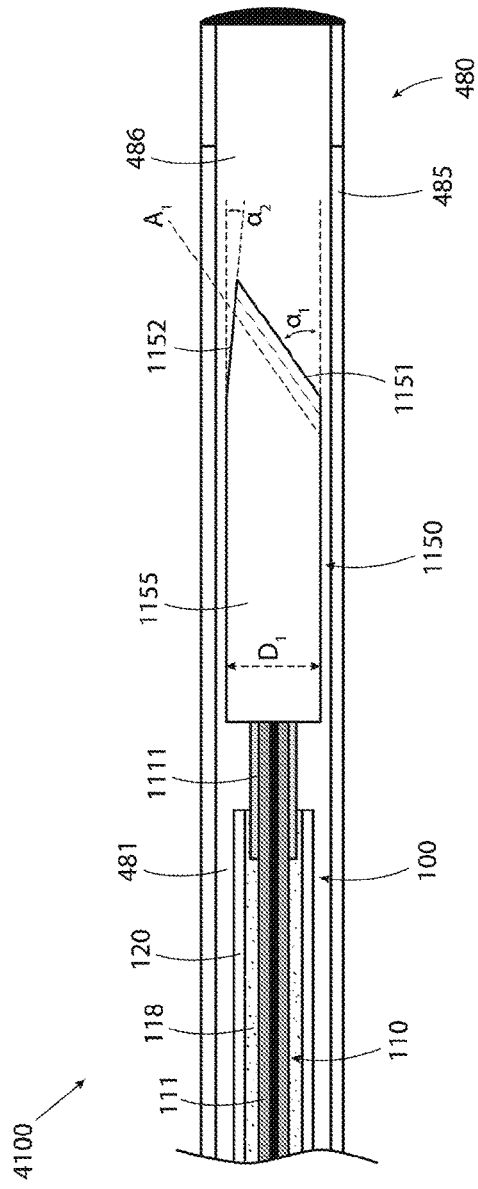
FIGS. 8A and 8B illustrate side sectional views of the distal ends of embodiments of an imaging probe assembly, consistent with the present inventive concepts.
Figure 8B:
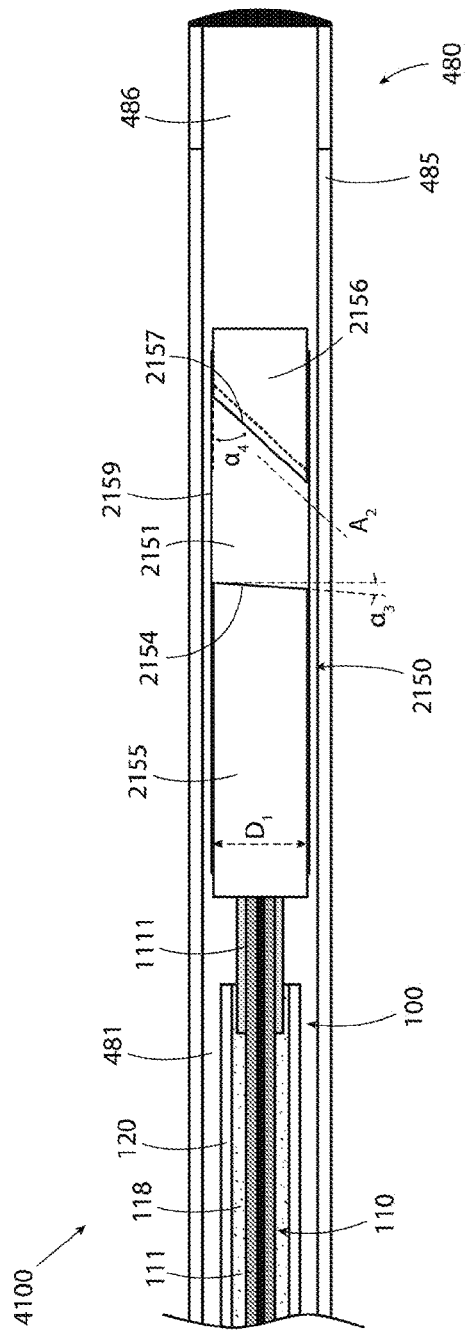

Referring now to FIGS. 8A and 8B, side sectional views of the distal ends of embodiments of an imaging probe assembly are illustrated, consistent with the present inventive concepts. Catheter assembly 4100 comprises imaging probe 100 slidingly and rotatably received within a lumen 481 of delivery catheter 480, as described hereabove in reference to FIG. 1B. Delivery catheter 480 comprises an optically transparent segment, window 485. Window 485 is positioned at a distal portion of delivery catheter 480 and comprises a material transparent to imaging modalities utilized by imaging probe 100. In the embodiments shown, optical core 110 extends beyond the distal end of shaft 120, into lumen 481. The distal portion of lumen 481 defines a chamber 486. An optical assembly is attached to (and optically coupled to) the distal end of optical core 110, distal to shaft 120, within chamber 486. In FIG. 8A optical assembly 1150 is illustrated, and in FIG. 8B optical assembly 2150 is illustrated. As shown, the attached optical assembly 1150, 2150 can comprise a diameter Di. Diameter Di can be greater than the inner diameter of shaft 120, as shown. In some embodiments, a strain relieving element, sleeve 1111, surrounds at least a distal portion of optical core 110, for example a portion proximate the distal end of shaft 120. Sleeve 1111 can be configured to provide a stabilizing force to optical core 110 and/or the attached optical assembly 1150, 2150. In some embodiments, sleeve 1111 also surrounds a portion of the optical assembly 1150, 2150 to reinforce the union between optical core 110 and the attached optical assembly 1150, 2150. Additionally or alternatively, sleeve 1111 is adhered (e.g. with an adhesive) to at least the proximal portion of the optical assembly 1150, 2150. Sleeve 1111 can comprise a polyimide or other polymer sleeve.

As described hereabove in reference to FIG. 1, a dampening gel 118 surrounds at least a portion of optical core 110 within the distal portion of shaft 120. In some embodiments, the distal end of shaft 120 is not sealed to prevent leakage of gel 118 from shaft 120, but rather the relative dimensions of the components and the viscosity of gel 118 limit migration from shaft 120. Alternatively or additionally, an O-ring (not shown) and/or other sealing element can be included (e.g. at the distal end of shaft 120) to prevent migration of gel 118 from the distal end of shaft 120. In some embodiments, catheter assembly 4100 is configured as a disposable assembly, intended for a single use (e.g. for a single patient) over a limited period of time (limited operative life). In these embodiments, the rate of migration of gel 118 from shaft 120 can be sufficiently slow to remain functional (e.g. remain in place) during the operative life of catheter assembly 4100. In some embodiments, gel 118 can comprise a static viscosity sufficiently high to prevent migration while in the static state. Gel 118 migration during a dynamic condition can be minimal since the dynamic condition only lasts for short periods of time (e.g. less than 10 seconds).

In FIG. 8A, optical assembly 1150 comprises a GRIN lens 1155, operably attached (e.g. optically coupled and affixed) to the distal end of optical core 110. GRIN lens 1155 comprises a beveled reflective surface, surface 1151. Surface 1151 can comprise a convex polish, configured to attenuate the reflected light to compensate for distortion caused as light passes through the curved wall of window 485. For example, surface 1151 can comprise a convex cylindrical profile having an axis $A_1$, as shown (e.g. the convex profile comprises a single radius of curvature). The cylindrical profile can comprise a radius of approximately 0.5 mm. Surface 1151 can be created (e.g. cut and/or polished into GRIN lens 1155) at an angle $\alpha_1$, as shown. Angle $\alpha_1$ can comprise an angle between 30° and 47°, for example between 35° and 47°, such as approximately 40°. In some embodiments, to ensure total internal reflection, such as for a glass-gas interface (e.g. glass-air interface), angle $\alpha_1$ comprises an angle no greater than 47°, such that the angle of incidence of the light traveling through optical core 110 is greater than 43°, the critical angle for total internal reflection. In some embodiments, angle $\alpha_1$ comprises an angle not equal to 45°, such that reflected light is not perpendicular to the wall of window 485, avoiding unwanted reflections from being captured by the fiber. For example, when angle $\alpha_1$ equals 40°, light reflects off surface 1151 at a forward angle of 10°. Any reflections from the wall of window 485 will reflect forward, away from GRIN lens 1155. In some embodiments, GRIN lens 1155 comprises a second beveled surface, surface 1152. Surface 1152 is created (e.g. cut and/or polished) into the top convex surface of GRIN lens 1155 (a cylindrical extrusion), to create a flat portion for light to enter and/or exit GRIN lens 1155 without cylindrical distortion. Surface 1152 can be created at an angle $\alpha_2$. Angle $\alpha_2$ can comprise an angle of approximately 5°, such as an angle greater than 1°.

In some embodiments, chamber 486 is filled with a fluid (e.g. one or more gases, such as air) with an index of refraction that provides total internal reflection for surface 1151. Alternatively or additionally, a metalized finish can be applied to surface 1151 to provide a reflective surface, independent of surface interactions between materials (e.g. independent of the optical refraction between material). In some embodiments, during a manufacturing process, surface 1151 is created, after which a metallic coating is applied. After the metallic coating is applied, surface 1152 is created, removing any metallic "overspray" from the existing top convex surface of GRIN lens 1155.

In FIG. 8B, optical assembly 2150 comprises a GRIN lens 2155, operably attached (e.g. optically coupled and affixed) to the distal end of optical core 110. Positioned distal (e.g. opposite) to GRIN lens 2155, a reflector 2156 is operably attached to GRIN lens 2155 via a tube 2159. Tube 2159 can comprise PET. Tube 2159 defines a chamber 2151 between GRIN lens 2155 and reflector 2156. Reflector 2156 comprises a beveled, reflective surface, surface 2157. Surface 2157 can comprise a concave polish, configured to attenuate the reflected light to compensate for distortion caused as light passes through the curved wall of window 485 and/or the curved wall of tube 2159. For example, surface 2157 can comprise a concave cylindrical profile having an axis $A_2$, as shown (e.g. the concave profile comprises a single radius of curvature). The cylindrical profile can comprise a radius of approximately 1 mm. Surface 2157 can be created (e.g. cut and/or polished into reflector 2156) at an angle $\alpha_4$, as shown. Angle $\alpha_4$ can comprise an angle between 30° and 60°, for example between 35° and 45°, such as 40°. Reflector 2156 can comprise a material comprising at least one of a metal (e.g. a wire segment) or a plastic, such as a plastic with a metallic coating on surface 2157. In some embodiments, the distal surface of GRIN lens 2155, surface 2154, can be created at an angle $\alpha_3$. Angle $\alpha_3$ can comprise an angle between 1° and 10° degrees, such as between 5° and 8°, such as an angle greater than 5°. Angle $\alpha_3$ can be configured to prevent unwanted back reflection caused by a 0° surface 2154. By separating the spherical focusing element (i.e. GRIN lens 2155) and the cylindrical compensating element (i.e. reflector 2156), two fairly simple components can be fabricated rather than single complex, aspherical element. Further, for most practical applications, the light exiting the GRIN is very nearly collimated (weakly converging) and thus the distance between the GRIN and mirror is not very critical, simplifying assembly.

Figure 9:
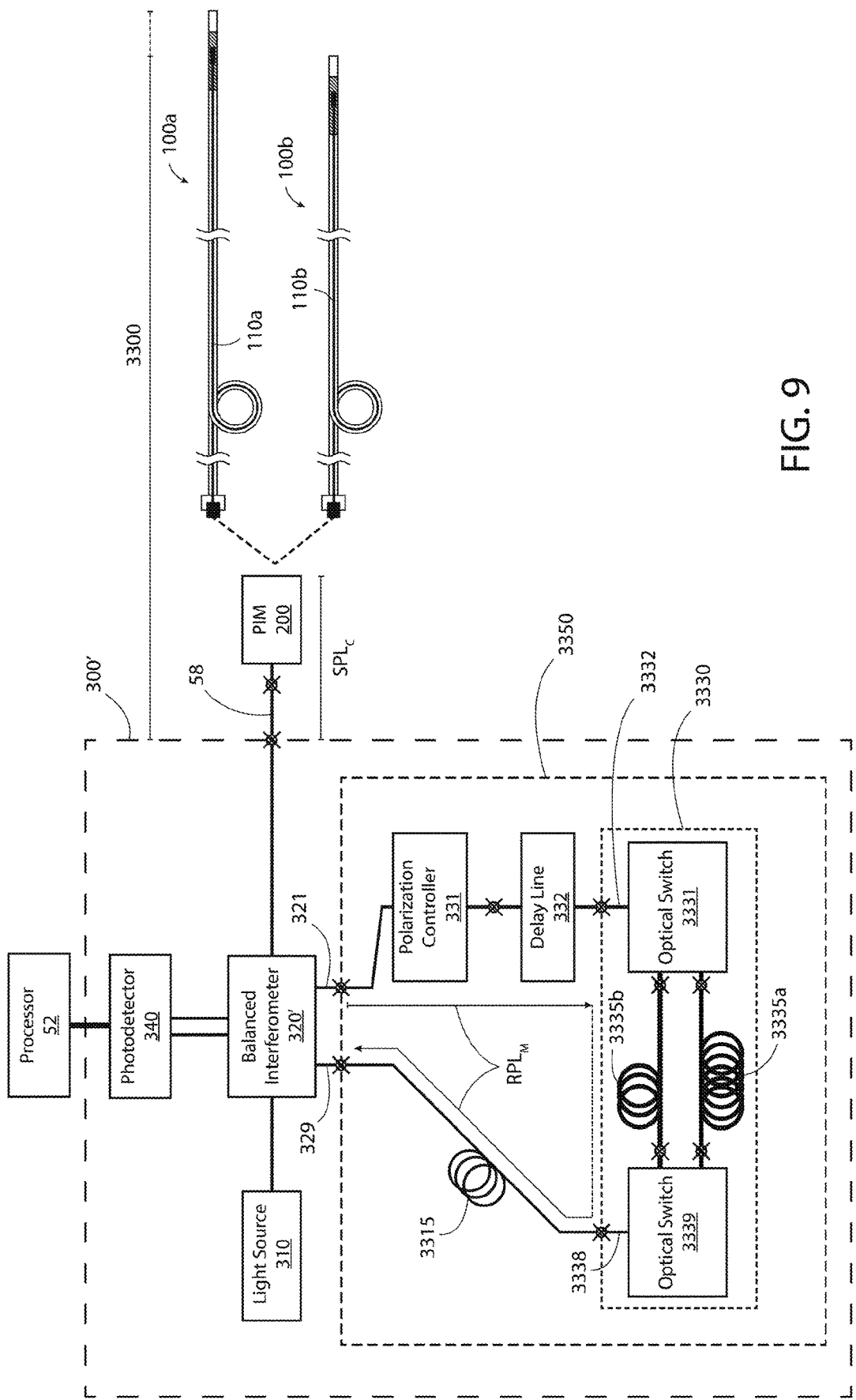
FIG. 9 illustrates a schematic view of an optical pathway of an imaging system, consistent with the present inventive concepts.

Referring now to FIG. 9, a schematic view of an optical pathway of an imaging system is illustrated, consistent with the present inventive concepts. Imaging system 10 can comprise an imaging assembly comprising a transmissive reference path. As described hereabove in reference to FIG. 4, a reflective reference path terminates in a reflector configured to redirect light traveling from an interferometer back to the interferometer. In FIG. 9, the transmissive reference path attaches at both ends to the interferometer. In this embodiment, the reference path is twice the length of the sample path, to match the total time of flight of light traveling distally, reflecting, and returning proximally along the sample path.

Imaging assembly 300' can comprise one or more components similar to imaging assembly 300 of FIG. 4, including light source 310 and photodetector 340. Imaging assembly 300' can comprise a balanced interferometer 320'. Interferometer 320' can be configured for transmissive reference, comprising a reference output 321 and reference input 329. A reference pathway 3350 optically couples output 321 to input 329. Reference pathway 3350 can comprise one or more components similar to reference pathway 3250 of FIG. 4, including polarization controller 331 and delay line 332. Reference pathway 3350 can further comprise a path switching assembly 3330. Switching assembly 3330 can comprise two optical switches, input switch 3331 and output switch 3339. Each switch 3331,3339 can comprise a many-to-one switch (e.g. two or more to one). For example, switching assembly 3330 can comprise a single input 3332 and single output 3338. Alternatively or additionally, output switch 3339 can comprise a passive coupler, such as a 2:1 or 3:1 passive coupler. In these embodiments, a percentage of the light from each input path (e.g. 3335*a* and 3335*b*) would be lost before entering path 3338 (e.g. approximately 50% for a 2:1 passive coupler). Interferometer 320' can be configured to tolerate this loss in the reference arm. As shown in FIG. 9, delay line 332 can be optically coupled to input 3332 of switching assembly 3330, and an optical fiber 3315 can complete reference pathway 3350, optically coupling output 3338 of switching assembly 3330 to reference input 329 of interferometer 320'.

Switching assembly 3330 can comprise two or more optical cables optically coupling the outputs of switch 3331 to the inputs of switch 3339, cables 3335*a,b* shown. Each cable 3335 can comprise a unique set of characteristics, for example length and/or optical properties such as dispersion. The properties of each cable 3335 can be selected to match the properties of an optical core of an imaging probe configured for use with imaging assembly 300'. For example, a first imaging probe 100*a* can comprise a 170 cm optical core 110*a* with an NA of 0.16, and a first cable 3335*a* can comprise a length of 340 cm and can comprise a matched NA of 0.16. Switching assembly 3330 can be configured to select cable 3335*a* (e.g. optically couple cable 3335*a* between input 3332 and output 3338) when imaging probe 100*a* is used with imaging assembly 300'. A second imaging probe 100*b* can comprise an optical core 110*b* comprising one or more dissimilar optical properties to first optical core 110*a*. A second cable 3335*b* can comprise matching optical properties, and a length that is twice the length of optical core 110*b*. In this transmissive configuration, cable 3335*b* comprises a length twice that of the matched optical core 110*b*, such as to match the total flight time through cable 3335*b* to the total flight time through the optical core 110*b* (e.g. transmitted and reflected flight time).

PIM 200 can be optically coupled to imaging assembly 300' via bus 58, the optical path length of bus 58 and the optical components of PIM 200 comprising path length $SPL_C$. Sample path length 3300 comprises both path length $SPL_C$ and the length of an attached optical core 110. The components of reference pathway 3350, excluding switch assembly 3330, comprise a path length $RPL_M$. The length of optical fiber 3351 can comprise a length selected such that path length $RPL_M$ equals twice the length of path length $SPL_C$. The components and optical fibers of polarization controller 331, delay line 332, cable 3315, bus 58, and PIM 200 can comprise similar optical properties, for example standard optical properties of components typically used in optical telecommunications.

Referring now to FIGS. 10, 10A-D, 10E-G, and 10H, an exploded view, four assembly views, a partial sectional view, a partially exploded view, a perspective view, and a simplified sectional view of a connector assembly are illustrated, respectively, consistent with the present inventive concepts. Connector assembly 150 can be operably attached to the proximal end of an optical probe, such as imaging probe 100, as described herein. Connector assembly 150 can operably attach (e.g. optically and mechanically attach) imaging probe 100 to a rotating fiber optic connector (e.g. a standard Fiber Optic Rotary Joint, FORJ). Connector assembly 150 comprises a fiber optic connector 161 that operably engages a mating connector and maintains a optical connection. In some embodiments, fiber optic connector 161 comprises a commercially available fiber optic connector, such as a SC/APC fiber optic connector, such as those that are commonly used in telecommunication networks. In these embodiments, and as described herein, connector assembly 150 can comprise one or more components that operably engage, manipulate, and/or maintain the relative position and orientation of fiber optic connector 161 within connector assembly 150. Connector assembly 150 can include one or more alignment components, as described herebelow, that operably attach to a rotation assembly, such as rotation assembly 500 described herein, while maintaining the rotational orientation of fiber optic connector 161 relative to rotation assembly 500 during attachment and/or detachment. Connector assembly 150 can comprise numerous forms of connectors, such as a bayonet or other locking connector. The following describes a bayonet-type connector that provides the necessary forces and constraints to make and maintain a connection between imaging probe 100 and rotation assembly 500. Connector assembly 150 and/or rotation assembly 500 can be of similar construction and arrangement to similar components described in applicants co-pending International PCT Patent Application Serial Number PCT/US2018/062766, titled "IMAGING SYSTEM", filed Nov. 28, 2018, the content of which is incorporated herein by reference in its entirety for all purposes.

Connector assembly 150 comprises a rotating assembly 160, a locking assembly 170, and a housing, connector body 151, surrounding at least a portion of rotating assembly 160 and locking assembly 170. Connector assembly 150 can include a protective covering, skirt 154. Skirt 154 can provide a seal between connector assembly 150 and connector assembly 510 of patient interface module 200, as described herein, such as to prevent ingress of contaminates into housing 201 of patient interface module 200. Rotating assembly 160 comprises optical connector 161. In some embodiments, optical connector 161 comprises a connector requiring proper rotational alignment with a mating optical connector, such as optical rotary joint 550 of rotation assembly 500 described herein. Connector assembly 150 can be constructed and arranged to provide the proper alignment between the two connectors (e.g. when connecting and/or disconnecting) without the need for an additional alignment step, such as to obviate the need for any user (e.g. manual) alignment step and/or system 10 driven (e.g. automatic) alignment step. Optical connector 161 further comprises a coupling shaft, shaft 169. Optical connector 161 (including coupling shaft 169) slidingly receives the proximal end of optical core 110 and torque shaft 105 (not shown). Torque shaft 105 and/or optical core 110 can operably attach to optical connector 161 (e.g. via coupling shaft 169), such that rotational force is applied to torque shaft 105 and/or optical core 110 by optical connector 161 (e.g. rotation of optical connector 161 causes the rotation of torque shaft 105 and/or optical core 110). In some embodiments, shaft 169 can comprise a flexible shaft, such as is described in detail herebelow in reference to FIG. 10H. Additionally or alternatively, torque shaft 105 and/or optical core 110 can operably attach to connector 161 as described herebelow in reference to FIG. 10H.

In some embodiments, rotating assembly 160 is configured to rotate optical core 110 in a single direction (unidirectionally). Alternatively, rotating assembly 160 is configured to rotate optical core 110 in either direction (bidirectionally). The proximal end of optical core 110 is positioned within optical connector 161 such that the proximal end of optical core 110 is aligned with the proximal end of connector 161, forming a first optical transmission surface 161a, configured to abut a second optical transmission surface 555 (e.g. of a mating optical connector), to form an optical connection. In some embodiments, the first and second optical transmission surfaces 161a, 555, can each comprise a bevel, such as to increase the amount of light transmitted thru the connection. Optical connector 161 can comprise a non-circular shape (e.g. a rectangular shape as shown), with an asymmetric profile, such that optical connector 161 can only mate with a second connector in a particular, aligned orientation (e.g. such that the beveled optical transmission surfaces are properly aligned). Rotating assembly 160 includes a circular housing, carrier 163, and a locking connector, clip 162, configured to fixedly maintain optical connector 161 within carrier 163, such as is shown in FIGS. 3A and 3B, two assembly views of rotating assembly 160. Carrier 163 comprises a first radial recess, slot 164, and one or more alignment recesses, holes 165. Carrier 163 and/or clip 162 can comprise one or more reliefs (e.g. openings, slots and/or recesses) and/or projections sized and positioned to rotationally balance rotating assembly 160. These reliefs and/or projections can be configured to offset any rotational imbalances of optical connector 161 or other component of rotating assembly 160 (e.g. optical connector 161 can be an unbalanced connector). When fully assembled, rotating assembly 160 is rotationally balanced such as to limit vibration or other adverse effects of an imbalanced load at high rotational speeds.

Locking assembly 170 comprises: a housing; rotational lock 171; a retention mechanism, connector retainer 175, comprising one or more retention elements; projections 176; and a biasing element, locking spring 179.

Figure 10:
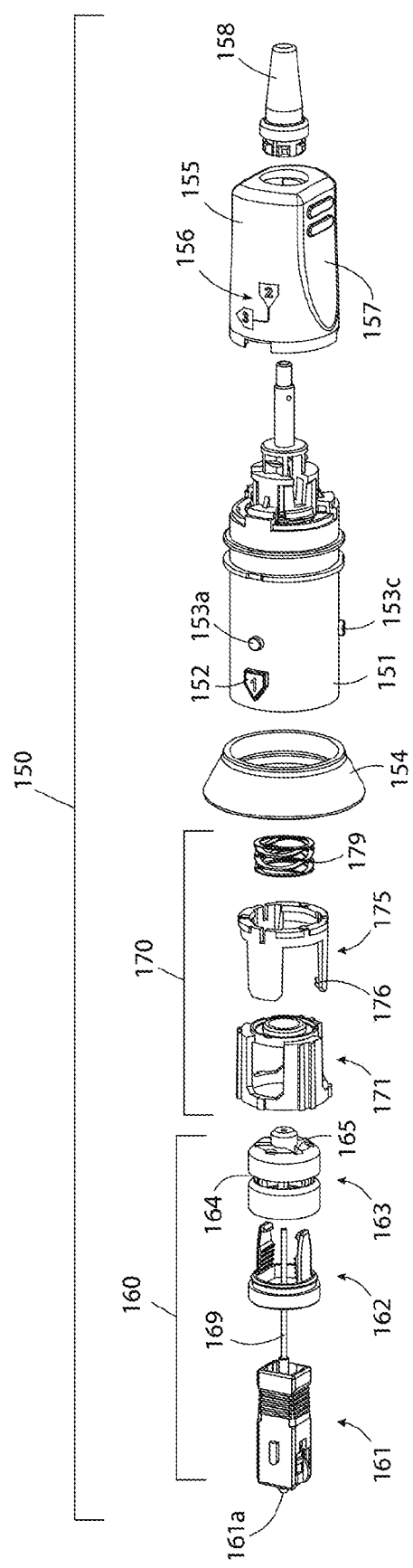
FIGS. 10 and 10A-H are various views of a connector assembly, consistent with the present inventive concepts.
Figure 10B:
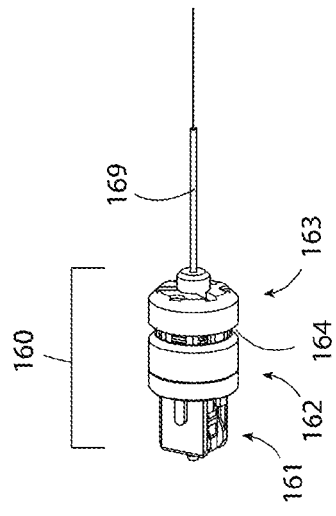
Figure 10D:
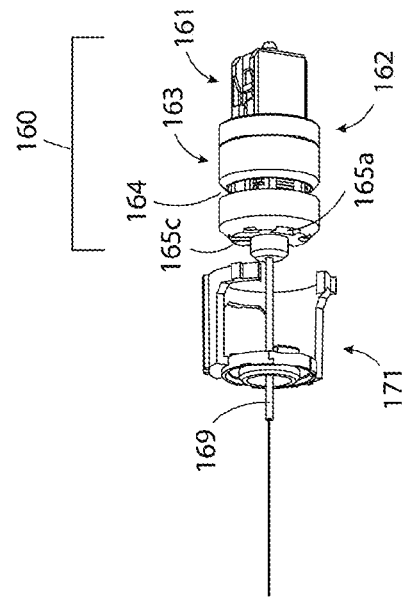
Figure 10A:
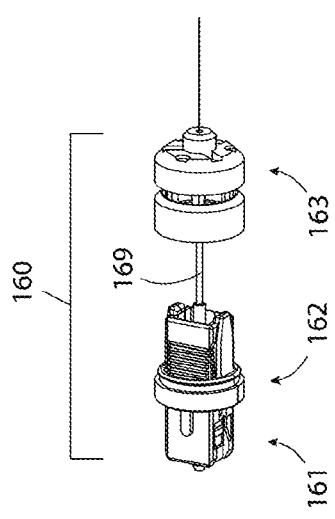
Figure 10C:
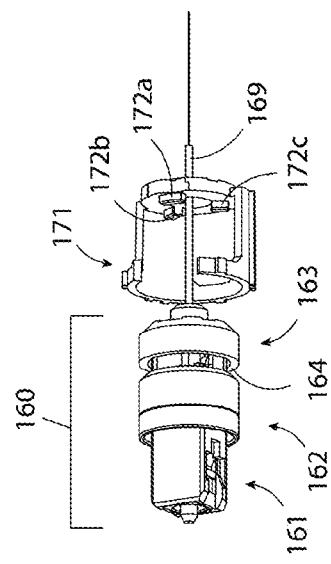

Referring to FIGS. 10C and 10D, opposing, partial sectional views of a portion of connector assembly 150 are illustrated. Rotational lock 171 comprises one or more projections, locking teeth 172 (three teeth 172a-c shown). Rotating assembly 160 is slidingly received within rotational lock 171, such that locking teeth 172a-c slidingly engage holes 165 of carrier 163 (165a and 165c shown, with 165b positioned opposite projection 172b), when rotating assembly 160 is fully inserted within rotational lock 171. This engagement locks the rotational orientation between rotational lock 171 and rotating assembly 160. In some embodiments, locking teeth 172 comprises an asymmetric pattern, and holes 165 comprise a matching asymmetric pattern, such that there is a single rotational orientation in which carrier 163 can be fully engaged within rotational lock 171 (e.g. hole 165a and projection 172a are sized to mate exclusively). Alternatively or additionally, rotational lock 171 can comprise a friction plate for frictionally engaging carrier 163. Connector retainer 175 is positioned about rotational lock 171 and carrier 163 (e.g. slidingly positioned about rotational lock 171 and carrier 163 in an assembly process), such that projections 176 are captured within slot 164, preventing rotating assembly 160 from exiting rotational lock 171. Slot 164 can comprise a width greater than the width of projection 176, such that rotating assembly 160 can travel longitudinally (e.g. axially) within rotational lock 171. For example, rotating assembly 160 can travel proximally such that locking teeth 172 disengage from holes 165 (e.g. rotational lock 171 can travel distally relative to rotating assembly 160 when a force is applied to rotational lock 171 as described herebelow). Projections 176 can operably engage the distal edge of slot 164, preventing rotating assembly 160 from exiting rotational lock 171. Additionally, carrier 163 can travel distally from the proximal most position, such that locking teeth 172 engage holes 165, and the distal end of carrier 163 abuts the back wall of rotational lock 171.

Figure 10G:
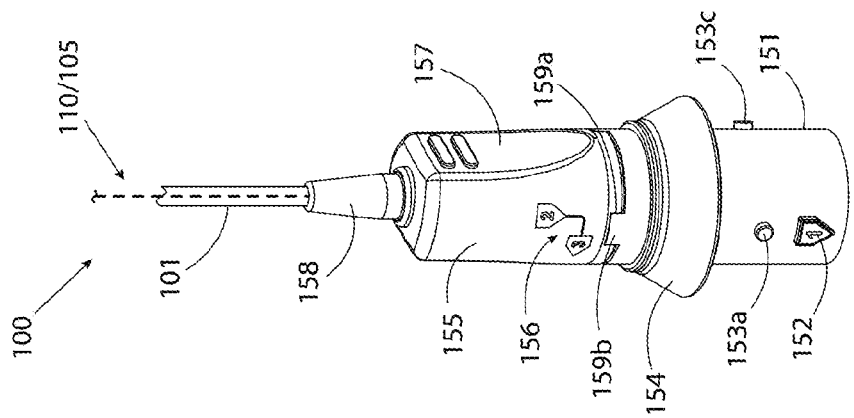
Figure 10F:
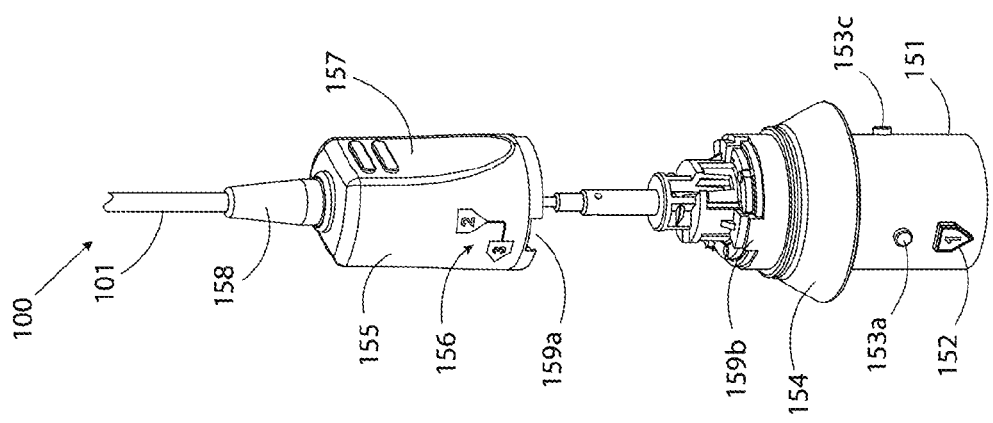
Figure 10E:
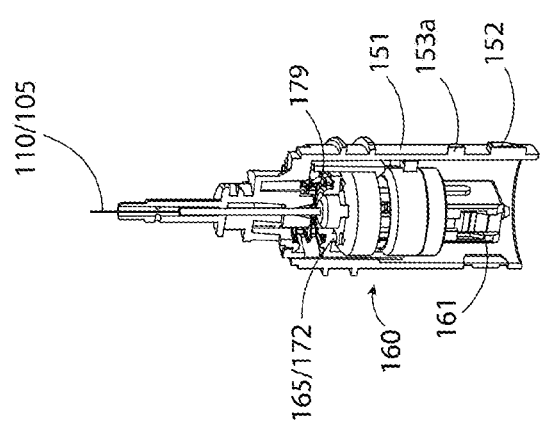

Referring to FIGS. 10E-G, rotating and locking assemblies 160, 170 shown are slidingly received within connector body 151. Locking assembly 170 is rotationally fixed within connector body 151. Rotating assembly 160 is rotationally fixed to locking assembly 170 when locking teeth 172 are engaged with holes 165, and therefore also fixed to connector body 151; otherwise rotating assembly 160 is free to rotate within connector body 151. In some embodiments, connector retainer 175 is fixedly positioned within connector body 151, and rotational lock 171, as well as rotating assembly 160 "float" within connector body 151, relative to connector retainer 175. Rotating assembly 160 is "captured" by connector retainer 175, such that it is allowed to rotate and travel longitudinally, as described hereabove, between a proximal-most location (where projections 176 engage slot 164) and a distal-most location (where the distal end of rotating assembly 160 abuts rotational lock 171). Connector assembly 150 can further comprise a biasing element, spring 179, configured to bias one or more components of connector assembly 150, such as when connector assembly 150 is not connected to a mating connector. For example, spring 179 can be positioned between a portion of connector body 151 and rotational lock 171, biasing rotational lock 171 distally against rotating assembly 160. Rotating assembly 160 is in turn biased against connector retainer 175 in its proximal-most position. This biased arrangement can prevent disengagement of locking teeth 172 from holes 165, maintaining the relative rotational orientation between rotating assembly 160 and connector body 151, while connector assembly 150 is not connected to a mating connector. Alternatively or additionally, when connector assembly 150 is connected to a mating connector, spring 179 can bias connector body 151 "out of" the mating connector, helping to facilitate one or more interlocking mechanisms, as described herebelow in reference to FIGS. 6A-D.

Connector body 151 includes one or more projections for alignment and engagement with a mating connector. As shown, connector body 151 comprises a first projection, alignment marker 152, configured to visually and operably align connector assembly 150 to a mating connector, as described herebelow in reference to FIGS. 4A through 6D. Alignment marker 152 can indicate the "top" of connector body 151, and it can be rotationally aligned with the "top" of optical connector 161, for example when optical connector 161 is rotationally locked relative to connector body 151 via rotational lock 171. Connector body 151 can further include one, two or more locking projections, projections 153*a* and 153*c* shown (projection 153*b* not shown but positioned behind connector body 151). Connector assembly 150 can further comprise a second body portion, cover 155. Cover 155 can comprise one or more mating elements, recess 159*a* shown, configured to properly align cover 155 to connector body 151 by aligning with one or more mating elements of connector body 151, projection 159*b* shown. Cover 155 can include instructional markings, markings 156, and one or more depressed, contoured, or otherwise ergonomic portions, grips 157. Grips 157 can be constructed and arranged such that a user can naturally grasp connector assembly 150, align connector assembly 150 with a mating connector (e.g. while using markers 152 and 156 for alignment and instruction), and insert and twist connector assembly 150 to secure the connection. Markings 156, along with marking 152 can indicate to the user the steps for engaging connector assembly 150 to a mating connector, for example, insert, push, and turn.

Connector assembly 150 can further include an element configured to reduce strain between connector 150 and one or more components of imaging probe 100, strain relief 158. As shown, imaging probe 100 comprises an outer proximal shaft, outer shaft 101, surrounding at least optical core 110 and torque shaft 105. Strain relief 158 slidingly receives outer shaft 101, which is fixedly attached to connector assembly 150. Optical core 110 and torque shaft 105 are free to rotate within outer shaft 101.

Figure 10H:
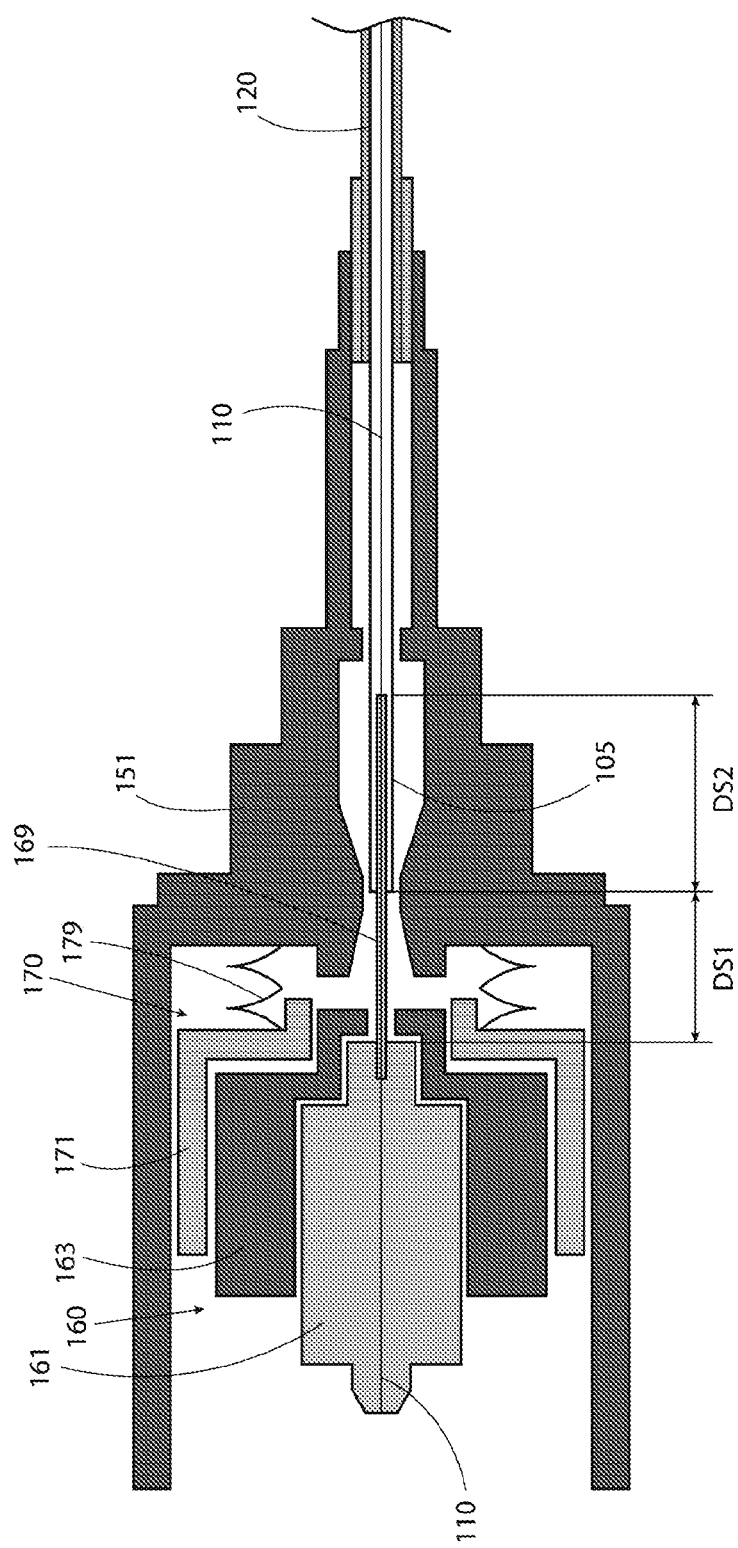

Referring now to FIG. 10H, a simplified sectional view of connector assembly 150, is illustrated. Rotating assembly 160 and locking assembly 170 are shown positioned within a portion of connector body 151. Optical connector 161 is shown positioned within carrier 163, which is positioned within locking assembly 170. Shaft 169 is shown extending distally (to the right of the page) from optical connector 161. Shaft 169 surrounds at least a proximal portion of optical core 110, and shaft 169 extends distally through connector body 151. Torque shaft 105 surrounds and operably attaches to at least the distal portion of shaft 169, as shown. Torque shaft 105 extends distally into, and is rotatable within, shaft 120. Shaft 169 and torque shaft 105 are operably connected such that shaft 169 transmits rotational forces from rotating assembly 160 to torque shaft 105. The proximal end of torque shaft 105 can be located a distance DS1 from the distal end of optical connector 161, such that a length of shaft 169 (distance DST) is exposed and free to bend within connector body 151. Distance DS1 can comprise a distance of no more than 25 mm, such as a distance of approximately 5 mm. In some embodiments, when shaft 169 is supported (e.g. positioned within a second flexible tube), DS1 can comprise a distance greater than 25 mm. Shaft 169 can extend a distance DS2 into torque shaft 105. Distance DS2 can comprise a distance of at least 2 mm.

Shaft 169 can comprise a diameter configured to transmit sufficient torque to torque shaft 105 (e.g. proportional to the diameter) with a sufficiently low stiffness to reduce undesired vibration of optical connector 161 during rotation of optical core 110 (e.g. proportional to the diameter to the fourth power). Shaft 169 can comprise a diameter of no more than 0.025", such as a diameter of no more than 0.022", 0.018", 0.016" and/or 0.014" (e.g. a diameter of approximately 0.014"). Shaft 169 can comprise a flexible construction, such as when shaft 169 comprise a material or other construction parameter that prevents or at least reduces undesired vibration of optical connector 161 during rotation of optical core 110. In some embodiments, shaft 169 comprises a rigid shaft, and connector assembly 150 is heavily constrained via tight-tolerance bearings and similar components. However, this introduced an unexpected and undesirable effect. The purpose of optical connector 161 is to allow the optical core 110 (e.g. the proximal end of which is mounted within a high-precision ferrule of optical connector 161) to butt against a matching core and ferrule assembly of connector assembly 510 with a very high centering accuracy, such that the very small cores (~6-10 um) are held in tight alignment and close physical contact to form a low-loss optical connection between two opposing fiber faces. This connection defines the an optical axis. However, the mechanical central or rotational axis of connector 161 is not constrained to align perfectly with the optical axis. Hence, under rotation there can be a slight wobble between the two axes. By constraining shaft 169 (e.g. a rigid shaft 169) within mechanically centered bearings this wobble and/or vibrational energy can appear at the proximal end of core 110, causing the two opposing fiber faces to move relative to one another. At high speeds, where the forces increase with the square of the rotation speed, this relative movement between the opposing fiber faces can cause damage to the fibers, and/or otherwise negatively affect the imaging ability of system 10. By allowing shaft 169 to be flexible and unconstrained, this vibrational energy is absorbed and/or dissipated in shaft 169, and the vibrational energy is minimized at the fiber face. Shaft 169 can comprise one, two, or more materials selected from the group consisting of: a plastic material; a rubber material; a polymer material; polyimide; and combinations of two or more of these. Shaft 169 can comprise a wall thickness of no more than 0.006", such as a wall thickness of approximately 0.003". In some embodiments, shaft 169 can comprise a stiffness less than the stiffness of the connection between optical connector 161 and connector assembly 510 (the "optical connection"), such as no more that 20% of the optical connection stiffness, such as no more than 10% of the optical connection stiffness.

Figure 11:
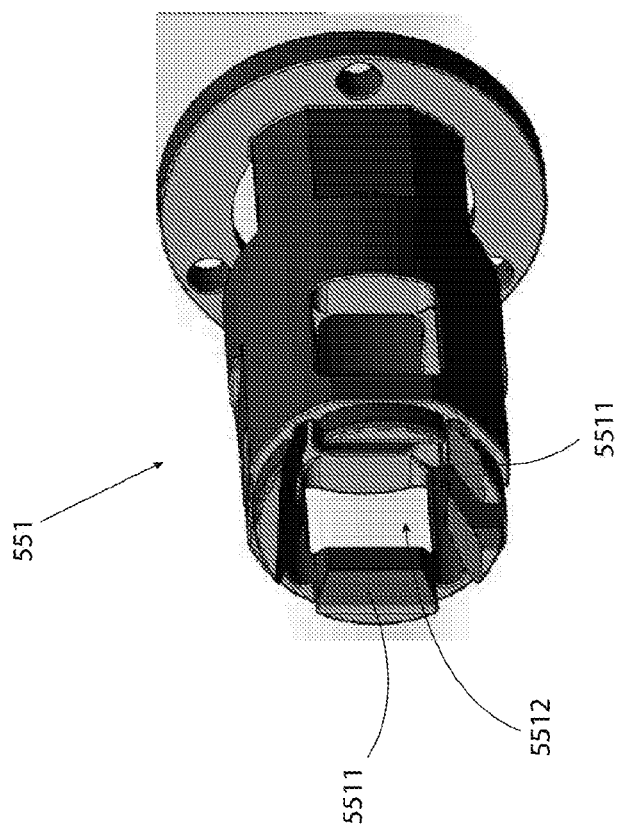
FIG. 11 is a perspective view of a receptacle, consistent with the present inventive concepts.

Referring now to FIG. 11, a perspective view of a receptacle is illustrated, consistent with the present inventive concepts. In some embodiments, rotary joint 550 of rotation assembly 500 can comprise a female connecting portion, receptacle 551. Receptacle 551 can be configured to slidingly receive optical connector 161 of connector assembly 150, such as to operably (e.g. rotatably and/or optically) attach optical core 110 to rotating assembly 500. Receptacle 551 can comprise one or more distal faces, faces 5511, and an opening 5512. Distal faces 5511 can comprise a chamfer, as shown. The chamfer of distal faces 5511 can comprise a chamfer sufficient to capture optical connector 161 when optical connector is misaligned from the center of connector assembly 150 a maximum possible distance within connector assembly 150 (e.g. when a portion of rotating assembly 160 and/or locking assembly 170 is resting against connector body 151 during the mating of imaging probe 100 to PIM 200). In some embodiments, the chamfer of distal faces 5511 allows proper connection to optical connector 161 when optical connector 161 is misaligned (e.g. during the connection process) up to 0.05", such as up to 0.075", such as a misalignment that can result due to the flexibility of shaft 169 (e.g. when shaft 169 is configured as described hereabove in reference to FIG. 10H). In some embodiments, the spacing between and carrier 163 and connector body 151 determines a maximum possible misalignment of optical connector 161.

The above-described embodiments should be understood to serve only as illustrative examples; further embodiments are envisaged. Any feature described herein in relation to any one embodiment may be used alone, or in combination with other features described, and may also be used in combination with one or more features of any other of the embodiments, or any combination of any other of the embodiments. Furthermore, equivalents and modifications not described above may also be employed without departing from the scope of the invention, which is defined in the accompanying claims.

What is claimed is:

1. An imaging system for a patient comprising:
    an imaging probe, comprising:
        an elongate shaft comprising a proximal end, a distal portion, and a lumen extending between the proximal end and the distal portion;
        a rotatable optical core comprising a proximal end and a distal end, wherein at least a portion of the rotatable optical core is positioned within the lumen of the elongate shaft; and
        an optical assembly positioned proximate the distal end of the rotatable optical core, the optical assembly configured to direct light to tissue and collect reflected light from the tissue; and
    a console constructed and arranged to operably attach to the imaging probe, the console comprising an imaging assembly constructed and arranged to optically couple to the imaging probe, wherein the imaging assembly is configured to emit light into the imaging probe and receive the reflected light collected by the optical assembly,
    wherein the reflected light comprises a back-reflection from an interface between the rotatable optical core and the optical assembly,
    wherein the optical assembly is configured to produce an identifiable back reflection,
    wherein the imaging assembly is configured to detect the identifiable back reflection without requiring the rotatable optical core to rotate,
    wherein a change in the identifiable back reflection correlates to an undesired state of the rotatable optical core,
    wherein the undesired state comprises a break in the rotatable optical core,
    wherein the console is configured to determine a distance between the identifiable back reflection and a center of a calibration image formed by the directed light,
    wherein the console is calibrated based on the determined distance.

2. The system according to claim 1, wherein the optical assembly comprises a GRIN lens.

3. The system according to claim 1, wherein the identifiable back reflection comprises at least one back-reflection.

4. The system according to claim 1, wherein the change in the identifiable back reflection comprises a loss of the identifiable back reflection.

5. The system according to claim 1, wherein the system is configured to enter an alert mode if the undesired state of the rotatable optical core is detected.

6. The system according to claim 1, wherein the imaging assembly is configured to detect the identifiable back reflection when the imaging probe is being advanced within the patient.

7. A method of calibrating an imaging system comprising:
    emitting light from an imaging assembly to an attached imaging probe, the imaging probe comprising:
        a rotatable optical core comprising a proximal end and a distal end; and
        an optical assembly positioned proximate the distal end of the rotatable optical core, the optical assembly configured to direct light to tissue and collect reflected light from the tissue;
    receiving light from the imaging probe with the imaging assembly, wherein the received light includes light from a back-reflection at an interface of the rotatable optical core and the optical assembly;
    wherein the optical assembly is configured to produce an identifiable back reflection,
    wherein the imaging assembly is configured to detect the identifiable back reflection,
    wherein a change in the identifiable back reflection correlates to an undesired state of the rotatable optical core, and
    wherein the undesired state comprises a break in the rotatable optical core,
    and wherein the method further comprises:
    determining a distance between the identifiable back reflection and a center of a calibration image formed by the received light; and
    calibrating the console based on the determined distance.

8. The method according to claim 7, wherein the rotatable optical core is not rotated during the calibration.

9. The method according to claim 7, wherein the calibration comprises adjusting a length of a reference path.

10. The method according to claim 9, wherein the imaging assembly comprises a delay line.

11. The method according to claim 10, wherein the delay line comprises a step size of no more than 15 μm.

* * * * *

UNITED STATES PATENT AND TRADEMARK OFFICE
CERTIFICATE OF CORRECTION

PATENT NO. : 12,262,872 B2
APPLICATION NO. : 17/276500
DATED : April 1, 2025
INVENTOR(S) : Christopher L. Petersen et al.

Page 1 of 1

It is certified that error appears in the above-identified patent and that said Letters Patent is hereby corrected as shown below:

In the Claims

Column 38, Line 20, Claim 1, insert --and-- after "the directed light,".

Signed and Sealed this
Seventeenth Day of June, 2025

Coke Morgan Stewart
*Acting Director of the United States Patent and Trademark Office*